United States Patent [19]

Narula et al.

[11] Patent Number: 5,731,283
[45] Date of Patent: Mar. 24, 1998

[54] 1(4'-METHYLPENTYL)-4-SUBSTITUTED ETHYLCYCLOHEXANE DERIVATIVES, ORGANOLEPTIC USES THEREOF, PROCESS FOR PRODUCING SAME, AND PROCESS INTERMEDIATES THEREFOR

[75] Inventors: Anubhav P. S. Narula; James Joseph Koestler, both of Hazlet, N.J.; Jan Van Elst, HM Bilthoven, Netherlands

[73] Assignee: International Flavors & Fragrances Inc., New York, N.Y.

[21] Appl. No.: 789,379

[22] Filed: Jan. 28, 1997

[51] Int. Cl.$^6$ ...................................................... A61K 7/46
[52] U.S. Cl. ........................... 512/22; 560/231; 568/376; 568/377; 568/667; 568/579; 568/822; 568/826; 252/174.11

[56] References Cited

FOREIGN PATENT DOCUMENTS 896039  9/1962  United Kingdom ...................... 512/22

*Primary Examiner*—James H. Reamer
*Attorney, Agent, or Firm*—Arthur L. Liberman

[57] ABSTRACT

Described are 1(4'-methylpentyl)-4-substituted ethylcyclohexane derivatives defined according to the structure:

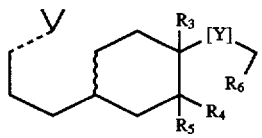

wherein $R_3$, $R_4$, $R_5$ and $R_6$ are the same or different hydrogen or methyl; wherein the dashed line represents a carbon carbon single bond or a carbon carbon double bond; wherein the wavy line represents a carbon carbon single bond or a carbon carbon double bond; with the proviso that when the wavy line is a carbon carbon single bond then the dashed line is a carbon carbon single bond; wherein Y represents a moiety selected from the group consisting of:

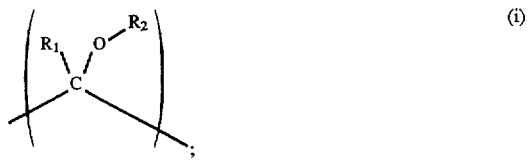

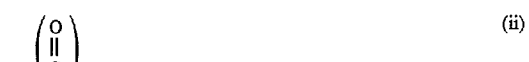

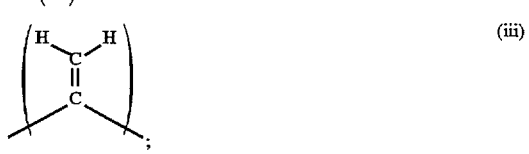

wherein H represents hydrogen, $C_1$–$C_4$ lower alkyl or $C_1$–$C_2$ acyl; and wherein $R_1$ represents $C_1$–$C_4$ lower alkyl with the additional proviso that when Y is the moiety:

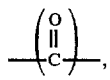

then the dashed line is a carbon carbon single bond, and uses thereof in augmenting, enhancing or imparting aromas in or to perfume compositions, perfumed articles and colognes. Also described are processes for producing the abovementioned 1(4'-methylpentyl)-4-substituted ethylcyclohexane derivatives as well as intermediates used in said processes.

22 Claims, 56 Drawing Sheets

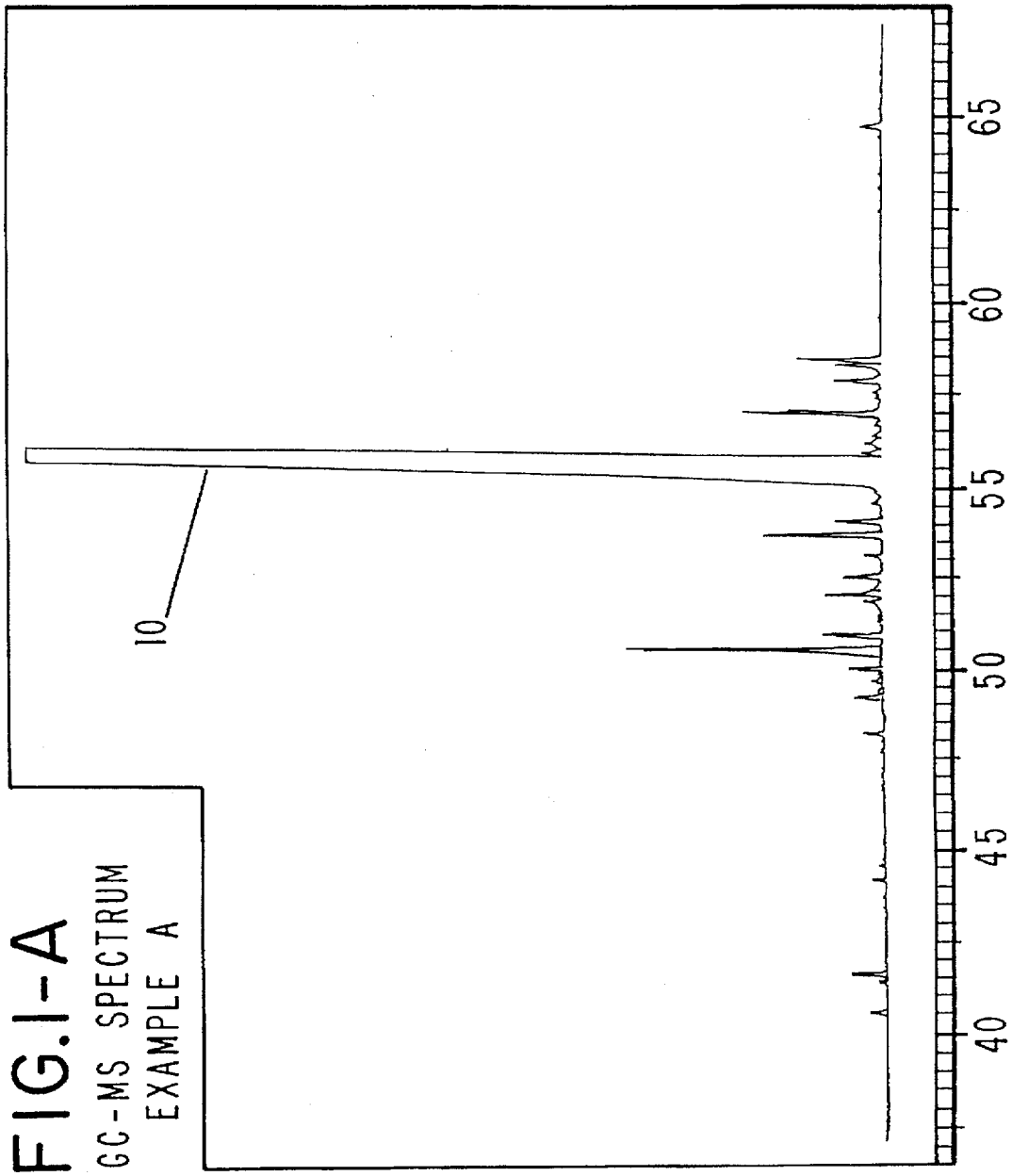
FIG.1-A GC-MS SPECTRUM EXAMPLE A

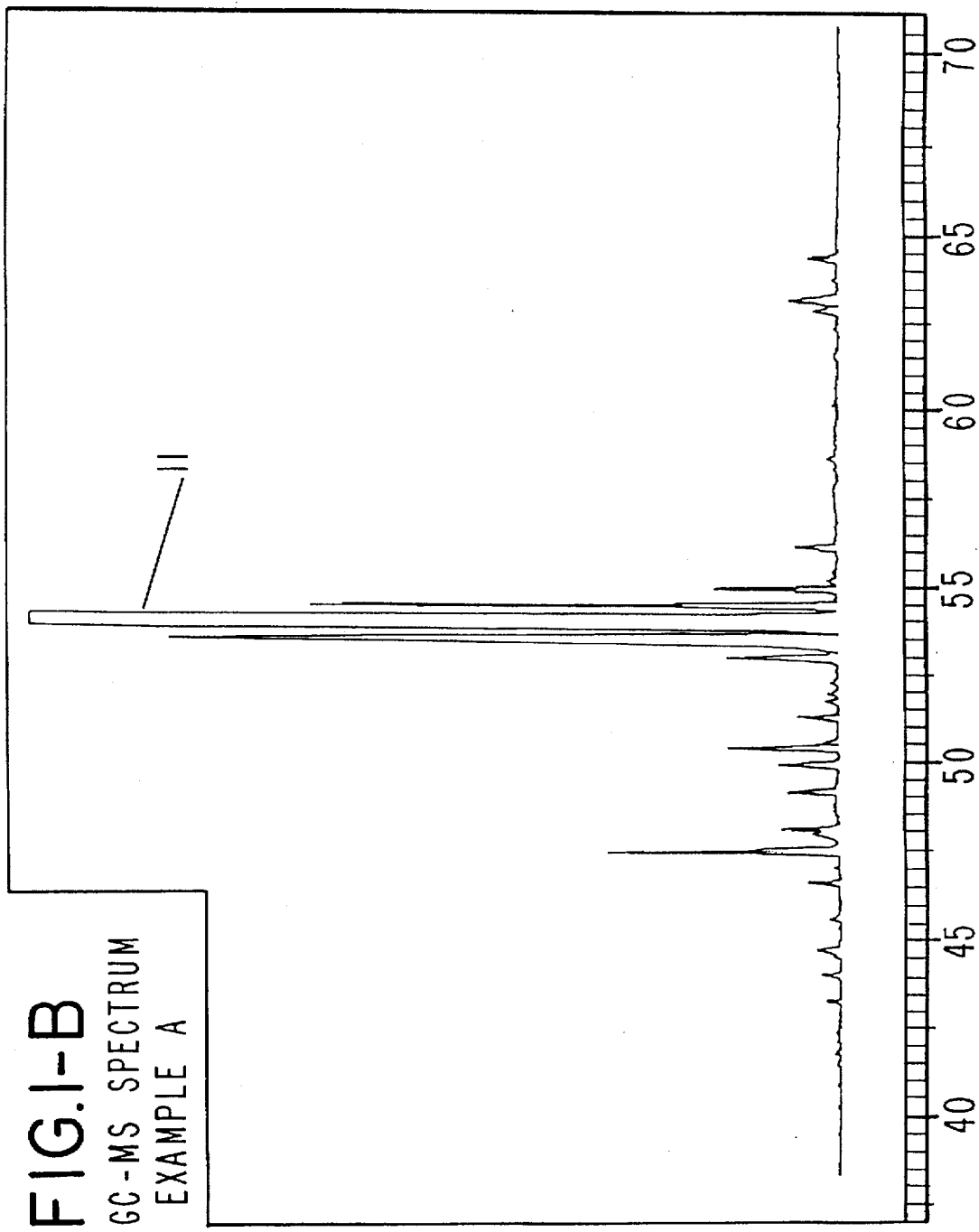
FIG.1-B
GC-MS SPECTRUM EXAMPLE A

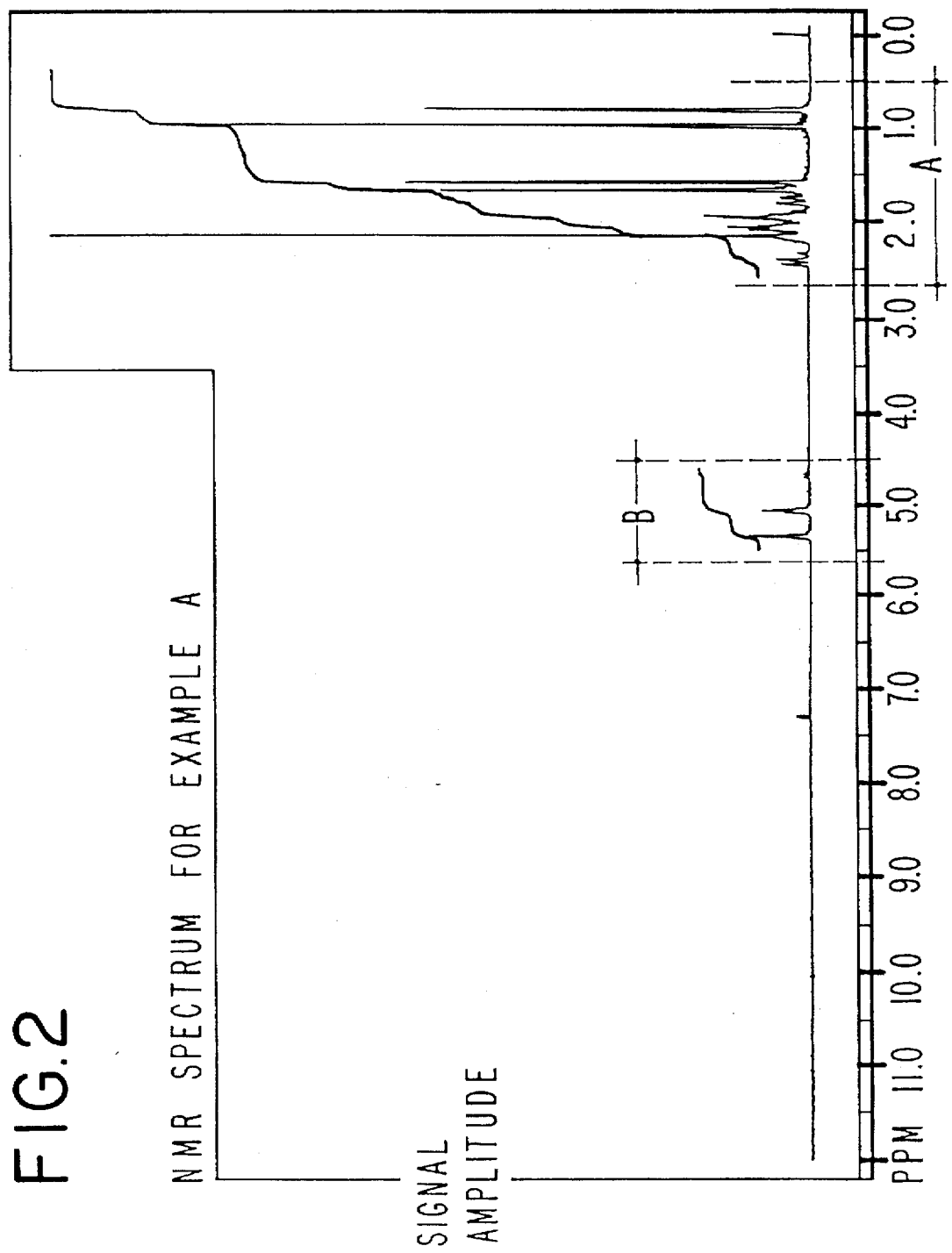
FIG.2 NMR SPECTRUM FOR EXAMPLE A

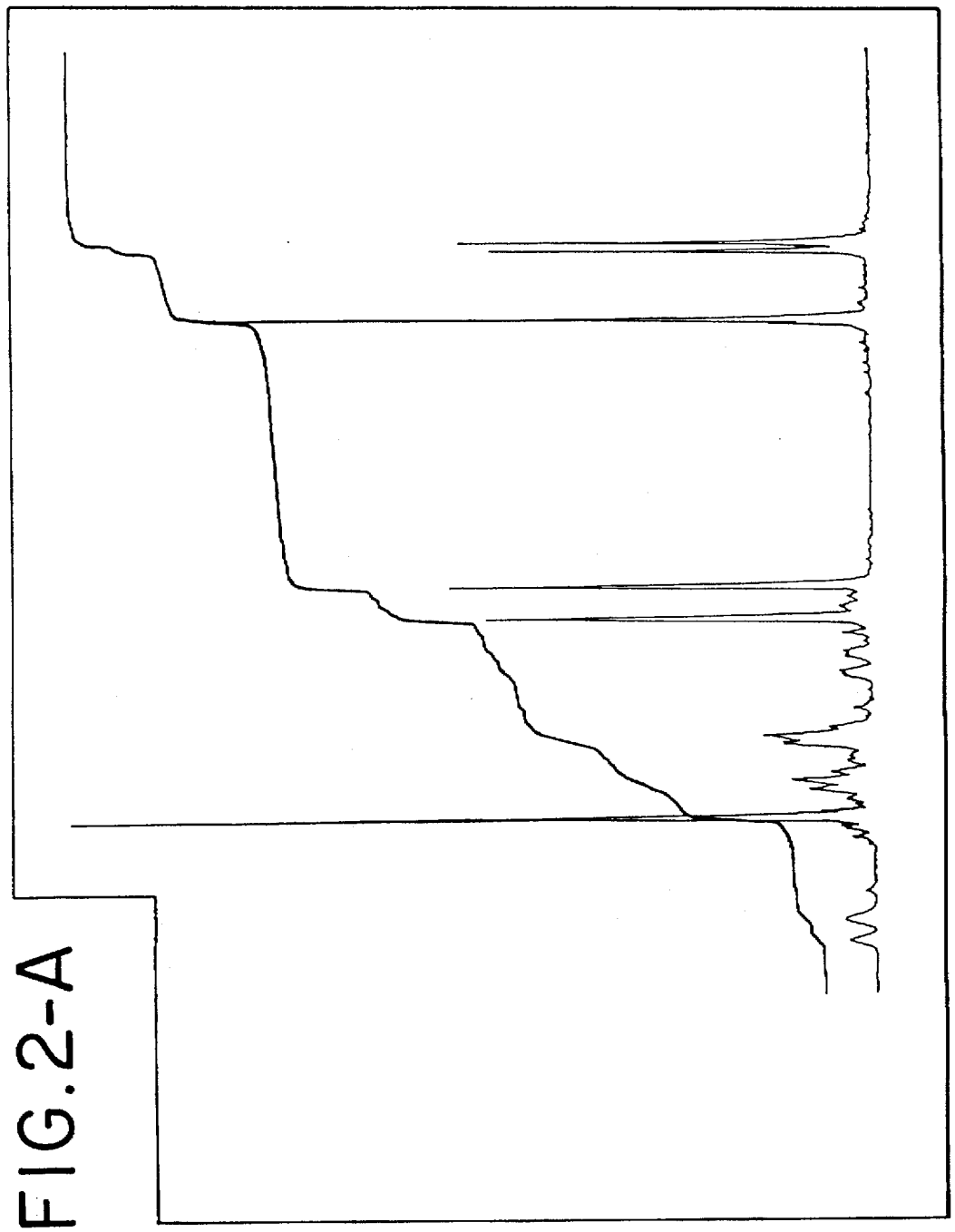
FIG.2-A

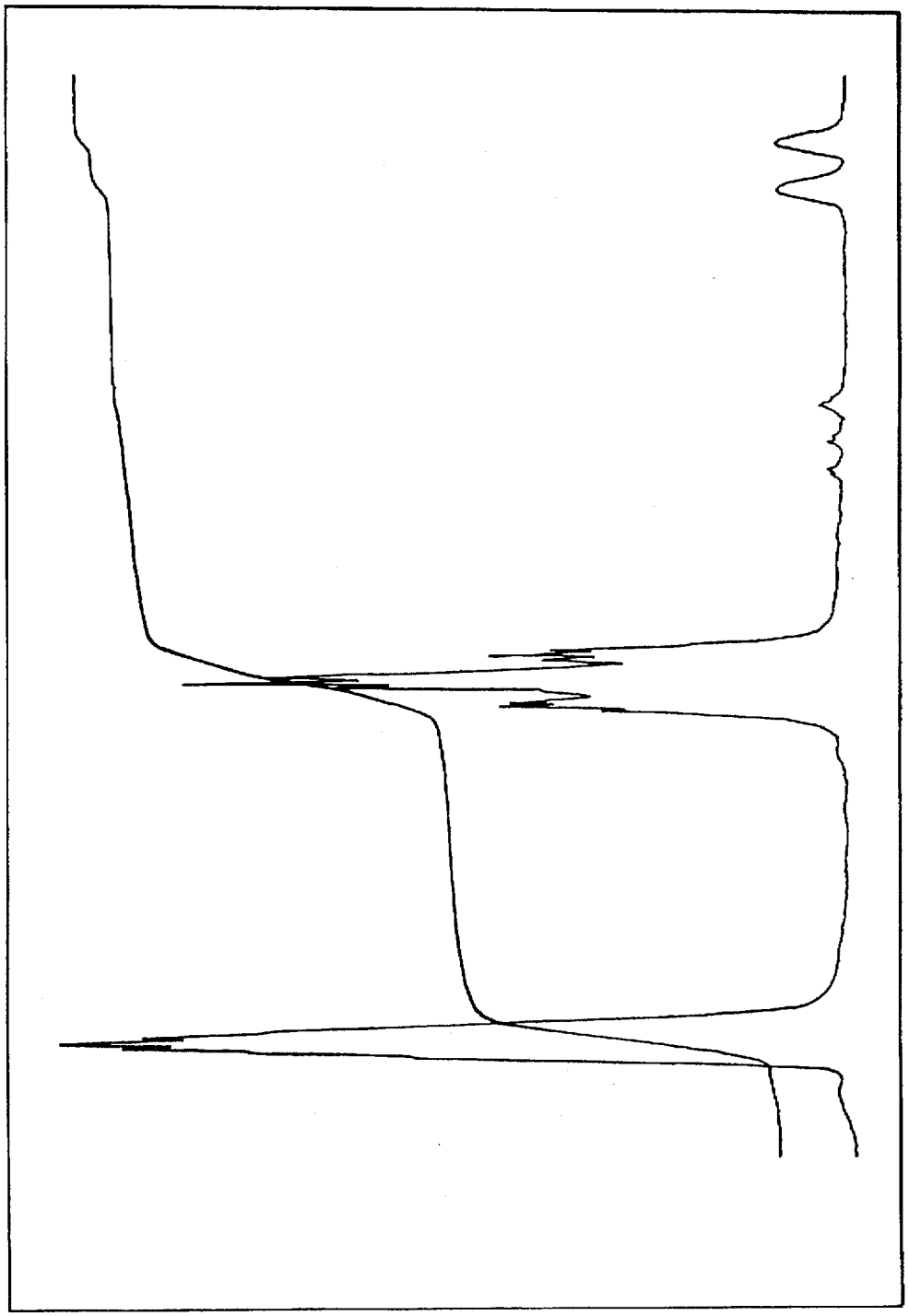
FIG.2-B

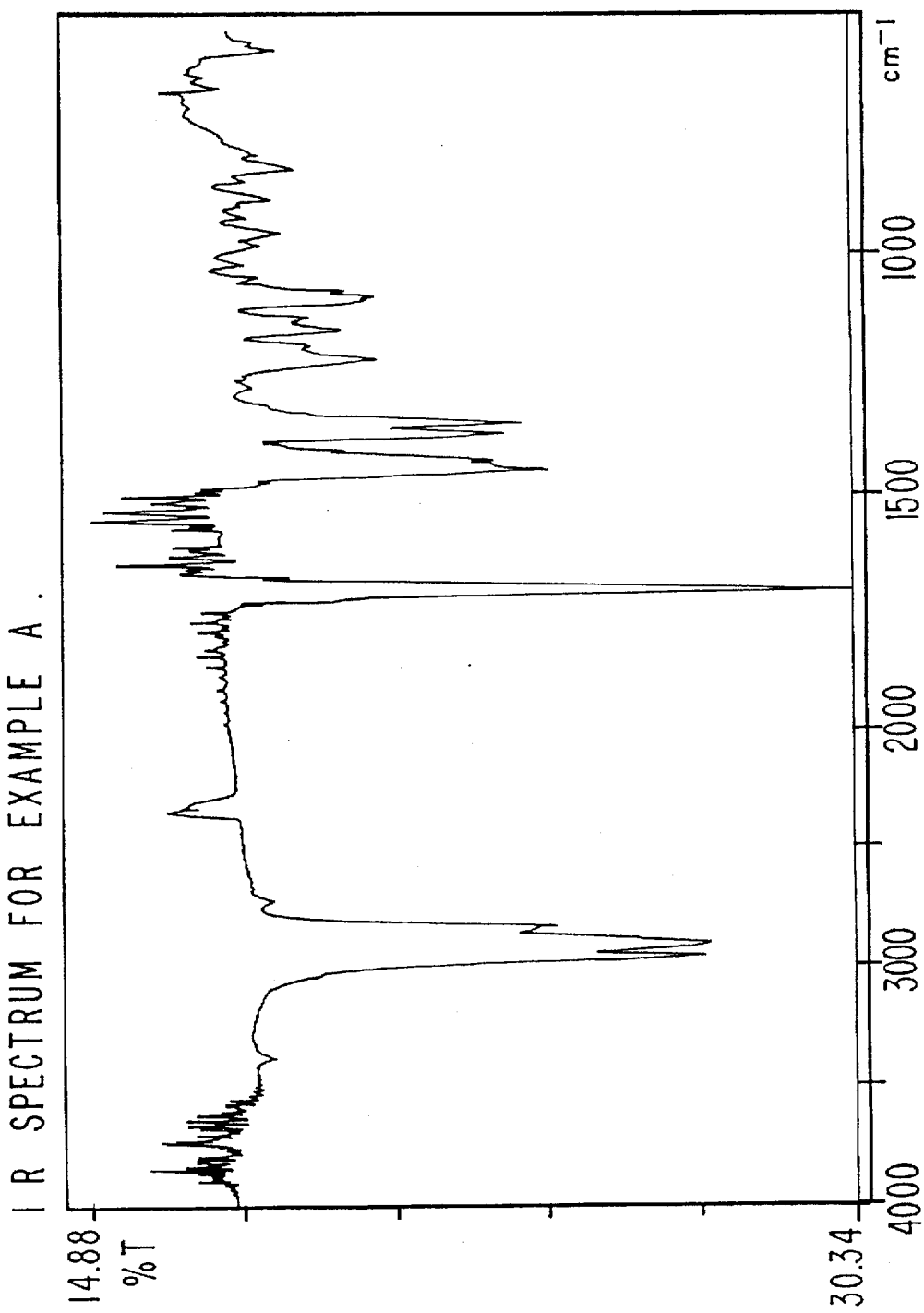
FIG.3 IR SPECTRUM FOR EXAMPLE A.

GLC PROFILE FOR EXAMPLE I.

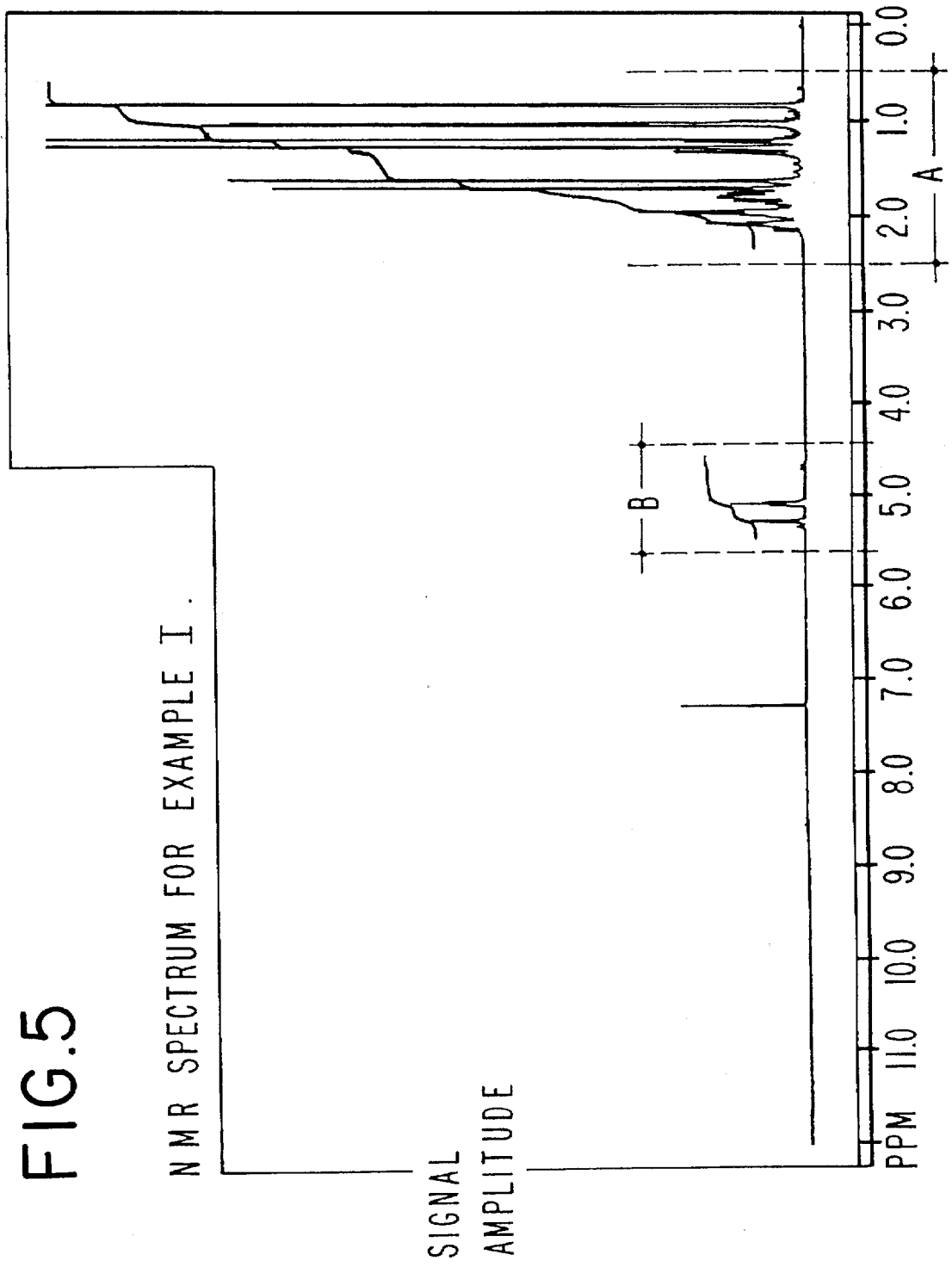
FIG. 5 NMR SPECTRUM FOR EXAMPLE I.

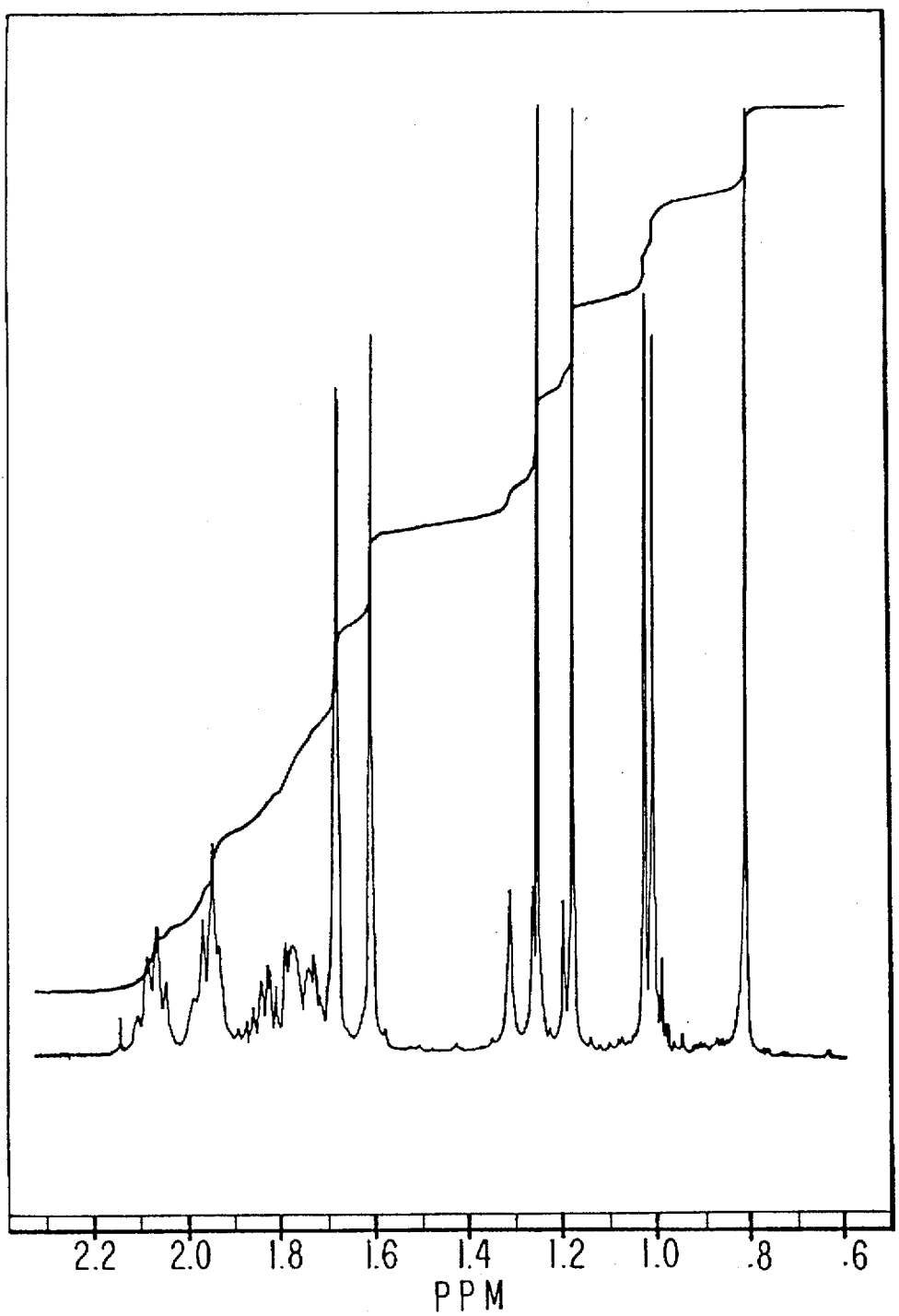
FIG.5-A

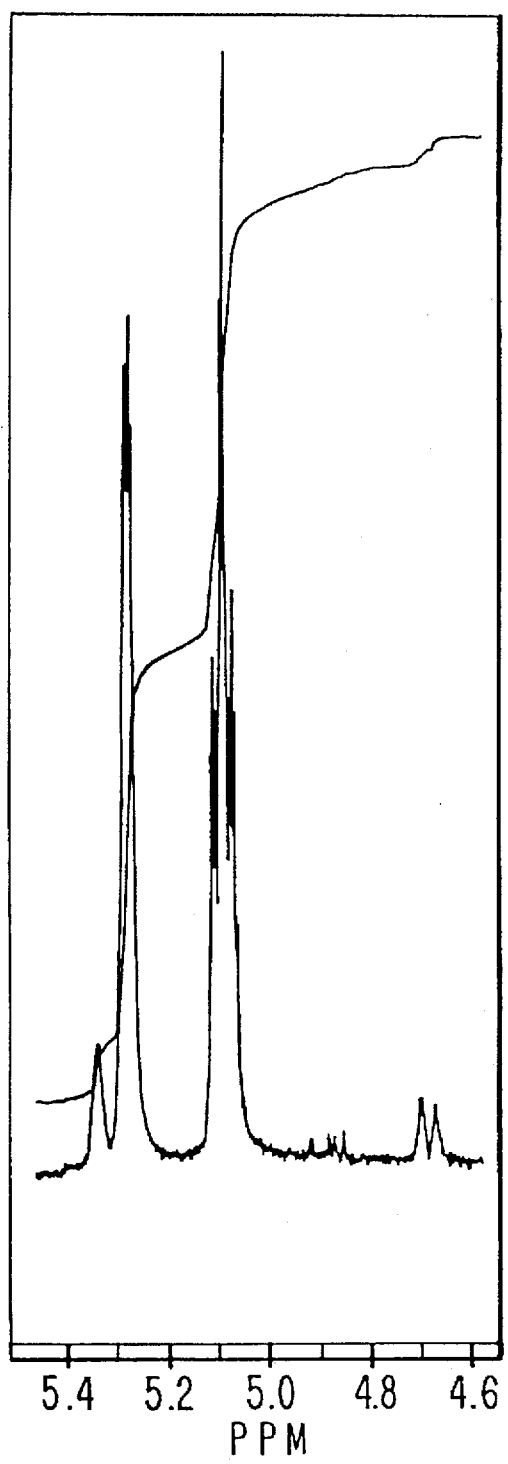
FIG.5-B

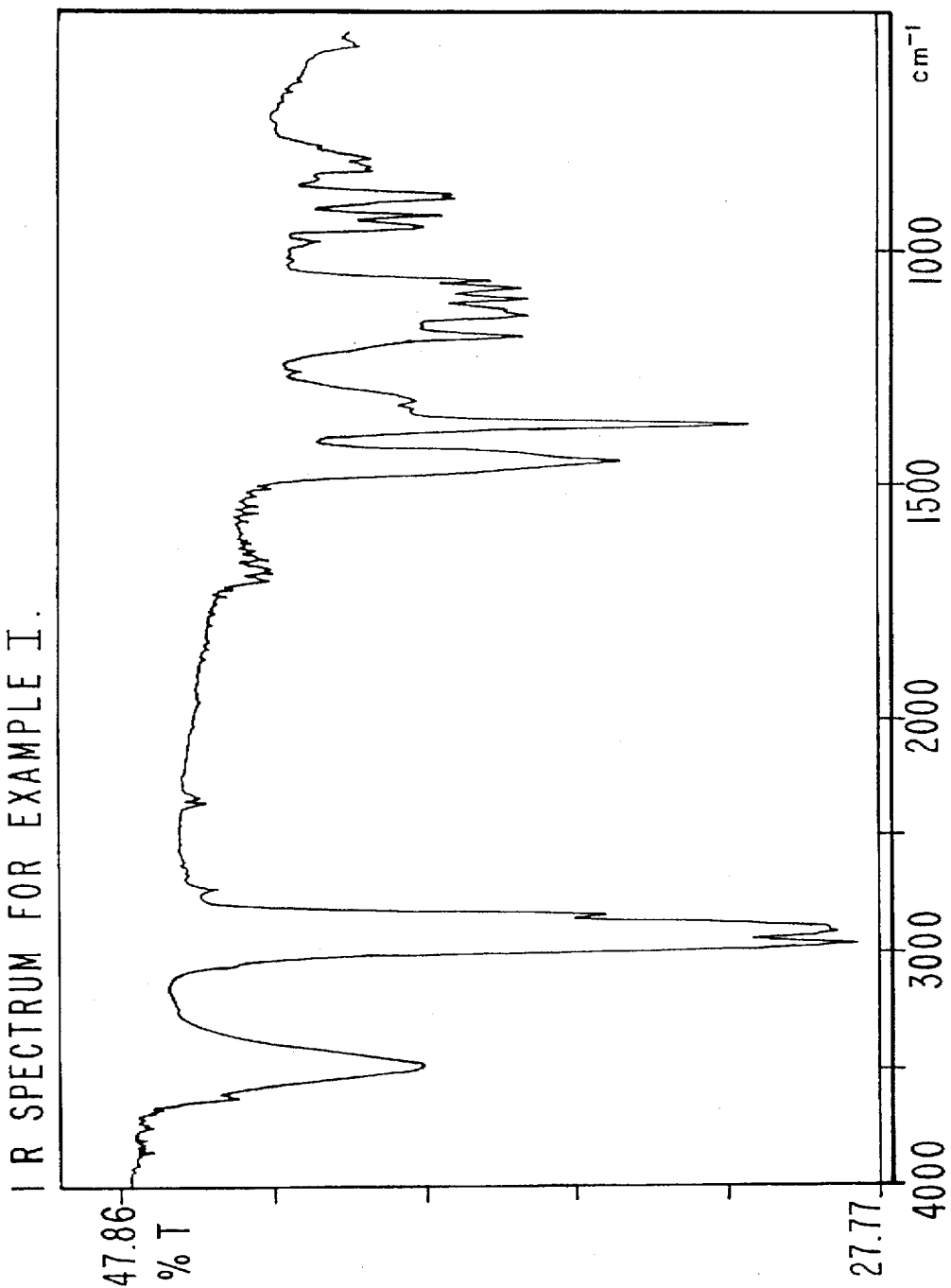

GLC PROFILE FOR EXAMPLE II

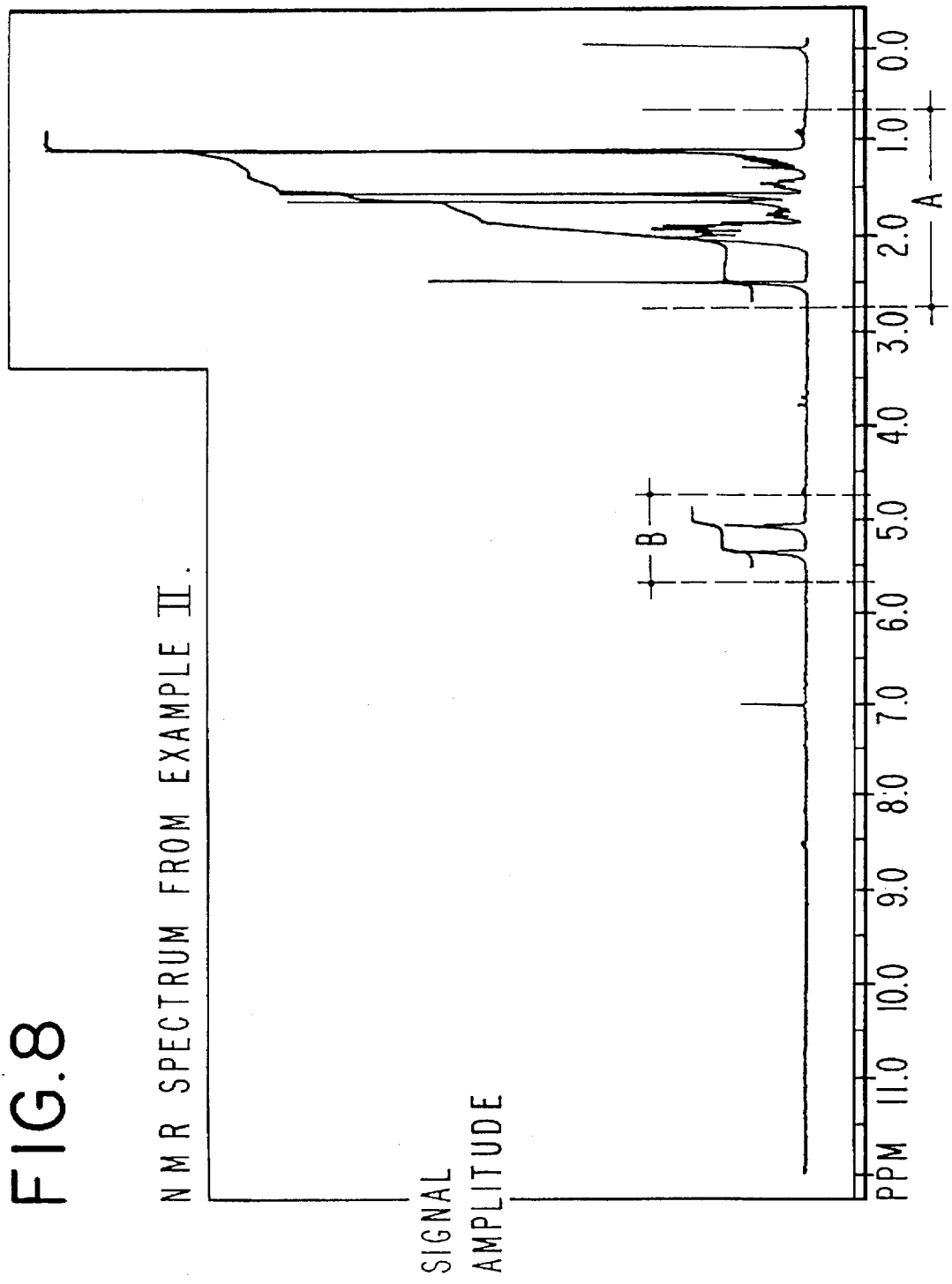

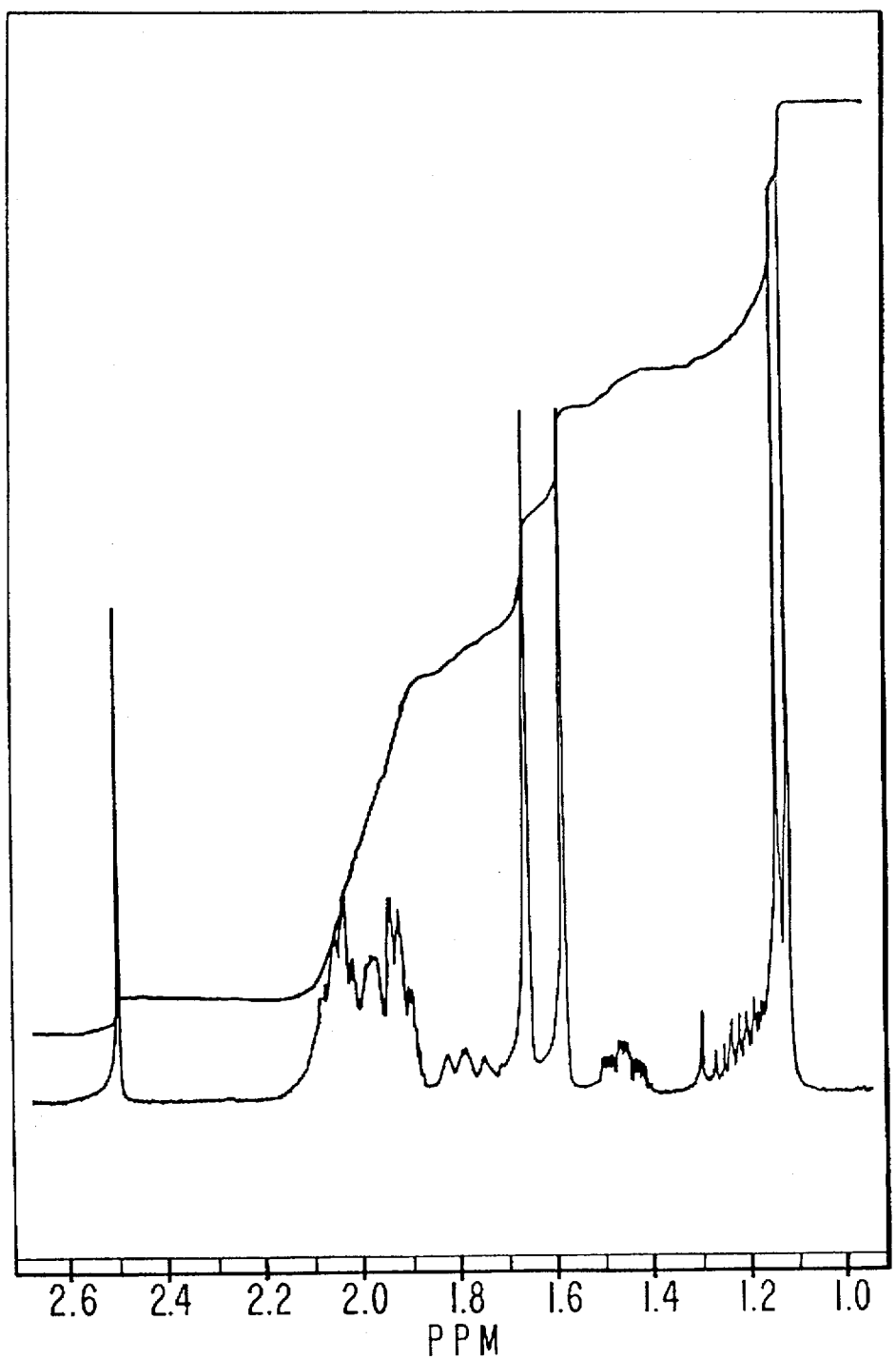
FIG.8-A

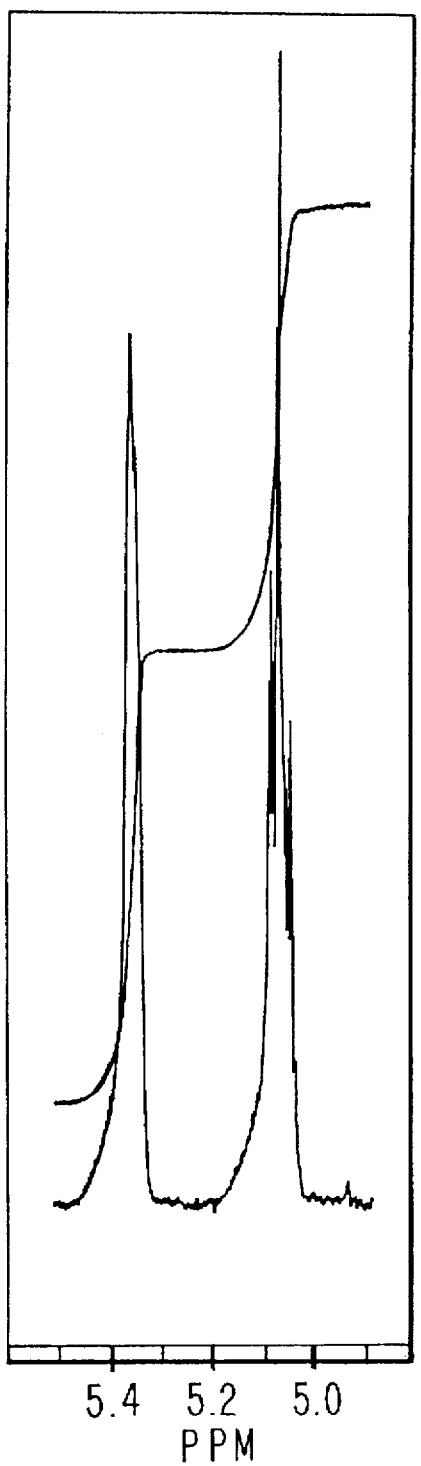
FIG. 8-B

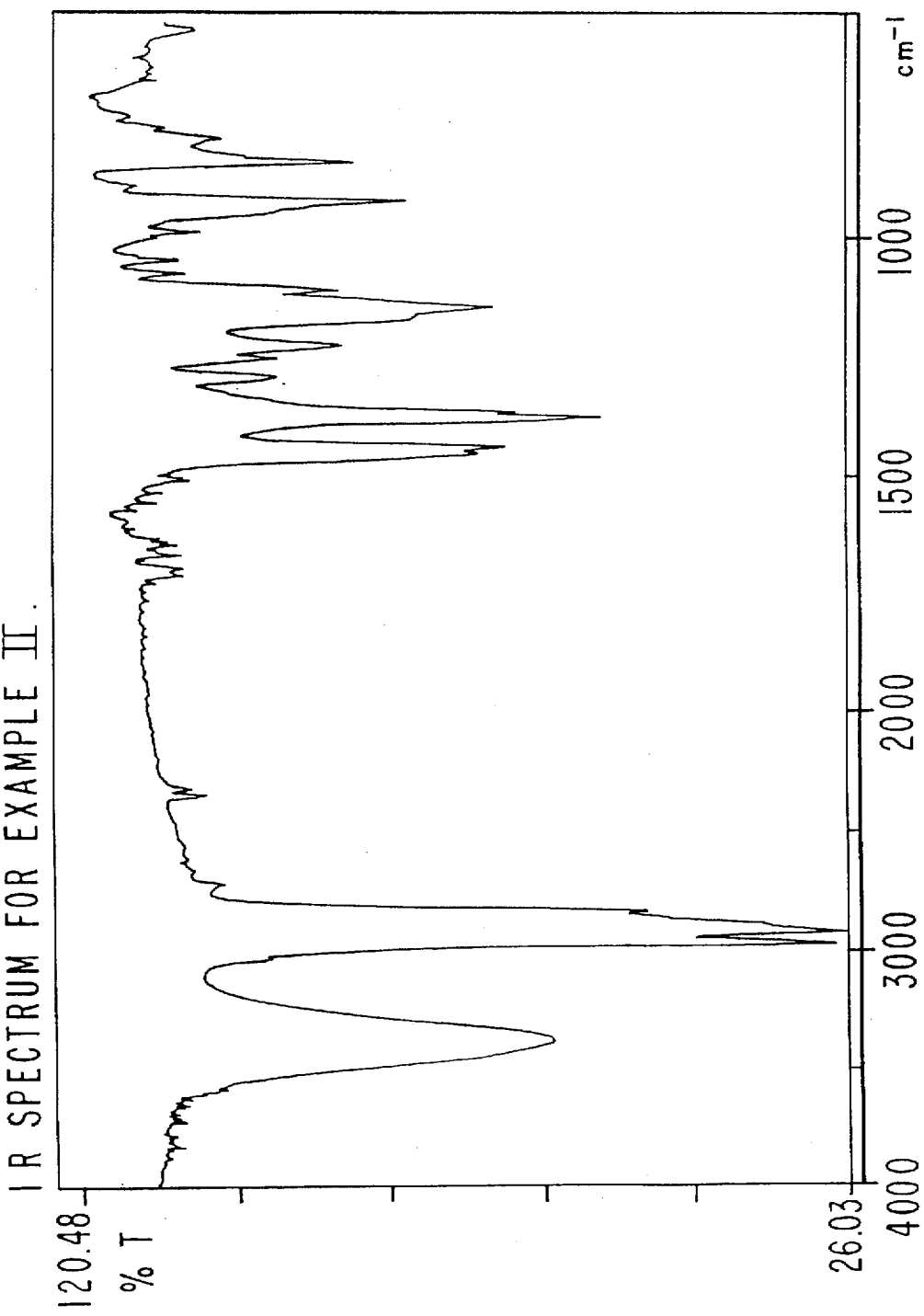

GLC PROFILE FOR EXAMPLE II

FIG.11 NMR SPECTRUM FOR EXAMPLE III.

GLC PROFILE FOR EXAMPLE IV.

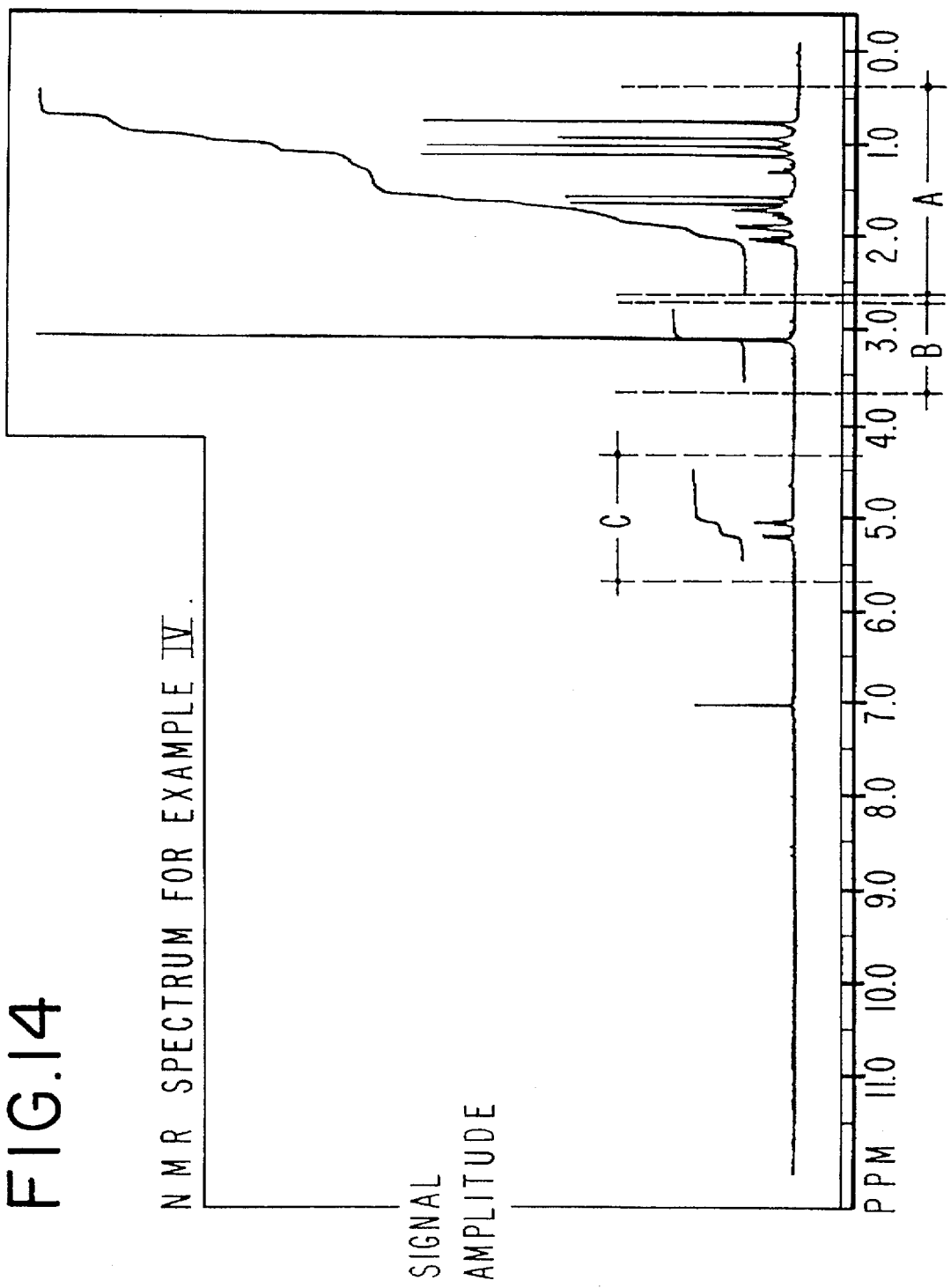
FIG. 14 NMR SPECTRUM FOR EXAMPLE IV

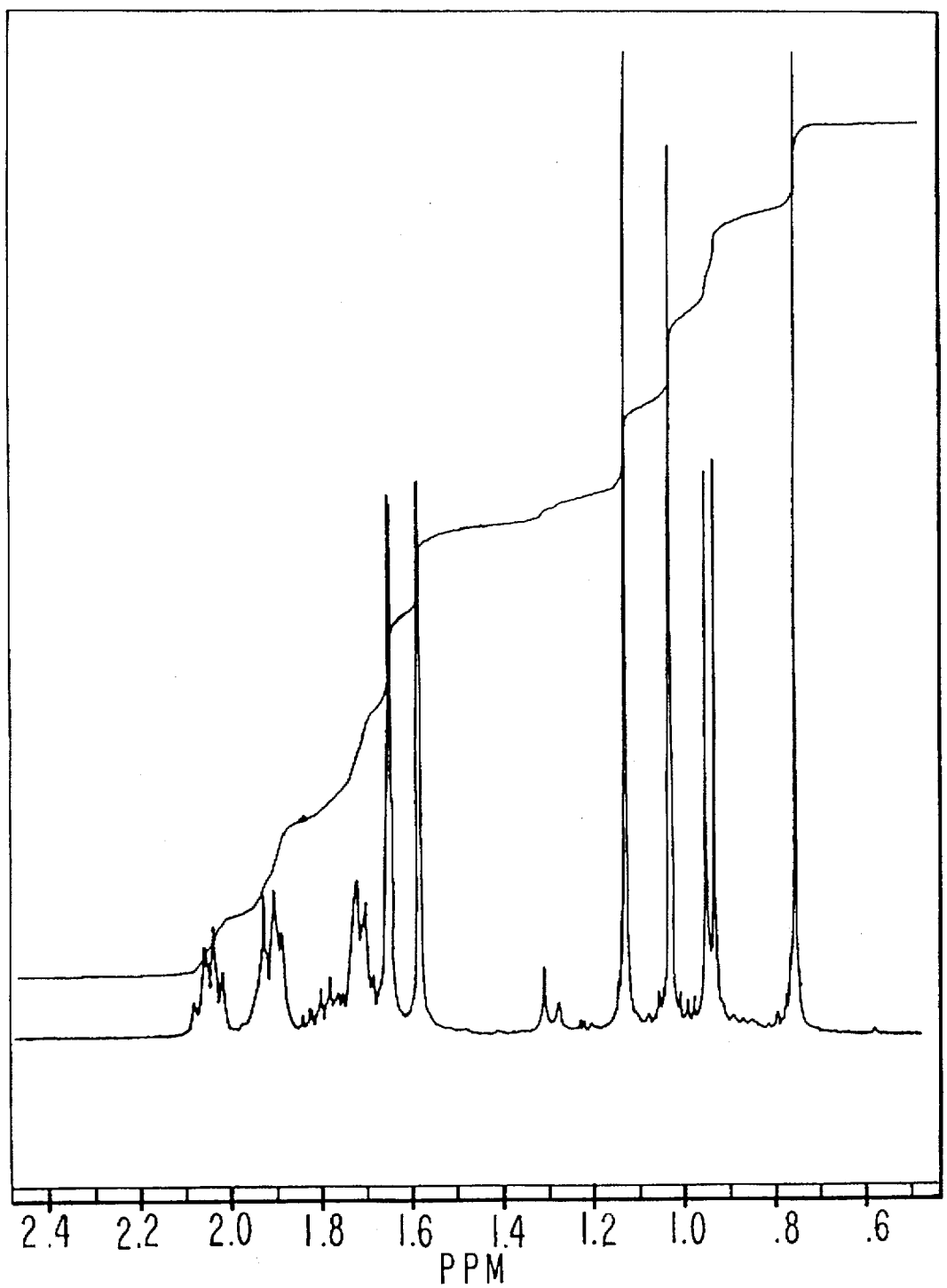
FIG.14-A

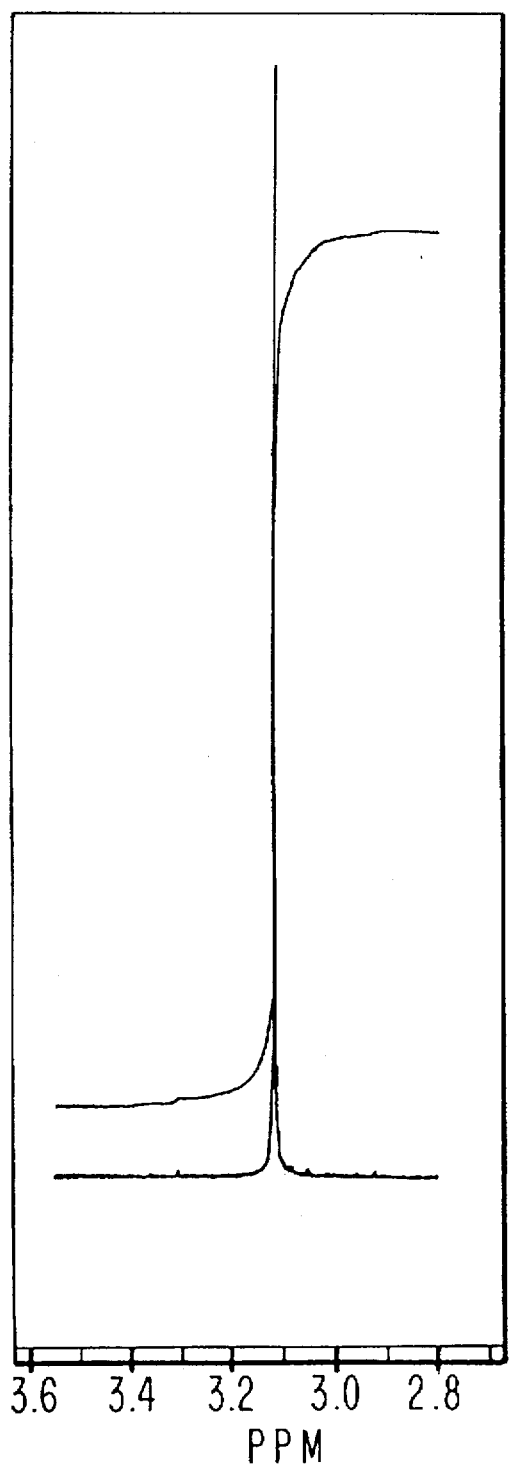
FIG.14-B

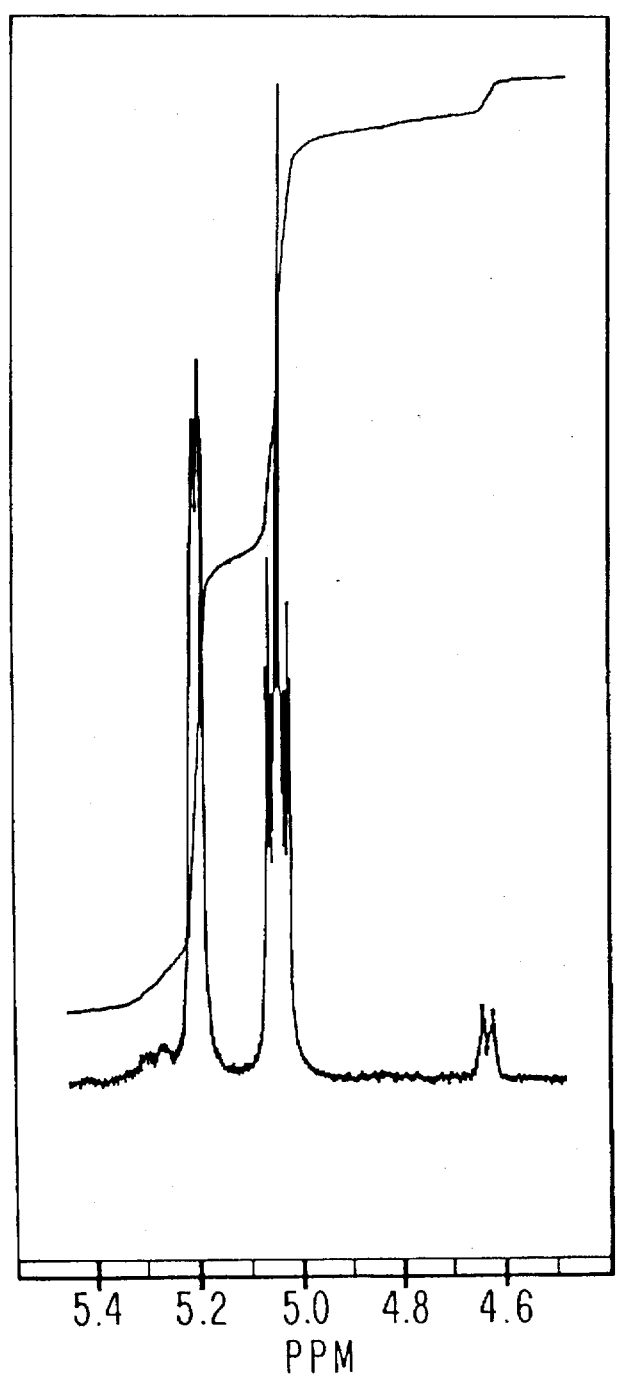
FIG. 14-C

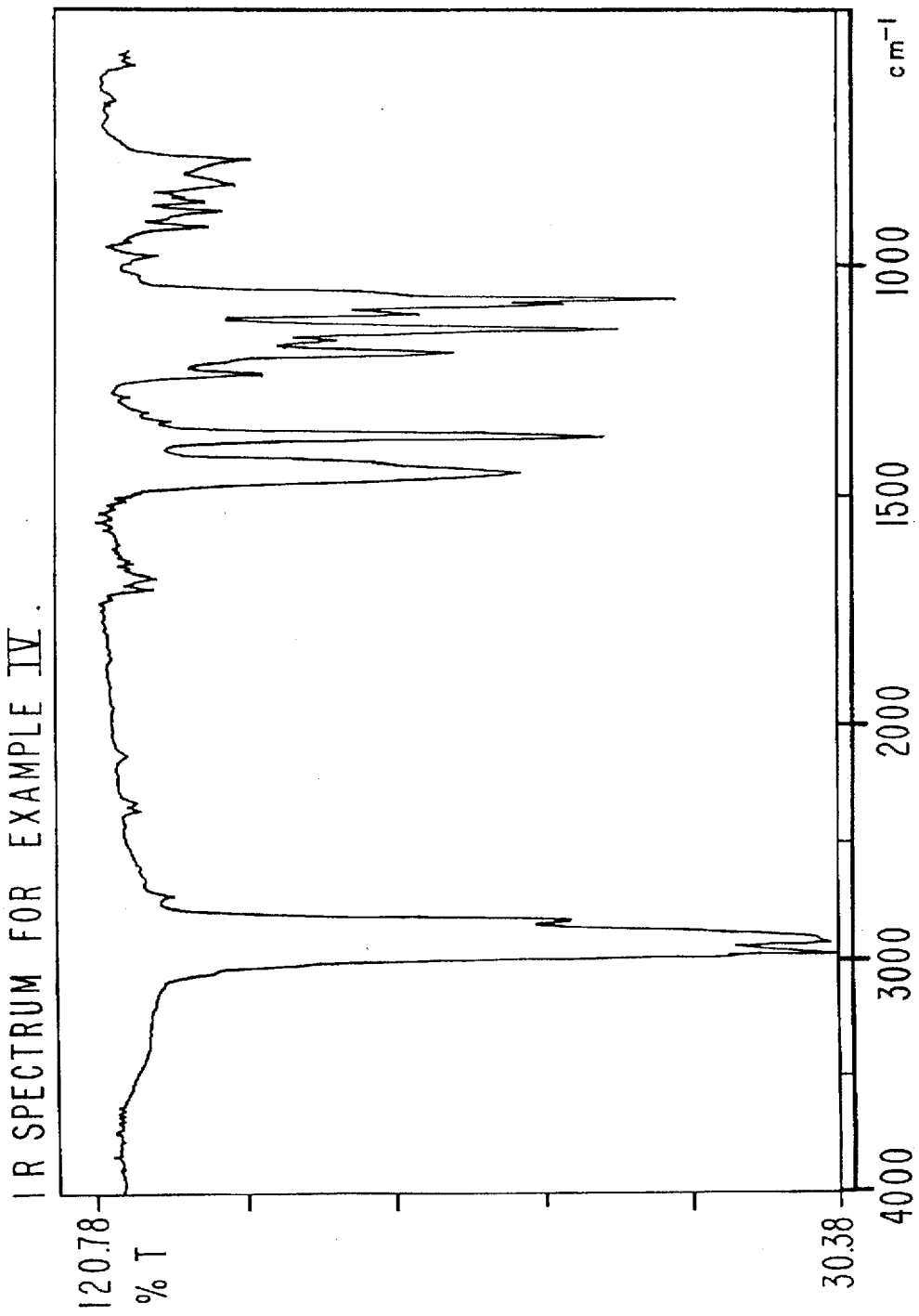

GLC PROFILE FOR EXAMPLE V.

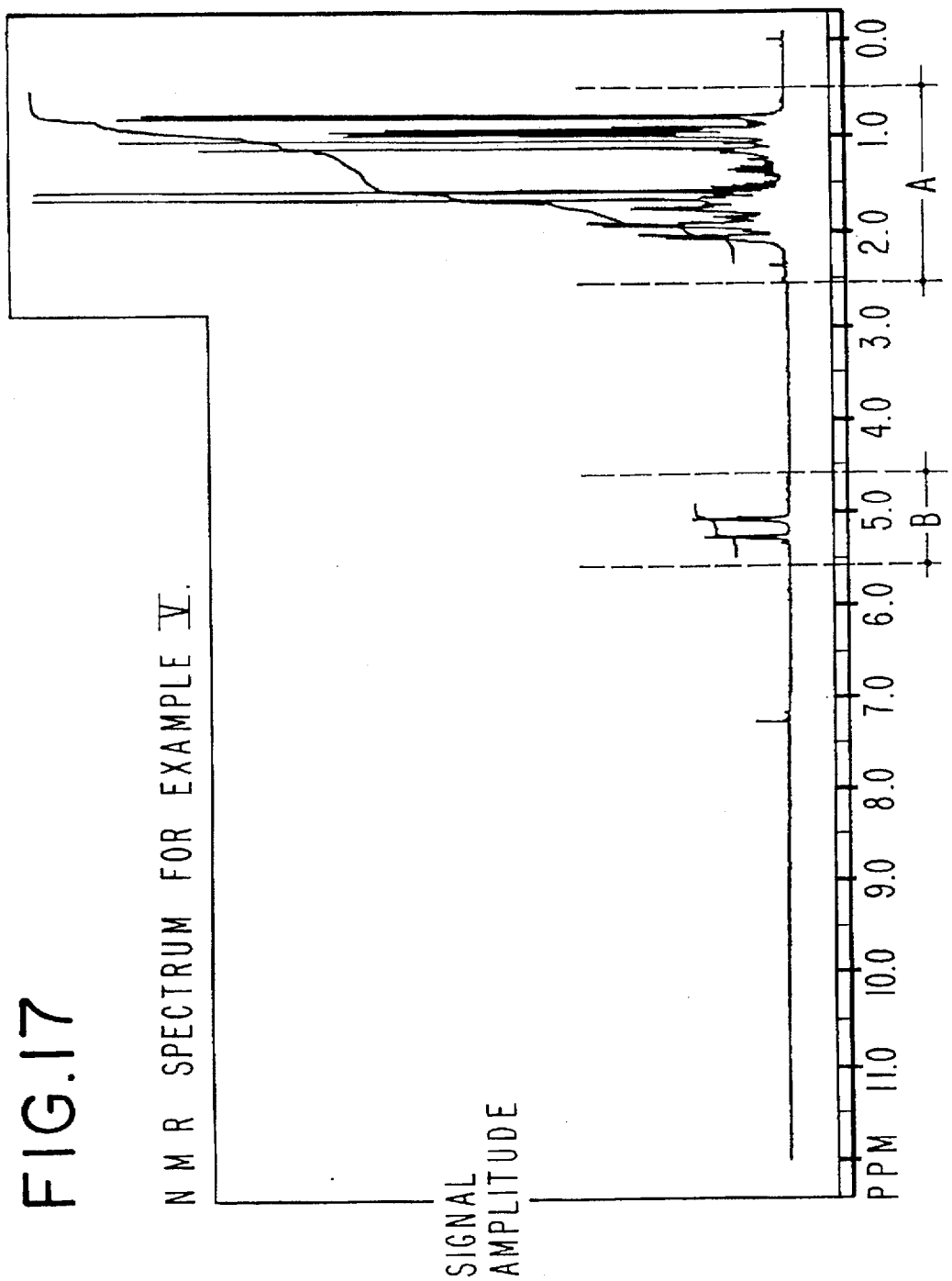
FIG. 17 NMR SPECTRUM FOR EXAMPLE V.

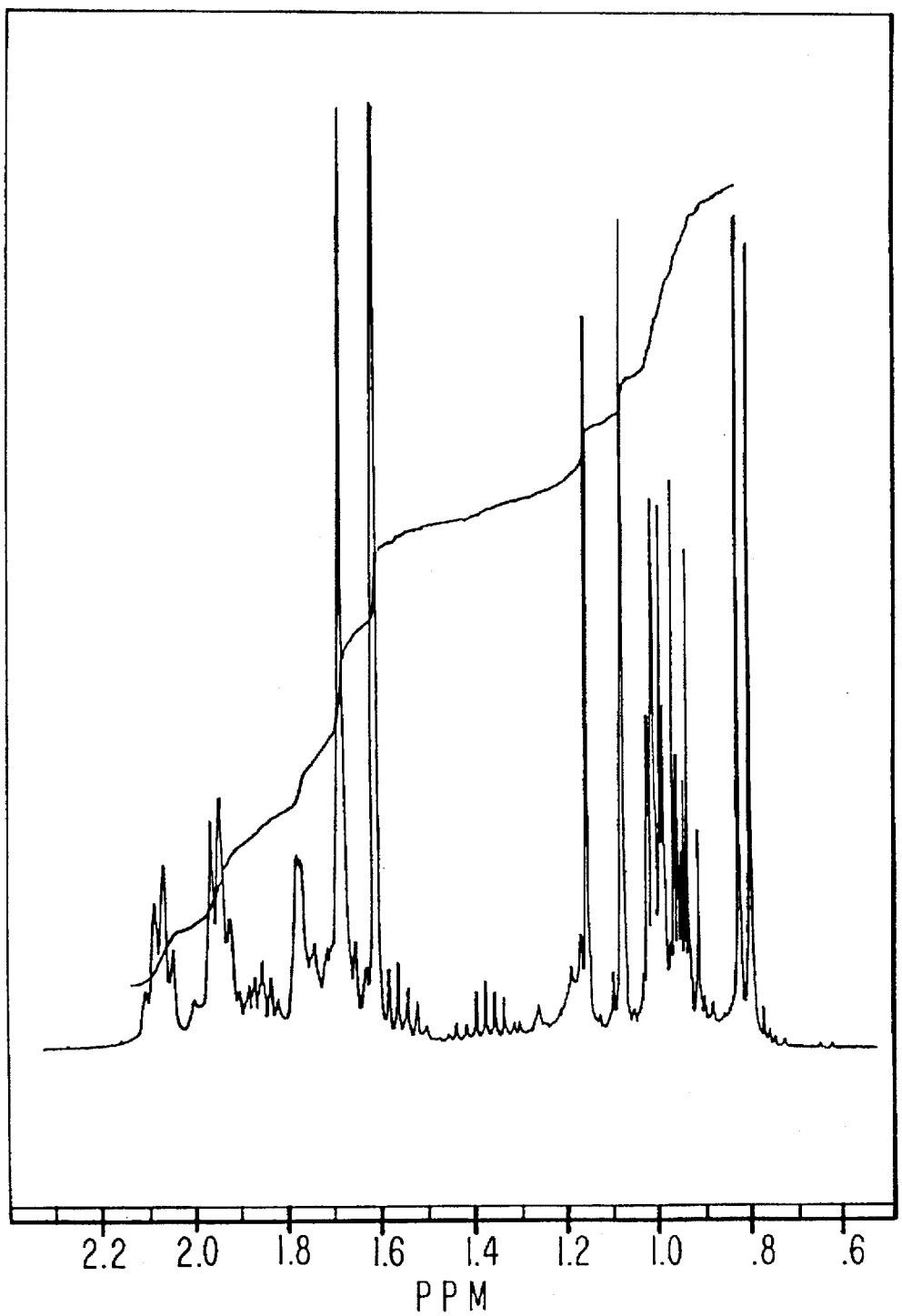
FIG.17-A

FIG.17-B
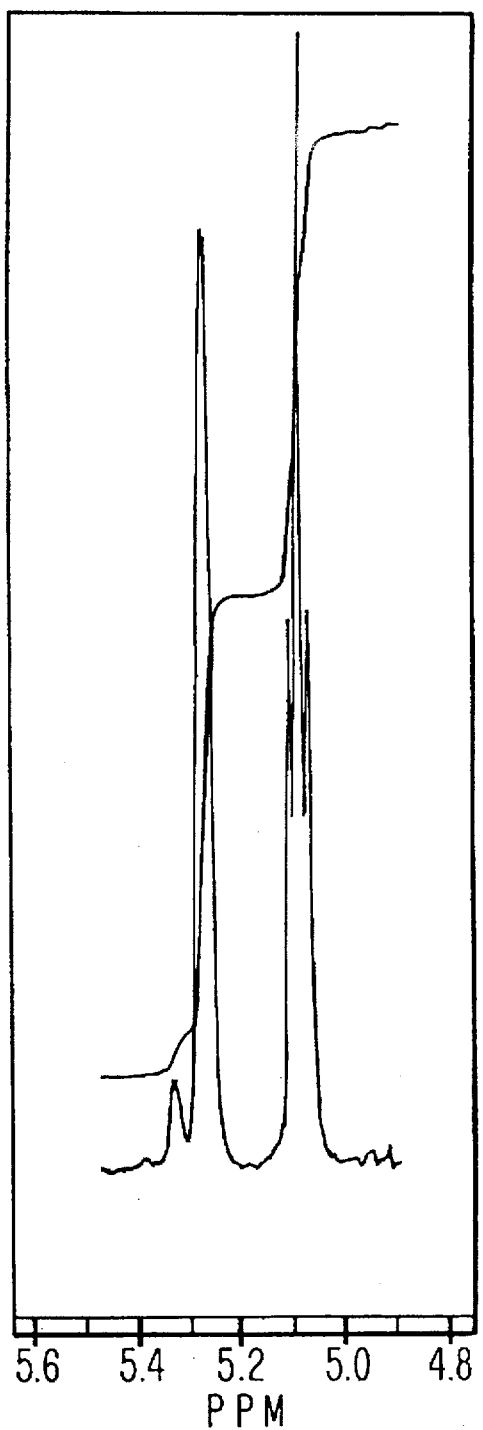

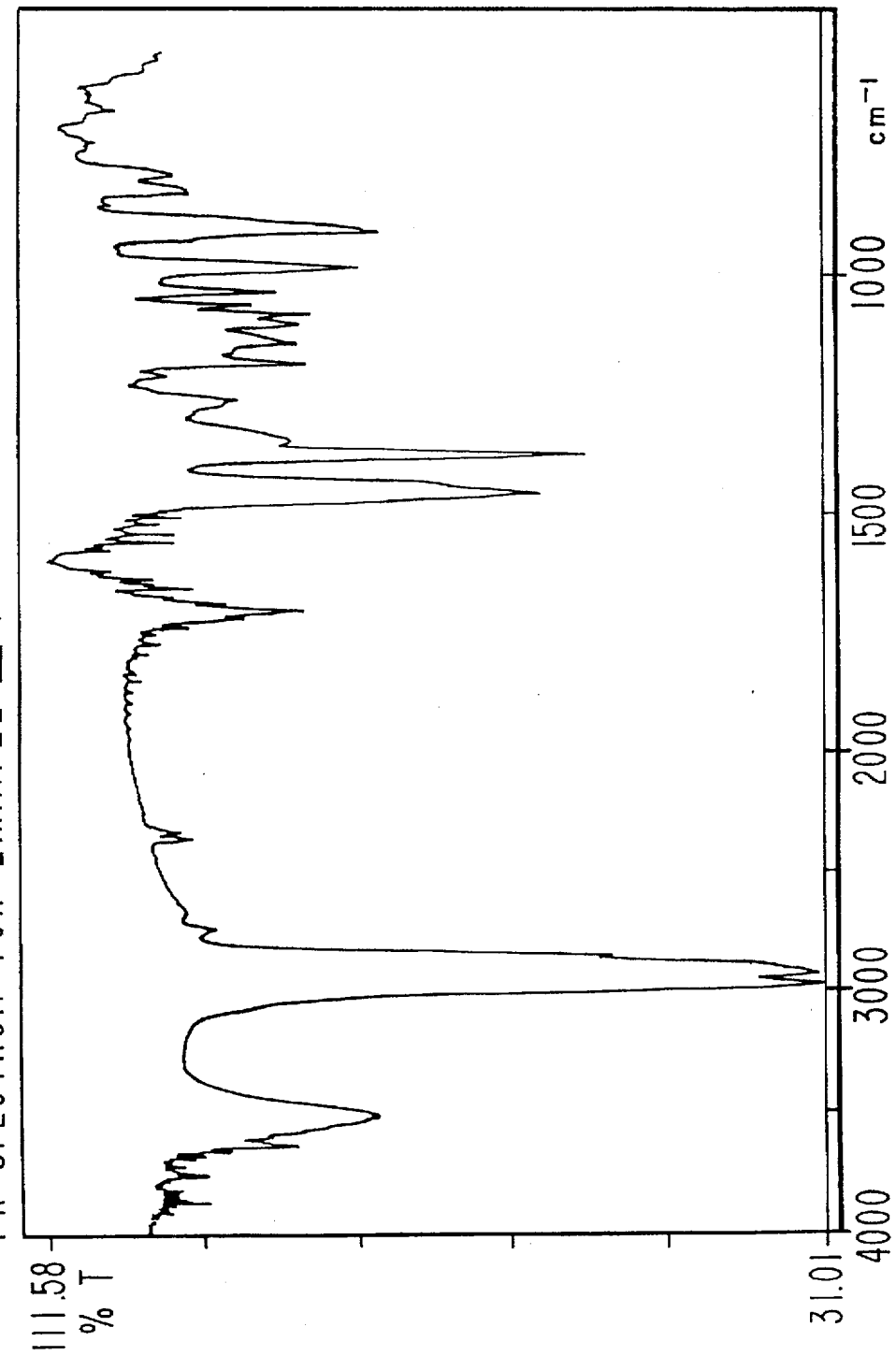

GLC PROFILE FOR EXAMPLE VI.

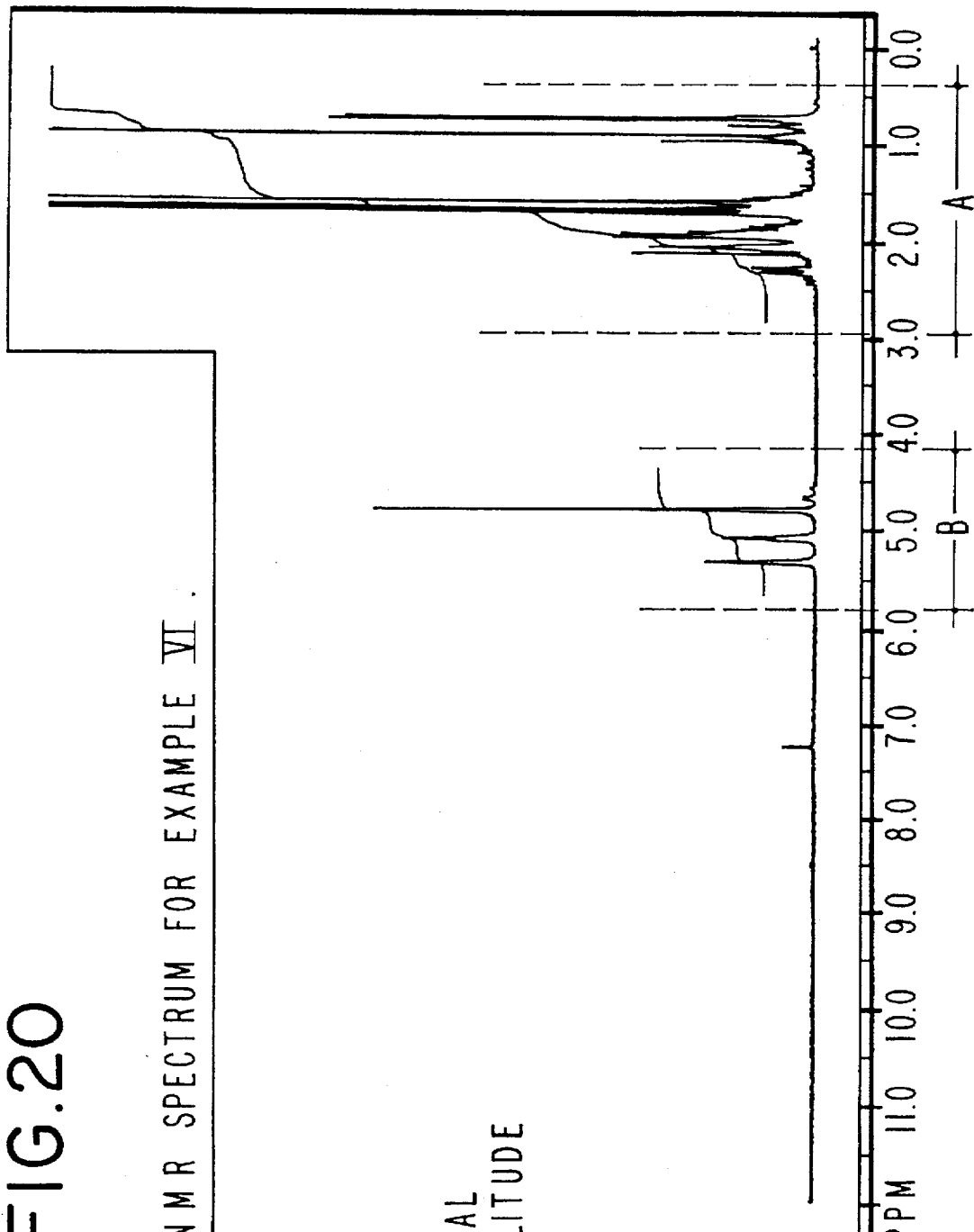
FIG. 20 NMR SPECTRUM FOR EXAMPLE VI.

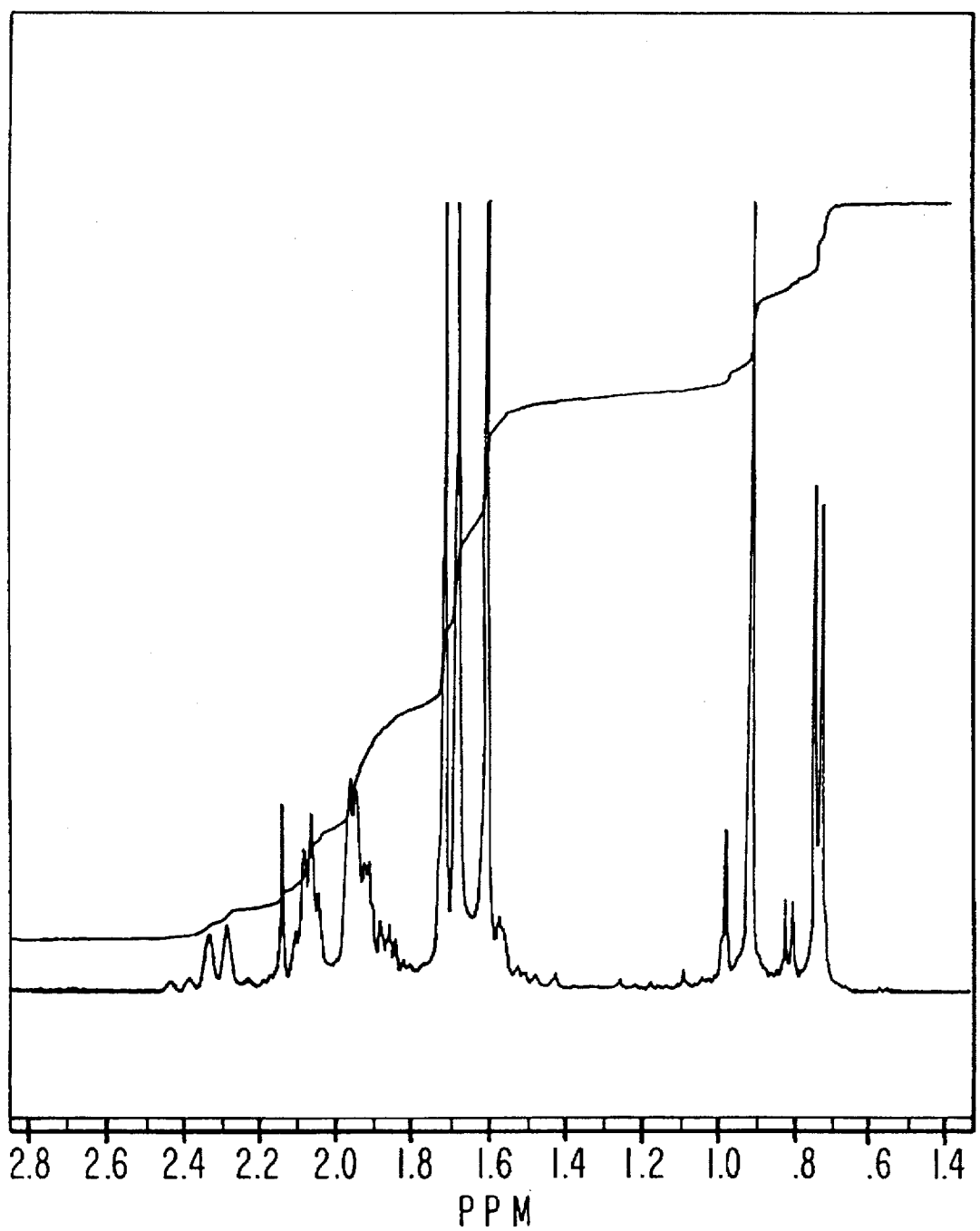
FIG. 20-A

FIG. 20-B
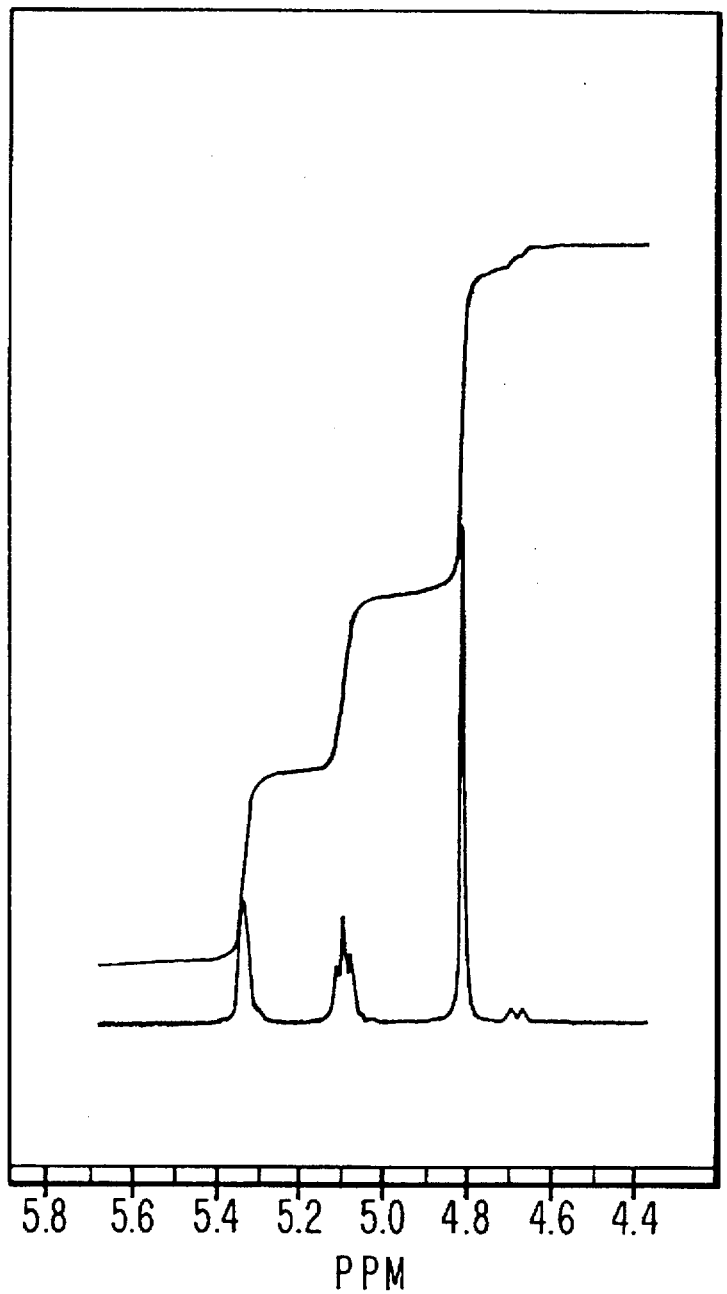

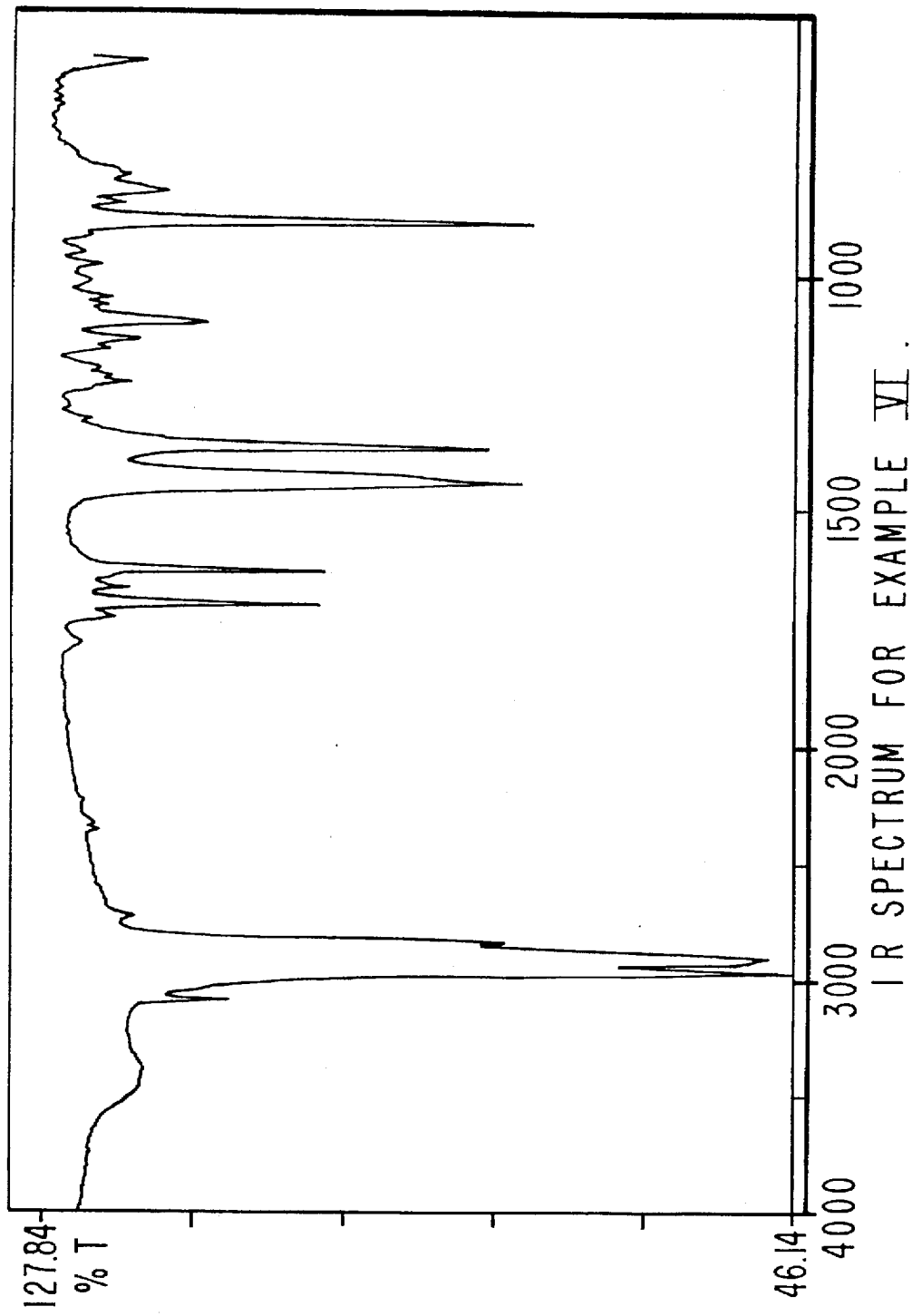
FIG. 21 IR SPECTRUM FOR EXAMPLE VI.

GLC PROFILE FOR EXAMPLE VII(A).

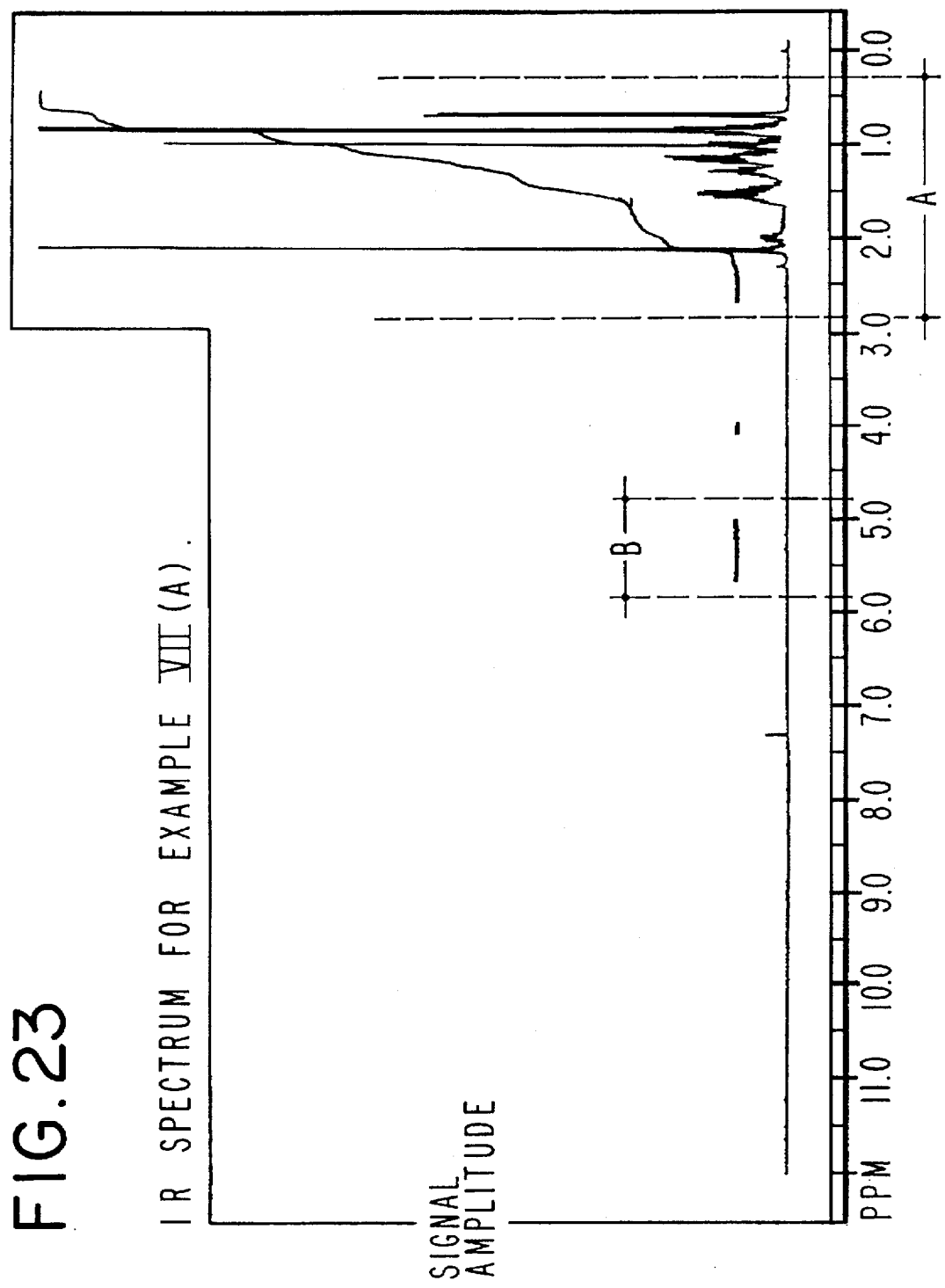
FIG. 23 IR SPECTRUM FOR EXAMPLE VII(A).

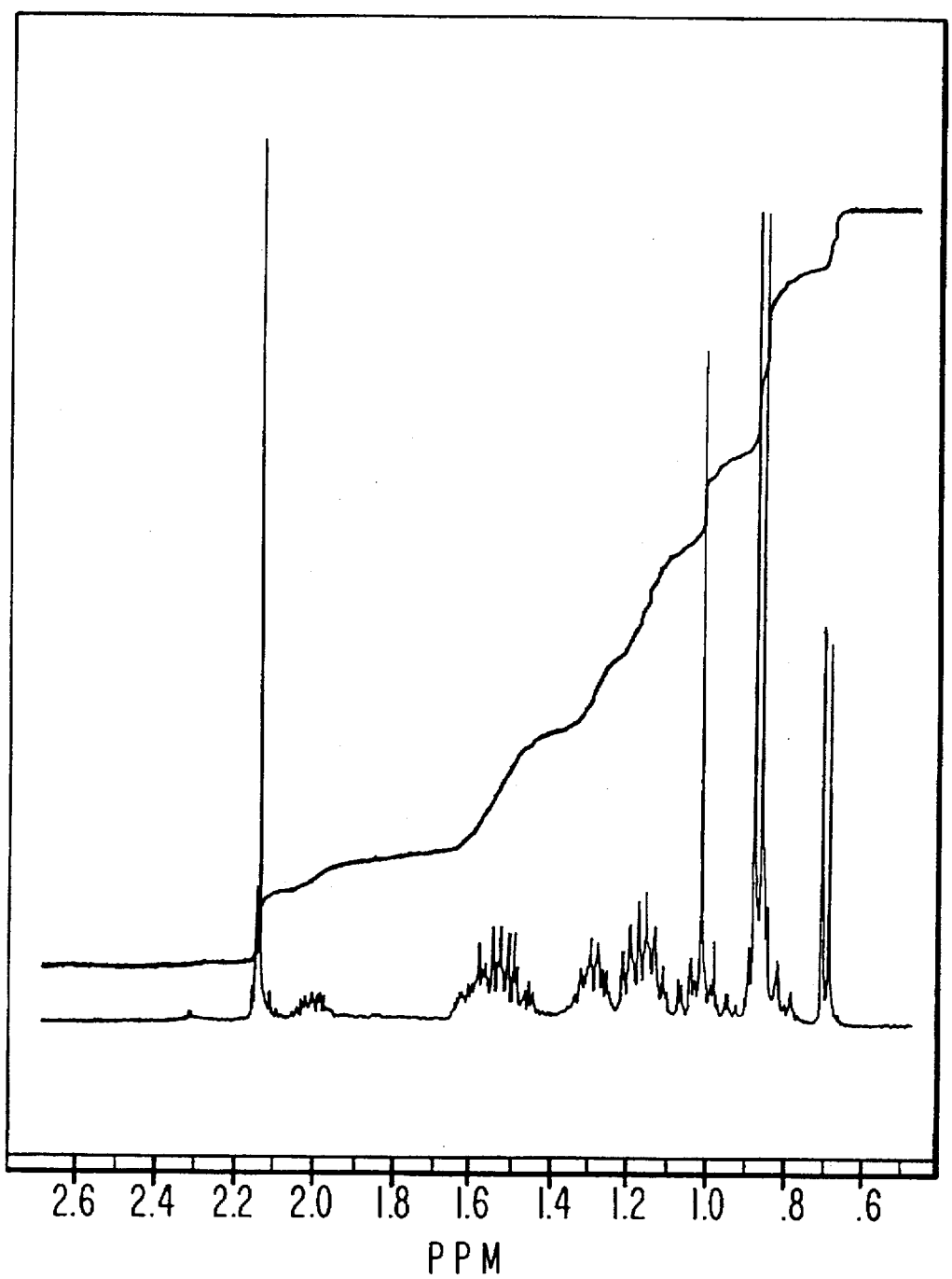
FIG. 23-A

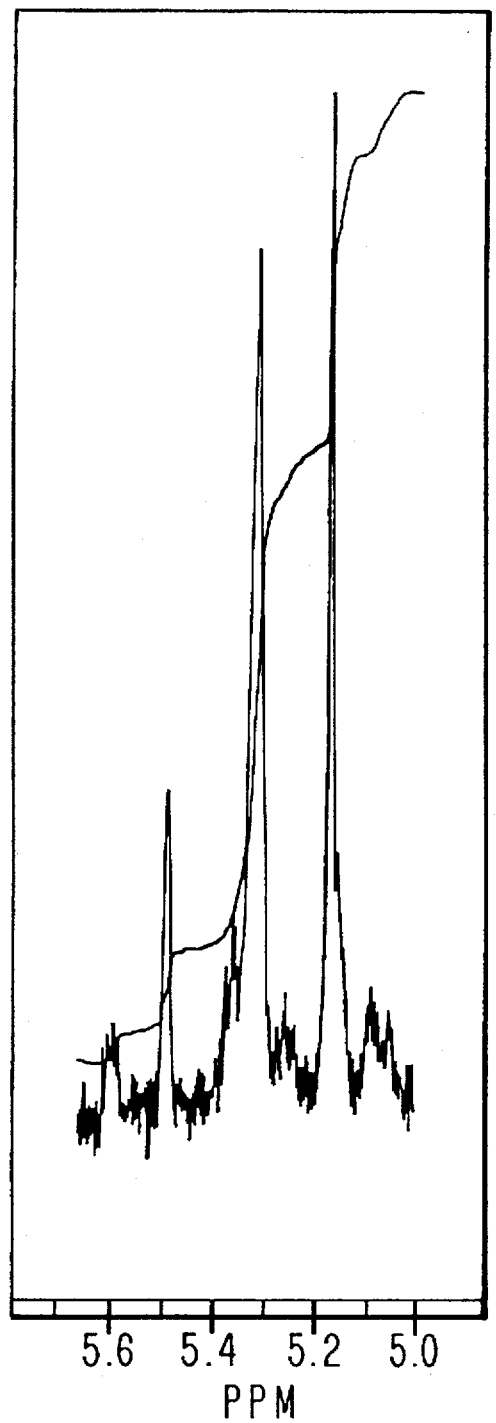
FIG.23-B

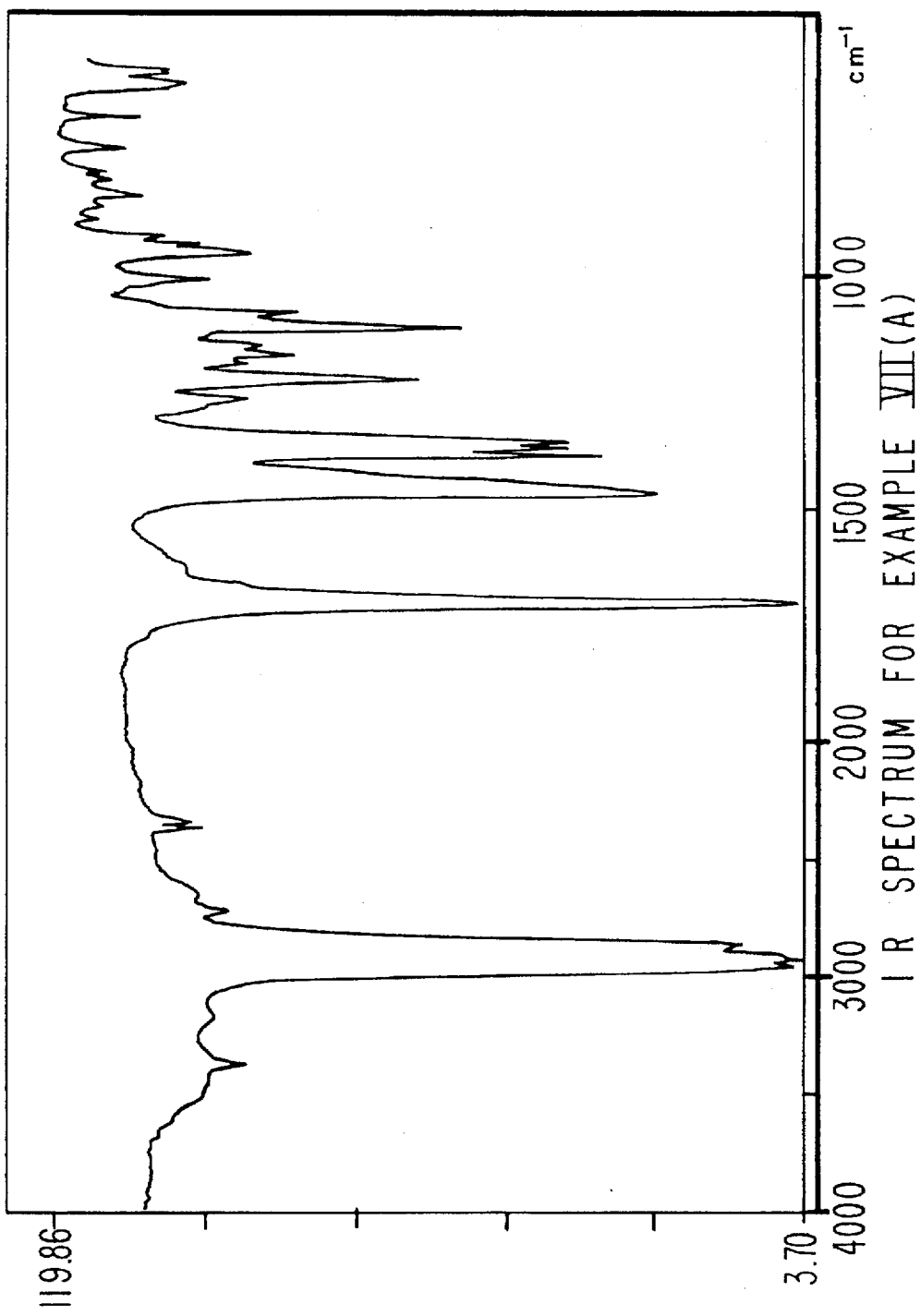

GLC PROFILE FOR EXAMPLE VII(B).

FIG. 26 NMR SPECTRUM FOR EXAMPLE VII(B).

GLC PROFILE FOR EXAMPLE VII(C).

FIG. 28 NMR SPECTRUM FOR EXAMPLE VII (C).

GLC PROFILE FOR EXAMPLE VIII.

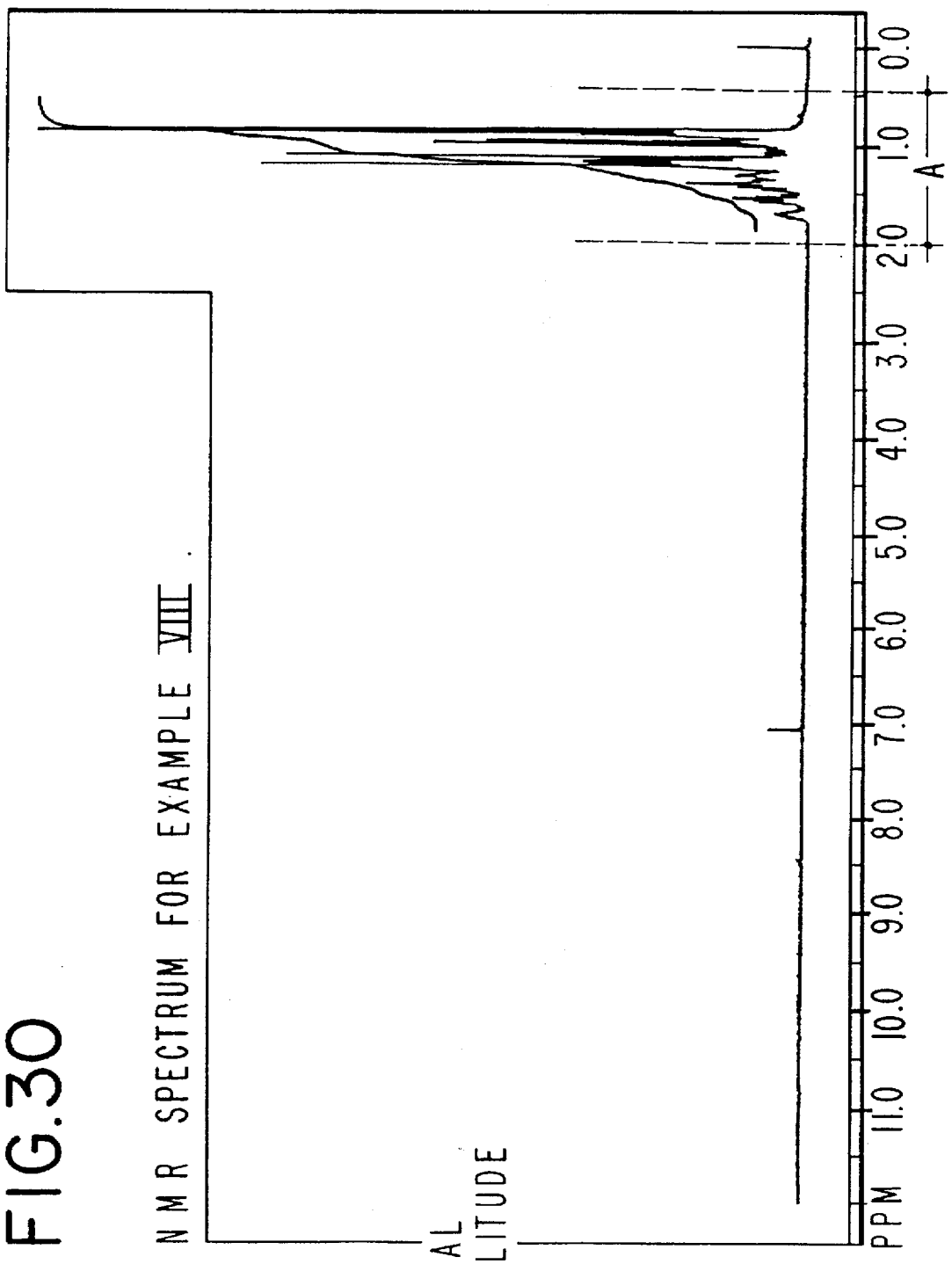
FIG. 30 NMR SPECTRUM FOR EXAMPLE VIII

FIG.30-A
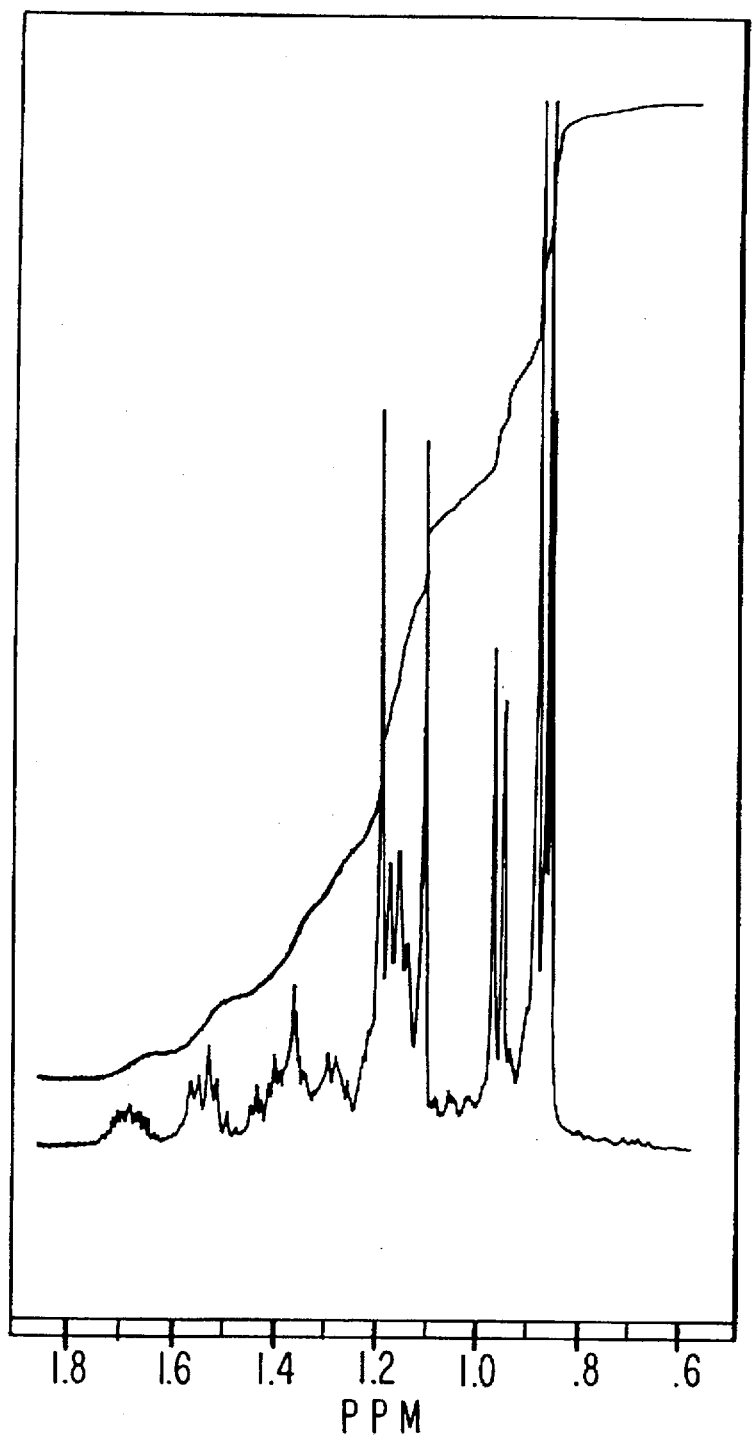

IR SPECTRUM FOR EXAMPLE VIII.

GLC PROFILE FOR EXAMPLE IX.

FIG. 33 NMR SPECTRUM FOR EXAMPLE IX

GLC PROFILE FOR EXAMPLE X.

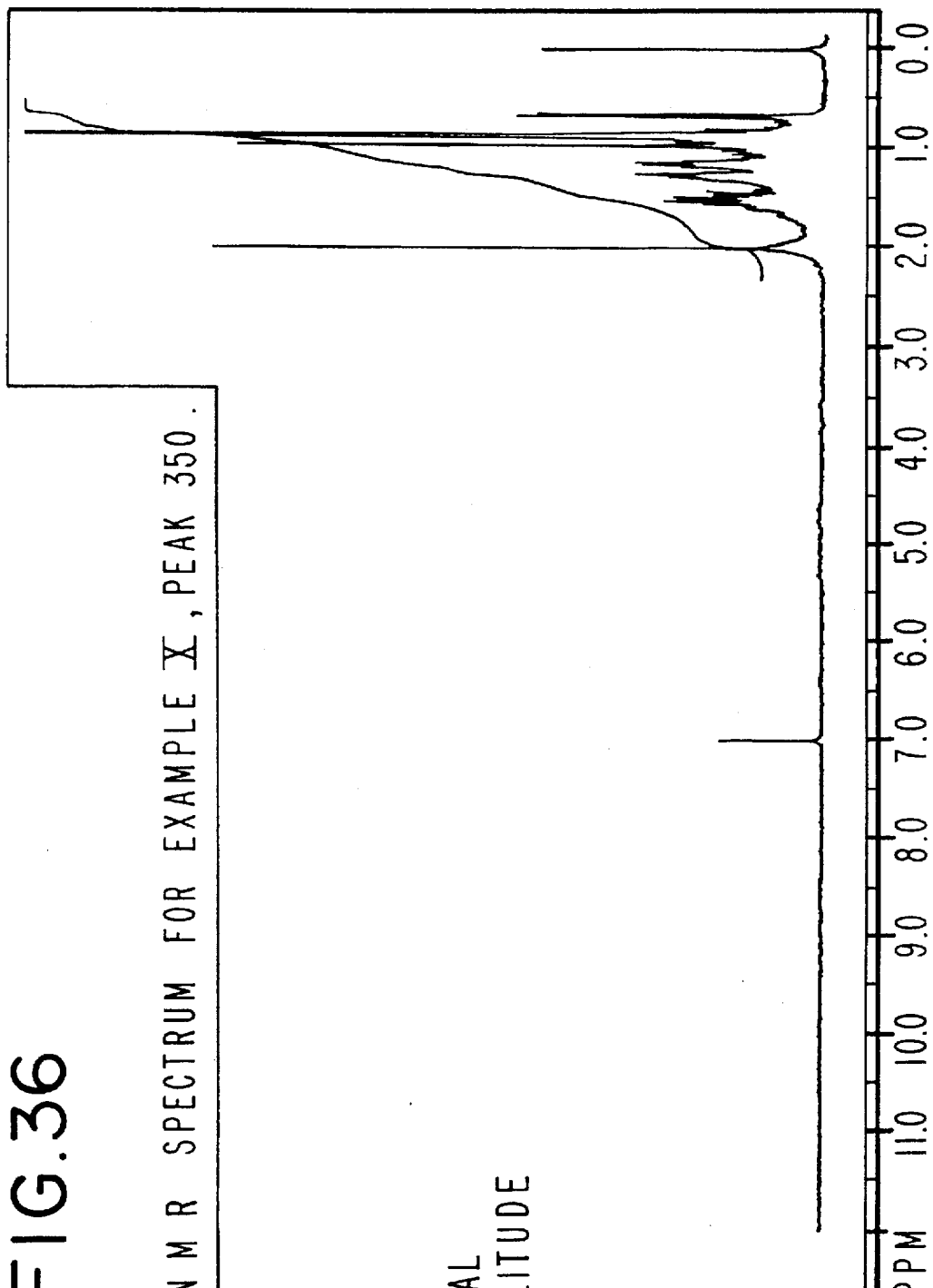
FIG.36 NMR SPECTRUM FOR EXAMPLE X, PEAK 350.

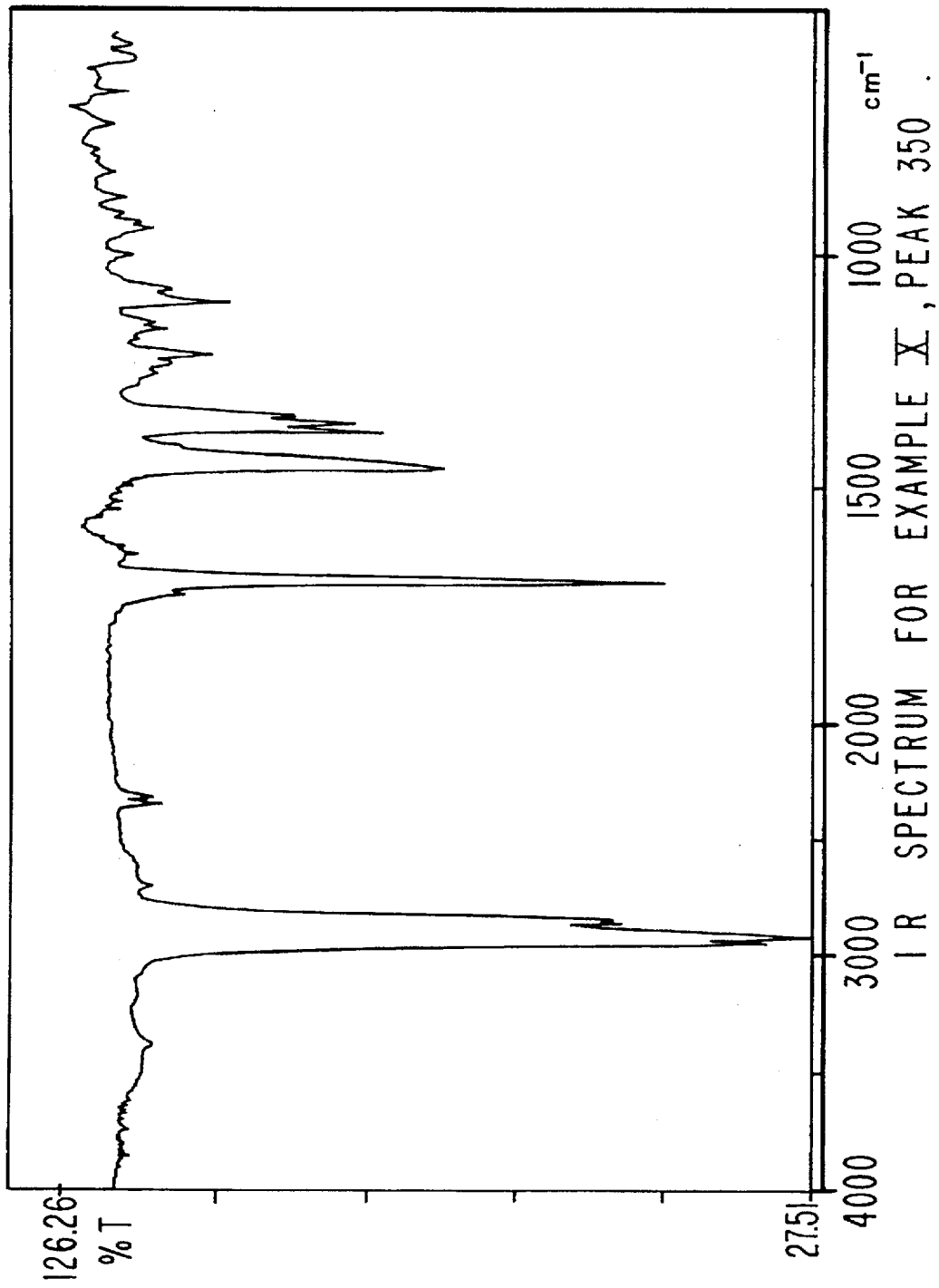

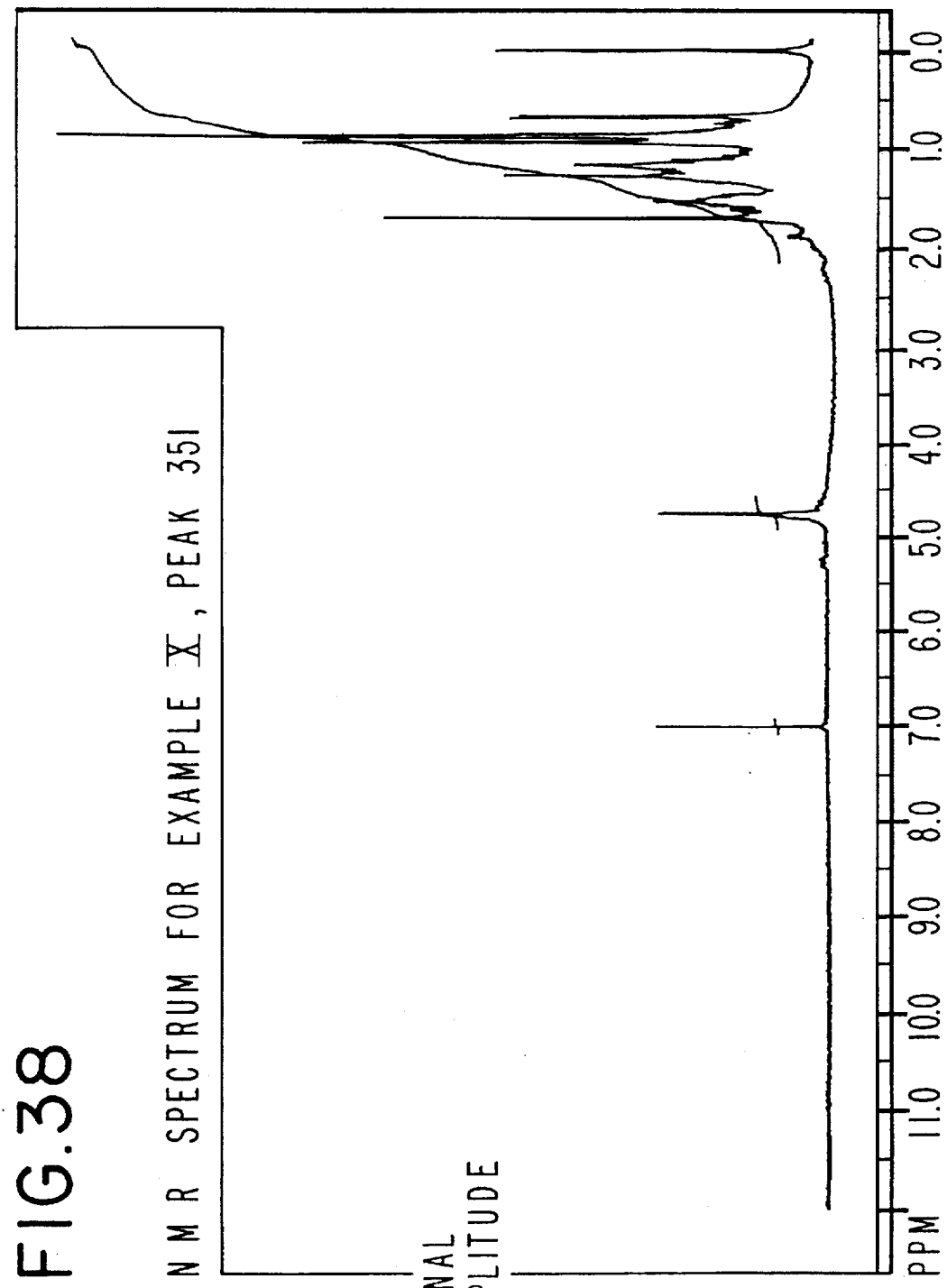
FIG. 38 NMR SPECTRUM FOR EXAMPLE X, PEAK 351

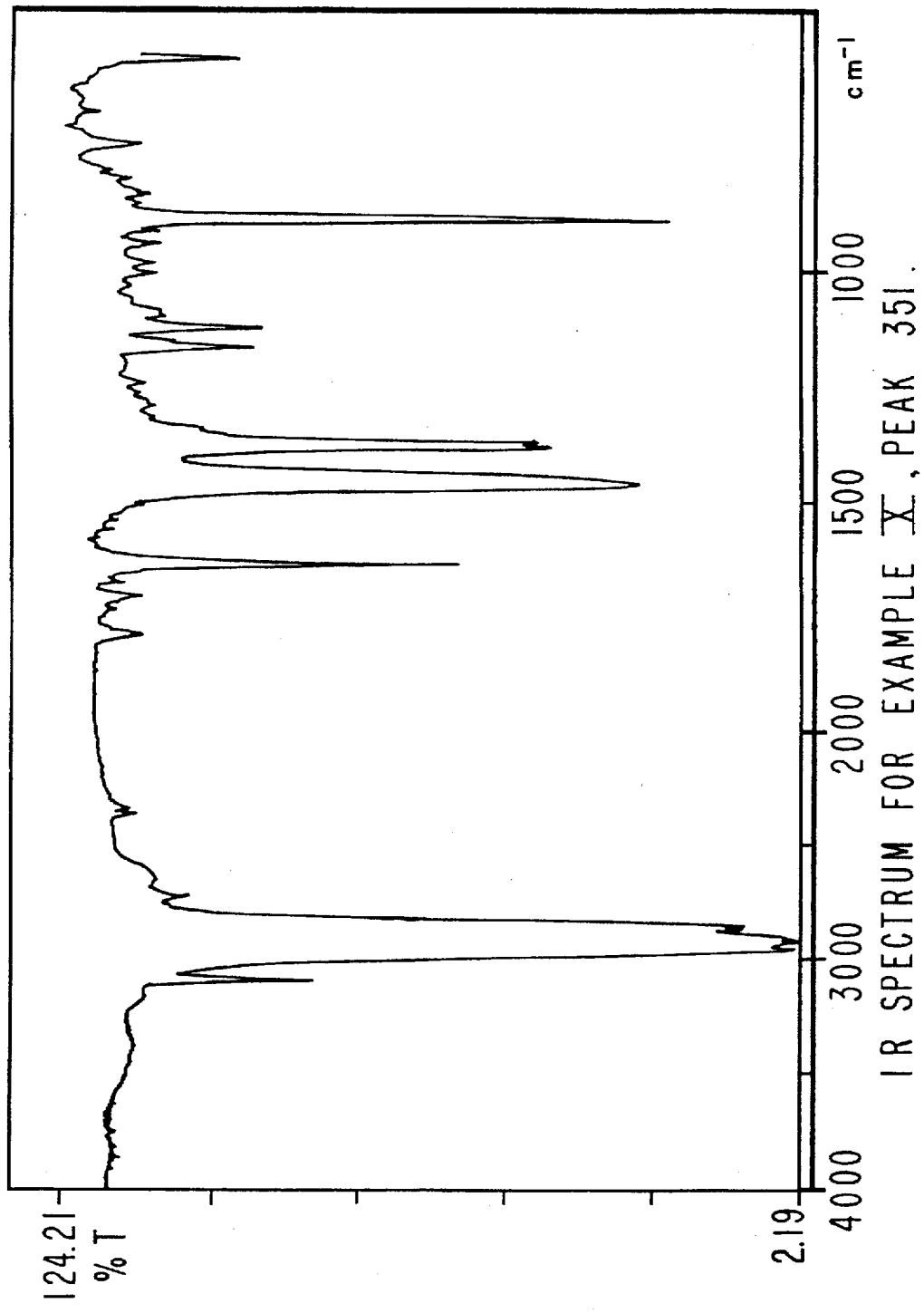

1(4'-METHYLPENTYL)-4-SUBSTITUTED ETHYLCYCLOHEXANE DERIVATIVES, ORGANOLEPTIC USES THEREOF, PROCESS FOR PRODUCING SAME, AND PROCESS INTERMEDIATES THEREFOR

BACKGROUND OF THE INVENTION

The present invention relates to 1(4'-methylpentyl)-4-substituted ethylcyclohexane derivatives defined according to the structure:

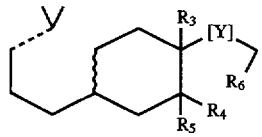

wherein $R_3$, $R_4$, $R_5$ and $R_6$ are the same or different hydrogen or methyl; wherein the dashed line represents a carbon carbon single bond or a carbon carbon double bond; wherein the wavy line represents a carbon carbon single bond or a carbon carbon double bond; with the proviso that when the wavy line is a carbon carbon single bond then the dashed line is a carbon carbon single bond; wherein Y is a moiety selected from the group consisting of:

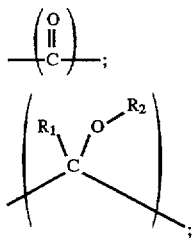

and

-continued

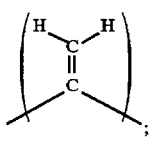

wherein $R_2$ represents hydrogen, $C_1-C_4$ lower alkyl or $C_1-C_2$ acyl; and wherein $R_1$ represents $C_1-C_4$ lower alkyl with the additional proviso that when Y is the moiety:

then the dashed line is a carbon carbon single bond, and uses thereof in augmenting, enhancing or imparting aromas in or to perfume compositions, colognes and perfumed articles (including solid or liquid anionic, cationic, nonionic or zwitterionic detergents, fabric softener compositions, fabric softener articles, cosmetic powders, hair preparations and perfumed polymers).

There has been considerable work performed relating to substances which can be used to impart (augment or enhance) fragrances (to) or (in) various consumable materials. These substances are used to diminish the use of natural materials some of which may be in short supply and to provide more uniform products in the finished product. In addition, there is a need to use such consumable materials in perfumes which are non-discoloring.

Intense, substantive and long lasting patchouli, ambery, earthy, woody, peach, mimosa, camphoraceous, mahogany, piney, animalic and musky aromas with patchouli, camphoraceous, earthy; musty, woody, green and fruity topnotes are highly desirable for many uses in perfume compositions, perfumed articles and colognes, particularly where a patchouli note is needed to be added to musk formulations and citrusy formulations.

Substituted ethylcyclohexane derivatives are well known for use in perfumery. Thus, British Patent No. 896,039 entitled "Method of Producing Derivatives of the 1,1-Dimethyloctahydronaphthalene Series" discloses the generic process:

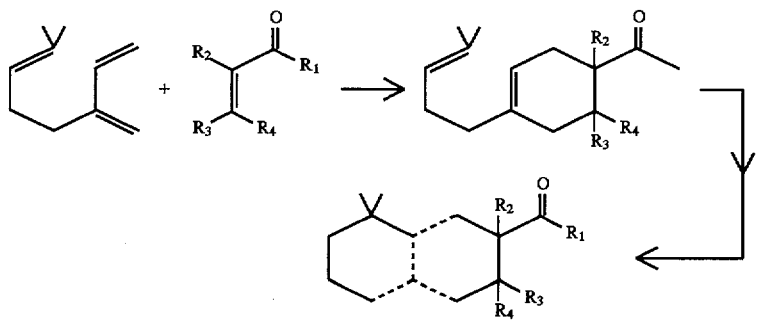

wherein $R_2$, $R_3$ and $R_4$ are disclosed to be the same or different hydrogen atoms or alkyl and $R_1$ is disclosed to be hydroxy, alkyl or alkoxy, and wherein one of the dashed lines represents a carbon carbon double bond and each of the other of the dashed lines represent carbon carbon single bonds. British Patent No. 896,039 discloses this process to be useful for producing products "resembling the well known class of violet perfumes". However, nothing in British Patent Specification No. 896,039 discloses or implies the 1(4'-methylpentyl)-4-substituted ethylcyclohexane derivatives of our invention.

BRIEF DESCRIPTION OF THE DRAWINGS

FIG. 1A is the GC-MS spectrum for the reaction product of Example A containing the compound having the structure:

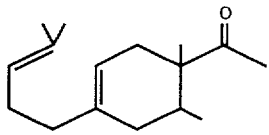

(conditions: 50 meter×0.32 mm methyl silicone column programmed from 75°–225° C. at 2° C. per minute).

FIG. 1B is the GC-MS spectrum for the reaction product of Example A containing the compound having the structure:

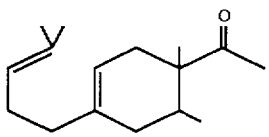

(conditions: 50 meter×0.32 mm CARBOWAX® 20M column programmed from 75°–225° C. at 2° C. per minute).

FIG. 2 is the NMR spectrum for the compound having the structure:

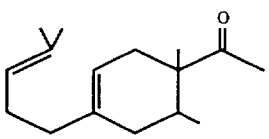

produced according to Example A.

FIG. 2A is an enlargement of section "A" of the NMR spectrum of FIG. 2.

FIG. 2B is an enlargement of section "B" of the NMR spectrum of FIG. 2.

FIG. 3 is the IR spectrum for the compound having the structure:

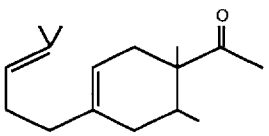

prepared according to Example A.

Figure 4:
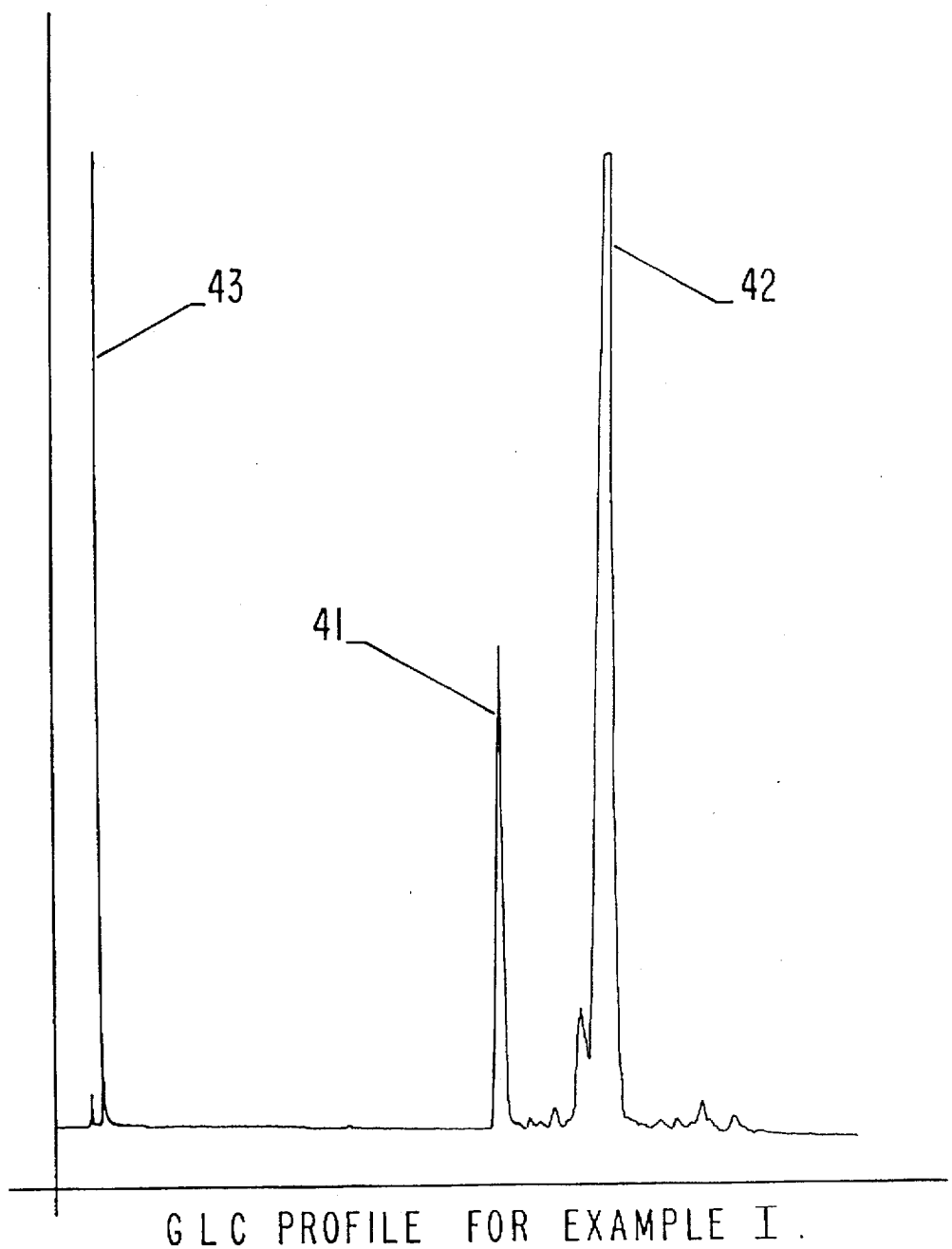

FIG. 4 is the GLC profile for the reaction product of Example I containing the compound having the structure:

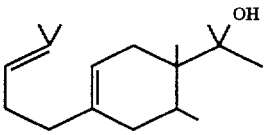

(conditions: SE-30 column programmed from 150°–220° C. at 8° C. per minute).

FIG. 5 is the NMR spectrum for the compound having the structure:

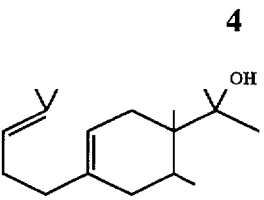

prepared according to Example I.

FIG. 5A is an enlargement of section "A" of the NMR spectrum of FIG. 5.

FIG. 5B is an enlargement of section "B" of the NMR spectrum of FIG. 5.

FIG. 6 is the infrared spectrum for the compound having the structure:

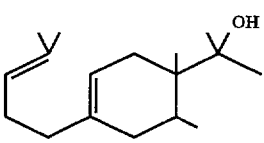

prepared according to Example I.

Figure 7:
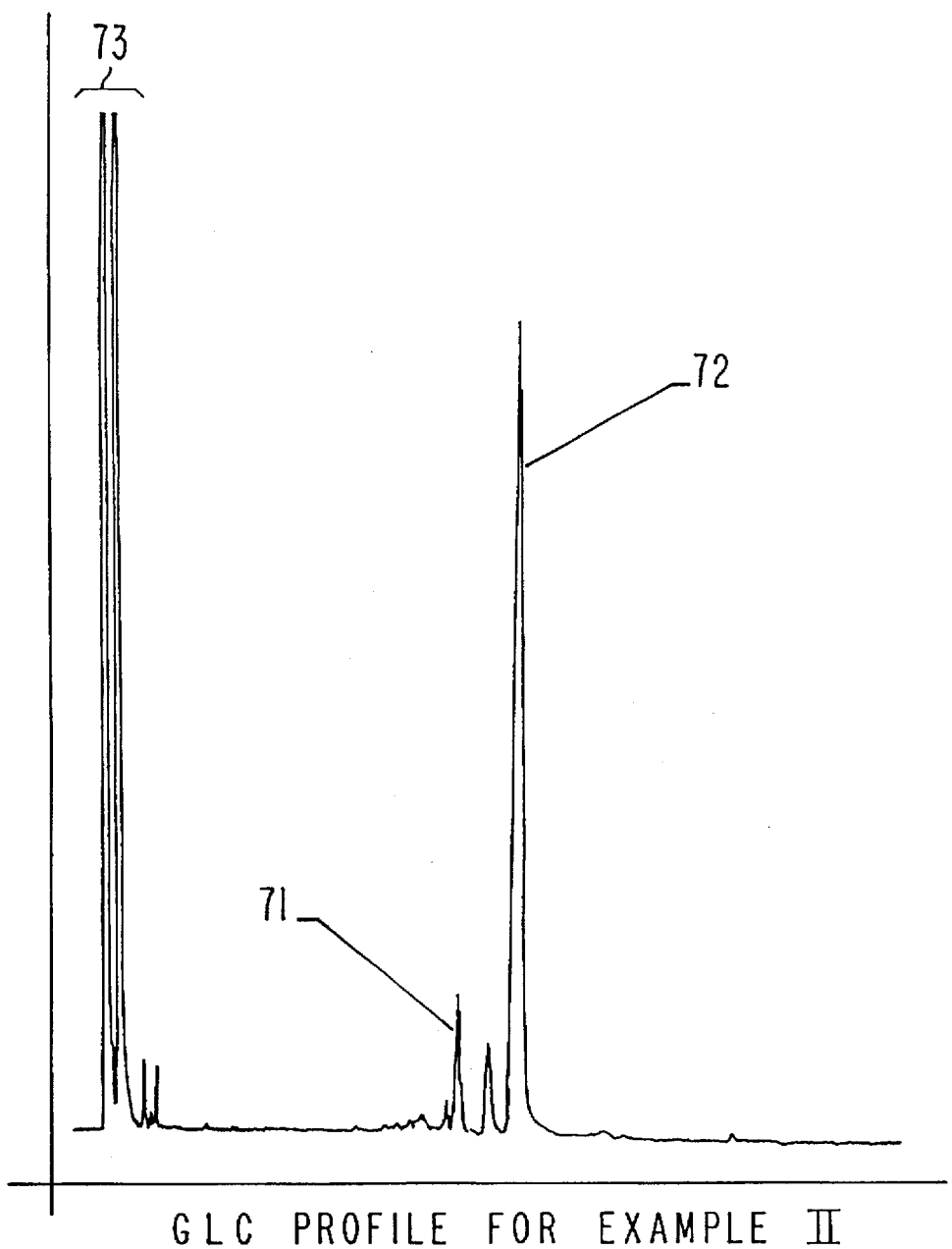

FIG. 7 is the GLC profile for the reaction product of Example II containing the compound having the structure:

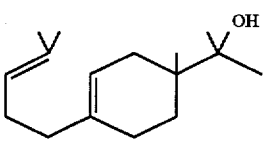

(conditions: SE-30 column programmed from 150°–220° C. at 8° C. per minute).

FIG. 8 is the NMR spectrum for the compound having the structure:

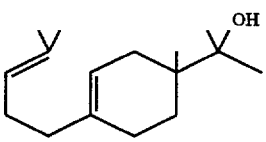

prepared according to Example II.

FIG. 8A is an enlargement of section "A" of the NMR spectrum of FIG. 8.

FIG. 8B is an enlargement of section "B" of the NMR spectrum of FIG. 8.

FIG. 9 is the infrared spectrum for the compound having the structure:

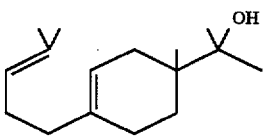

prepared according to Example II.

Figure 10:
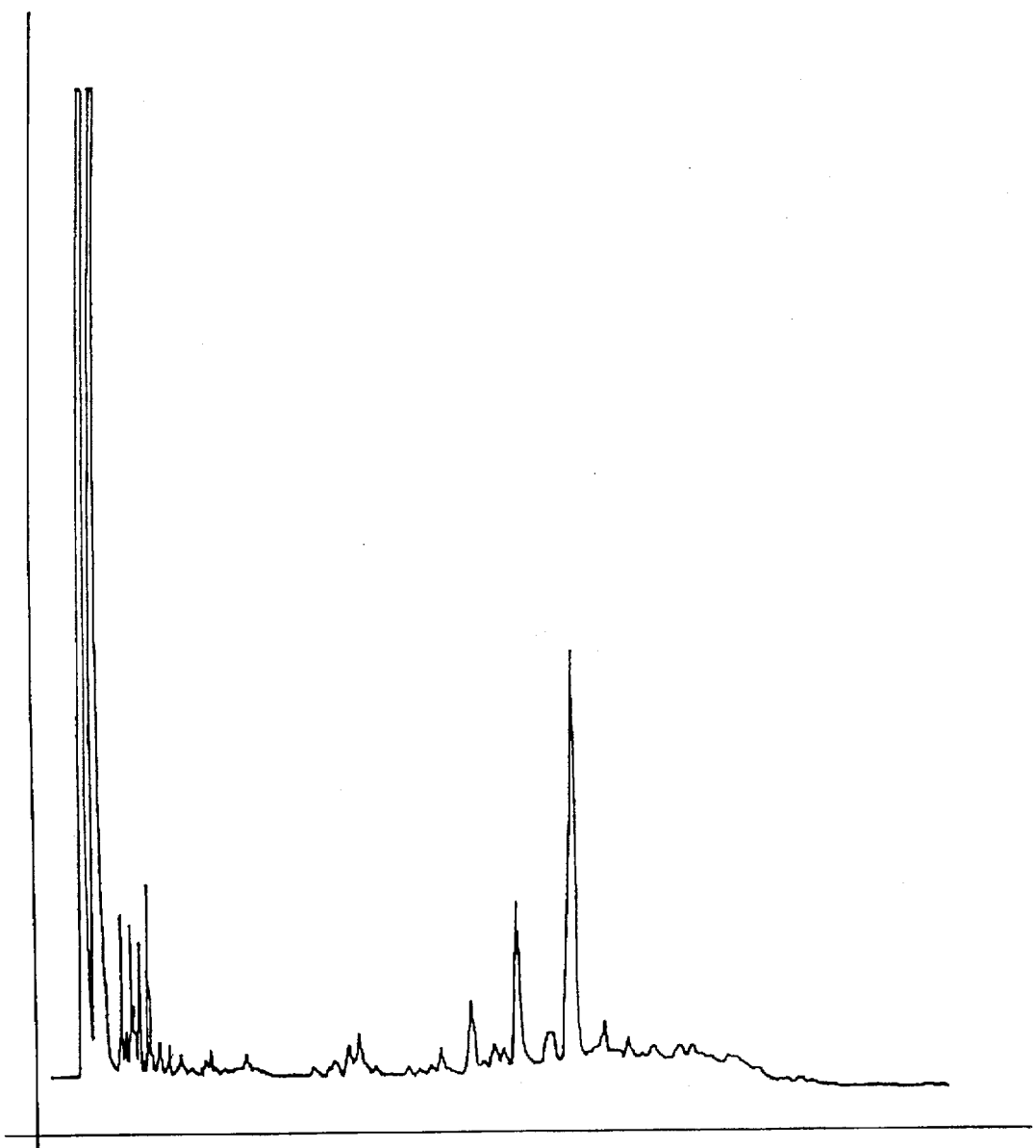
Figure 11:
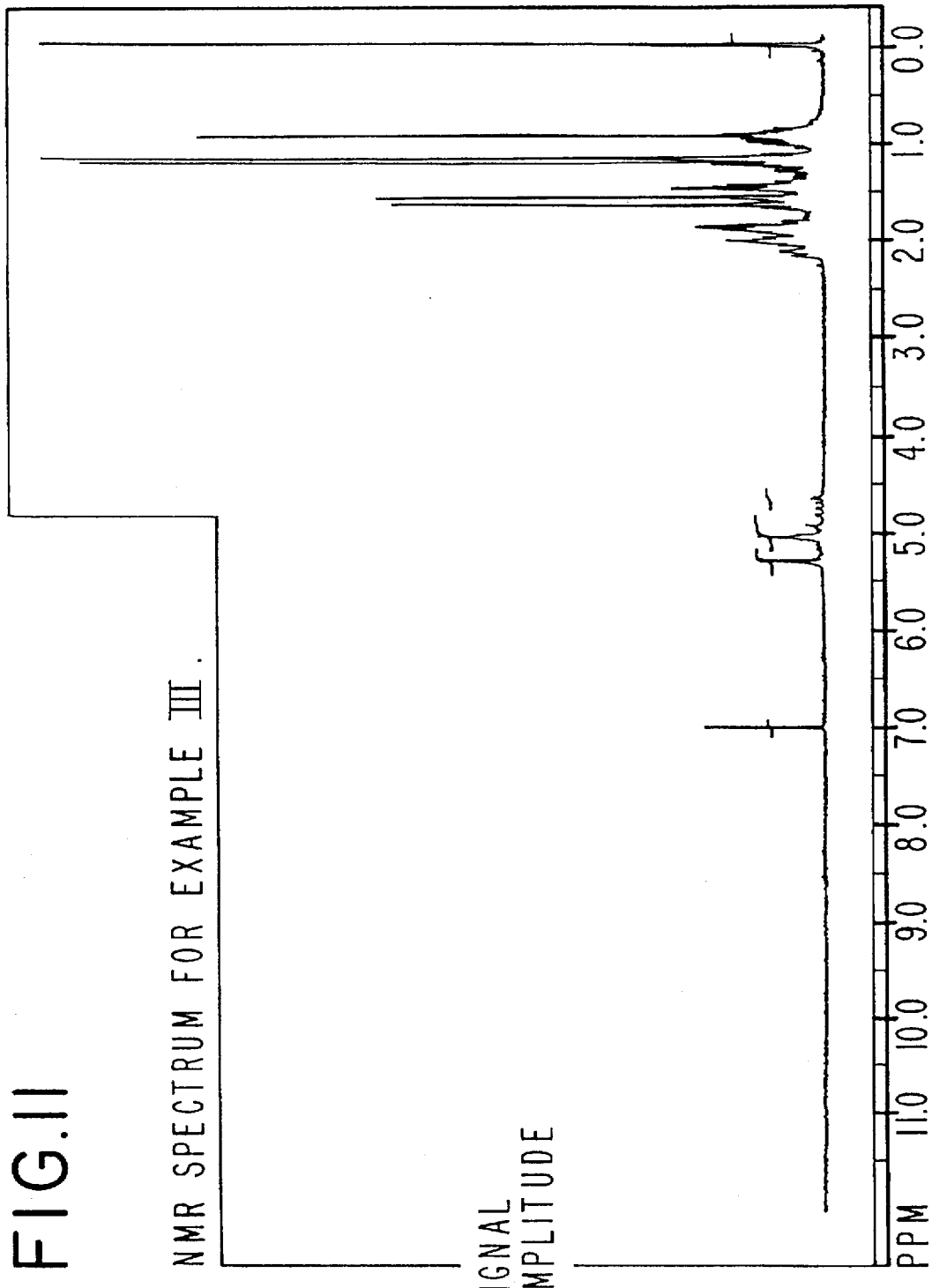

FIG. 10 is the GLC profile for the reaction product of Example III containing the compound having the structure:

FIG. 11 is the NMR spectrum for the compound having the structure:

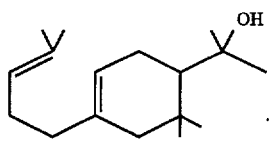

prepared according to Example III.

Figure 12:
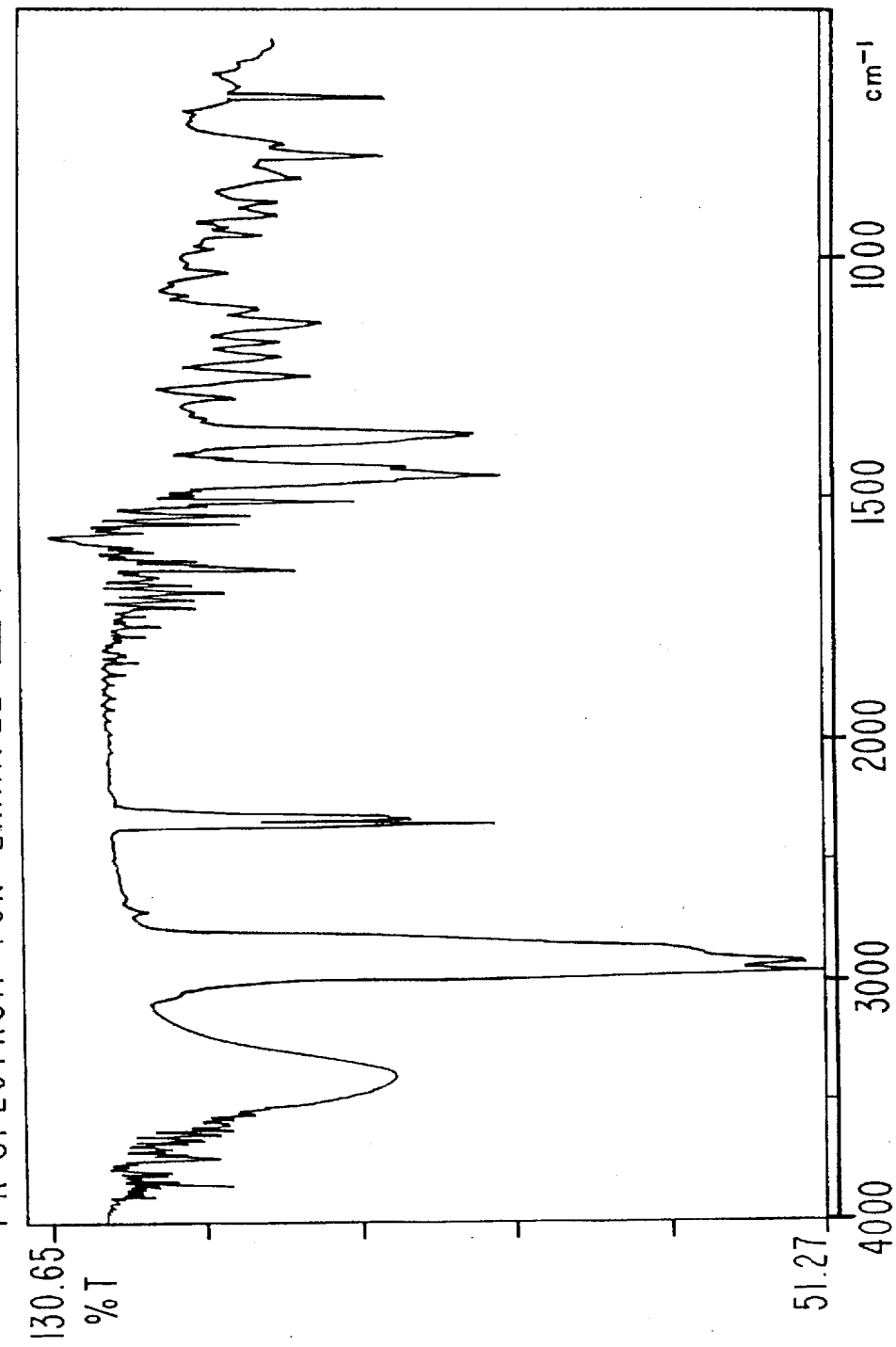

FIG. 12 is the infrared spectrum for the compound having the structure:

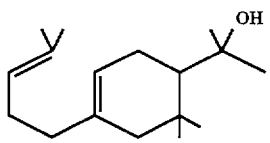

prepared according to Example III.

Figure 13:
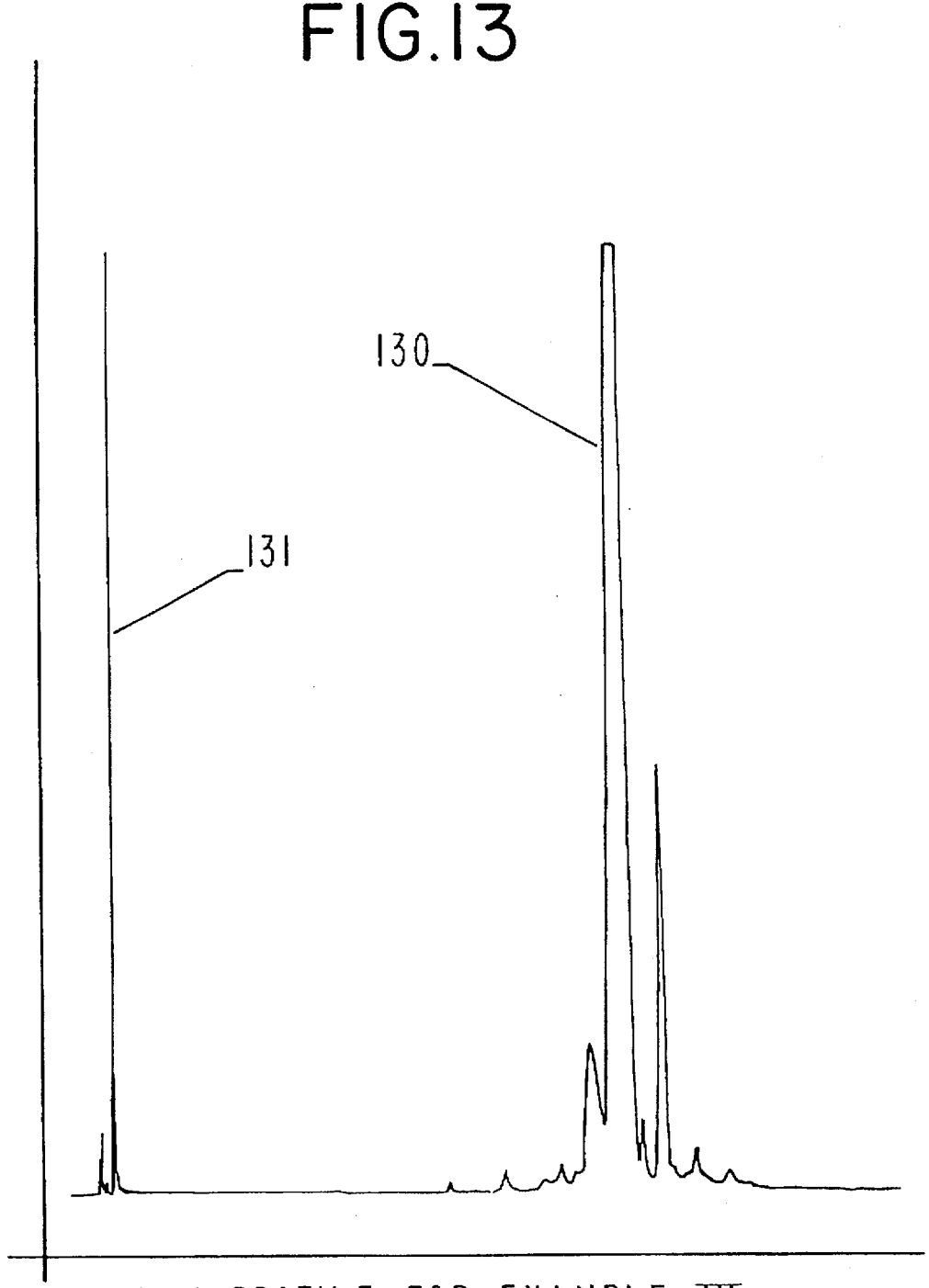

FIG. 13 is the GLC profile for the reaction product of Example IV containing the compound having the structure:

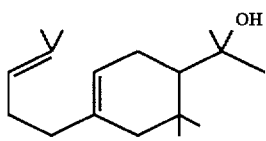

(conditions: SE-30 column programmed from 150°–220° C. at 8° C. per minute).

FIG. 14 is the NMR spectrum for the compound having the structure:

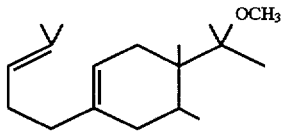

prepared according to Example IV.

FIG. 14A is an enlargement of section "A" of the NMR spectrum of FIG. 14.

FIG. 14B is an enlargement of section "B" of the NMR spectrum of FIG. 14.

FIG. 14C is an enlargement of section "C" of the NMR spectrum of FIG. 14.

FIG. 15 is the infrared spectrum for the compound having the structure:

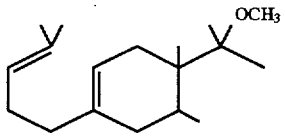

prepared according to Example IV.

Figure 16:
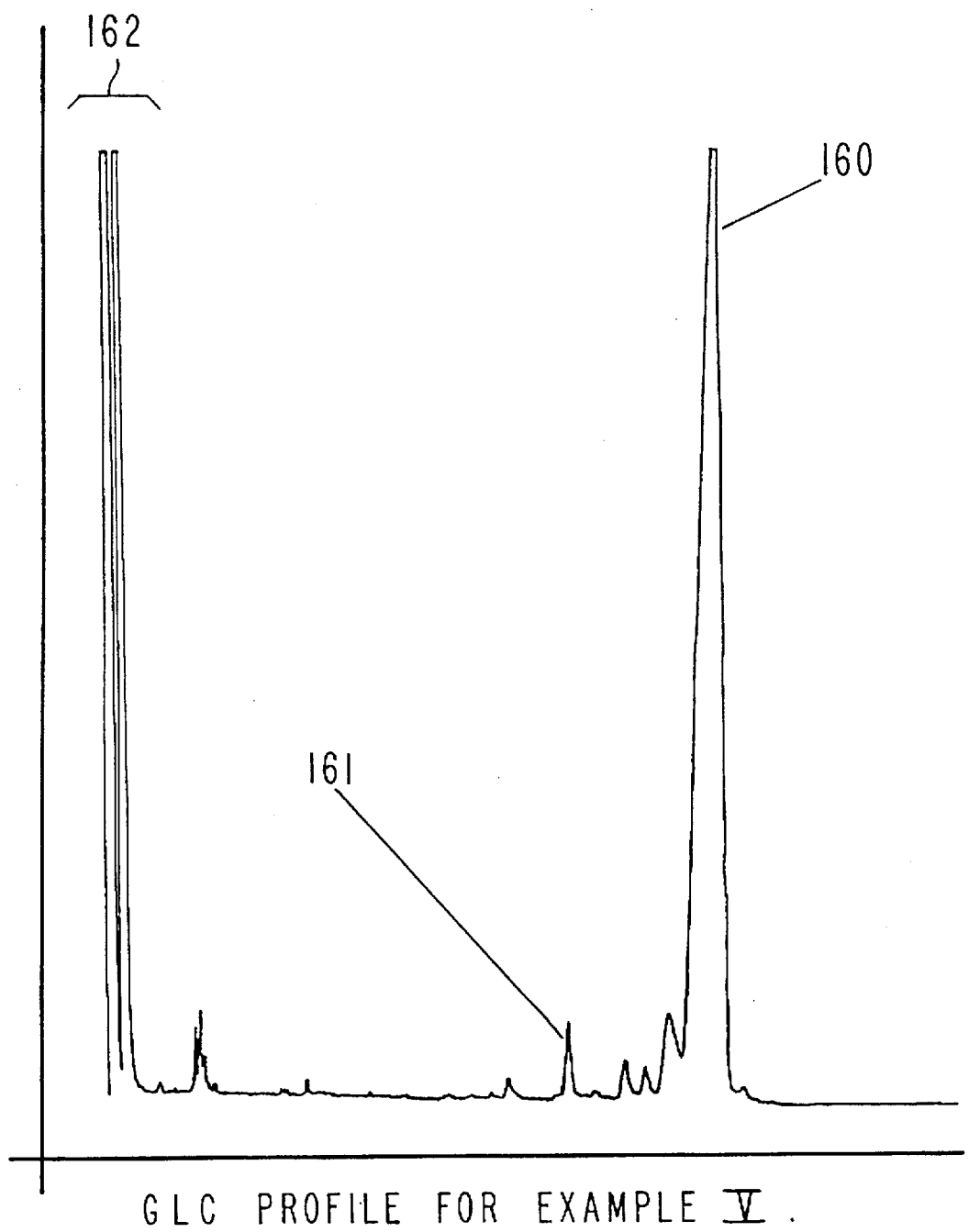

FIG. 16 is the GLC profile for the reaction product of Example V containing the compound having the structure:

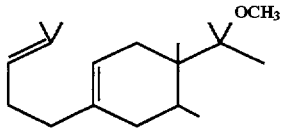

(conditions: SE-30 column programmed from 150°–220° C. at 8° C. per minute).

FIG. 17 is the NMR spectrum for the compound having the structure:

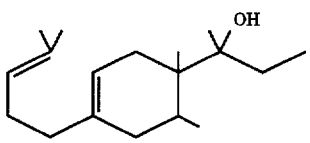

prepared according to Example V.

FIG. 17A is an enlargement of section "A" of the NMR spectrum of FIG. 17.

FIG. 17B is an enlargement of section "B" of the NMR spectrum of FIG. 17.

FIG. 18 is the infrared spectrum for the compound having the structure:

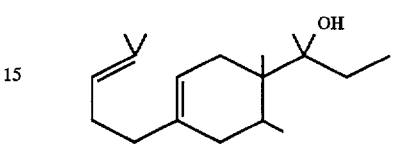

prepared according to Example V.

Figure 19:
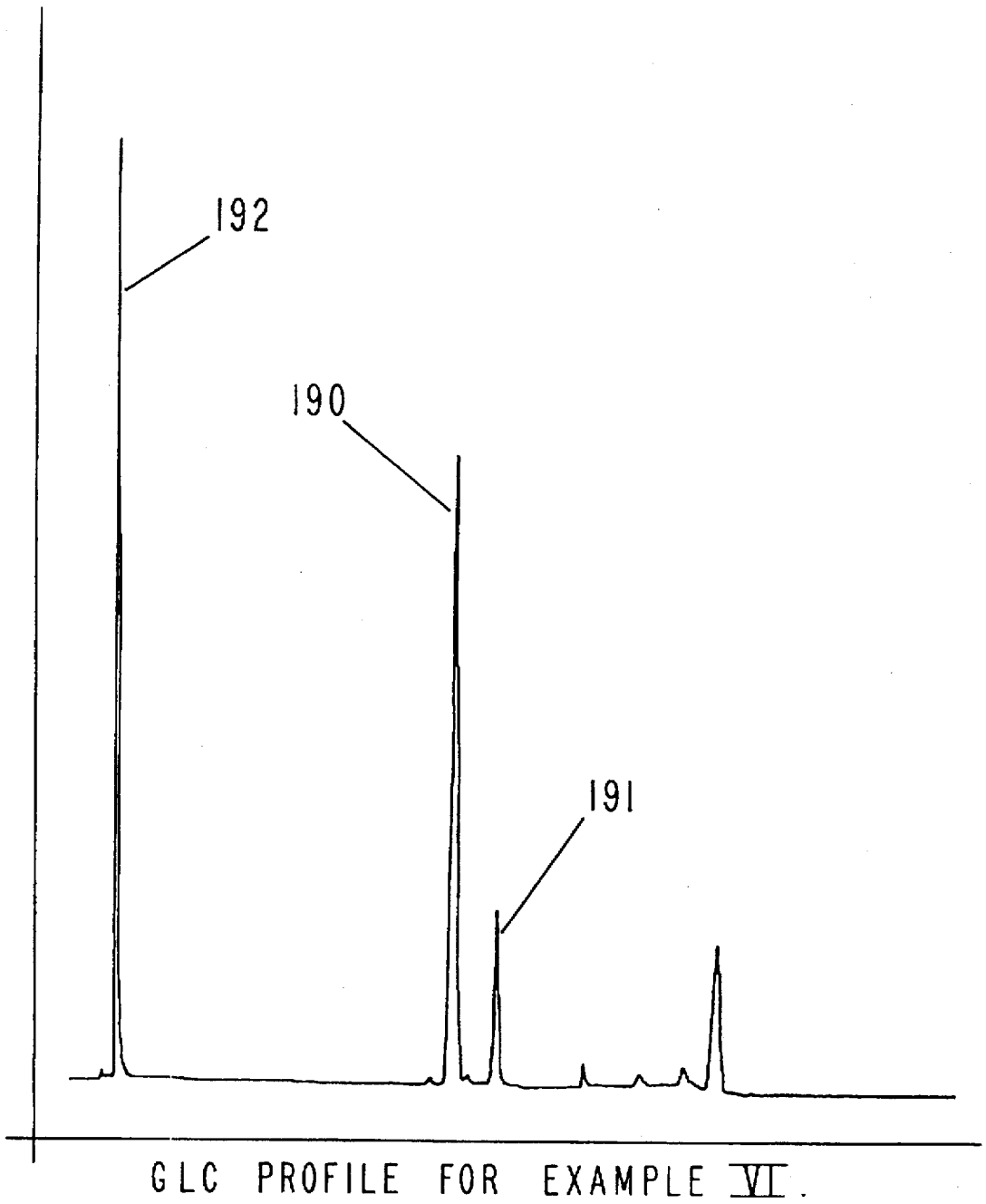

FIG. 19 is the GLC profile for the reaction product of Example VI containing the compound having the structure:

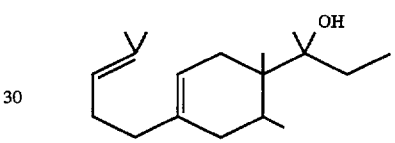

(conditions: SE-30 column programmed from 150°–220° C. at 8° C. per minute).

FIG. 20 is the NMR spectrum for the mixture of compounds containing 95 mole percent of the compound having the structure:

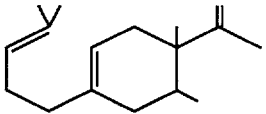

and 5 mole percent of the compound having the structure:

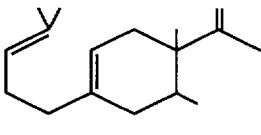

prepared according to Example VI.

FIG. 20A is an enlargement of section "A" of the NMR spectrum of FIG. 20.

FIG. 20B is an enlargement of section "B" of the NMR spectrum of FIG. 20.

FIG. 21 is the infrared spectrum for the mixture containing 95 mole percent of the compound having the structure:

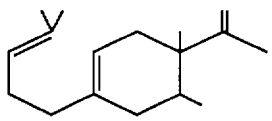

and 5 mole percent of the compound having the structure:

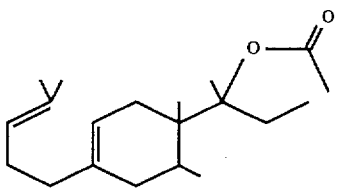

prepared according to Example VI.

Figure 22:
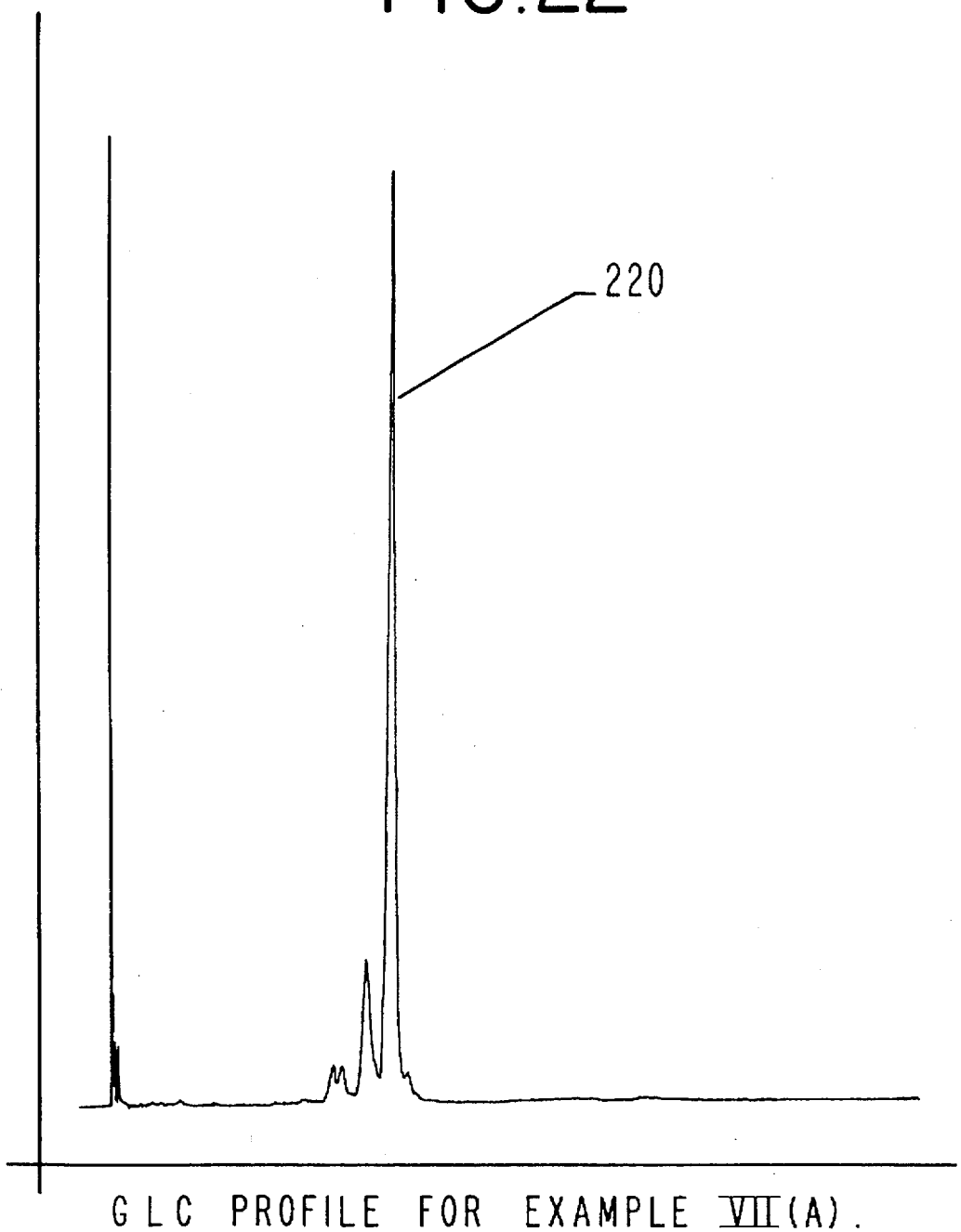

FIG. 22 is the GLC profile for the reaction product of Example VII(A) containing the compound having the structure:

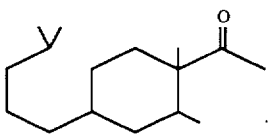

FIG. 23 is the NMR spectrum for the compound having the structure:

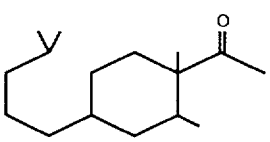

prepared according to Example VII(A).

FIG. 23A is an enlargement of section "A" of the NMR spectrum of FIG. 23.

FIG. 23B is an enlargement of section "B" of the NMR spectrum of FIG. 23.

FIG. 24 is the infrared spectrum for the compound having the structure:

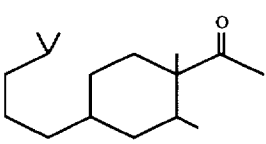

prepared according to Example VII(A).

Figure 25:
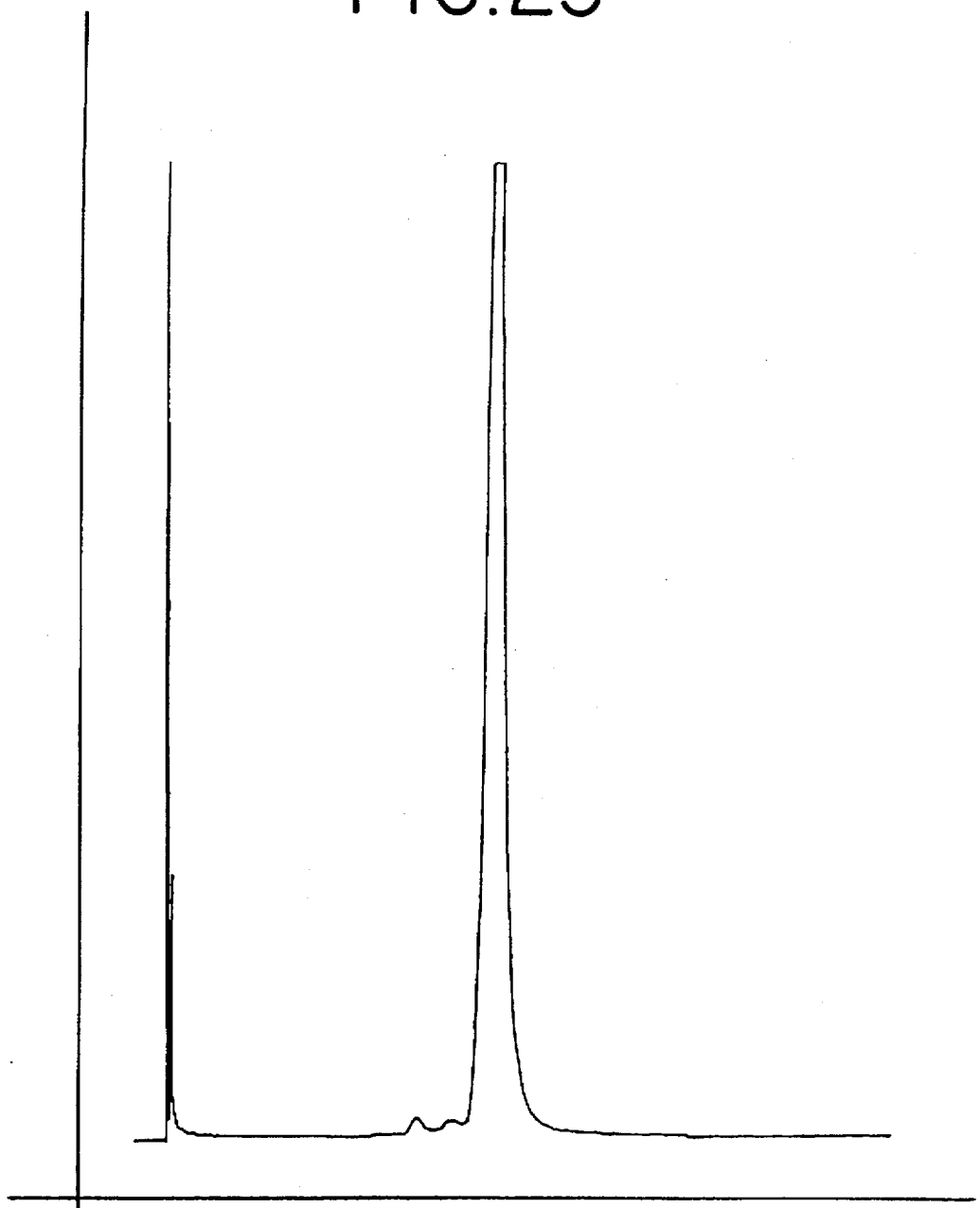

FIG. 25 is the GLC profile for the reaction product of Example VII (B) containing the compounds having the structures:

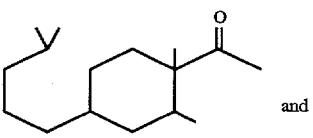

and

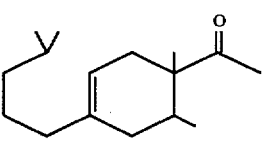

Figure 26:
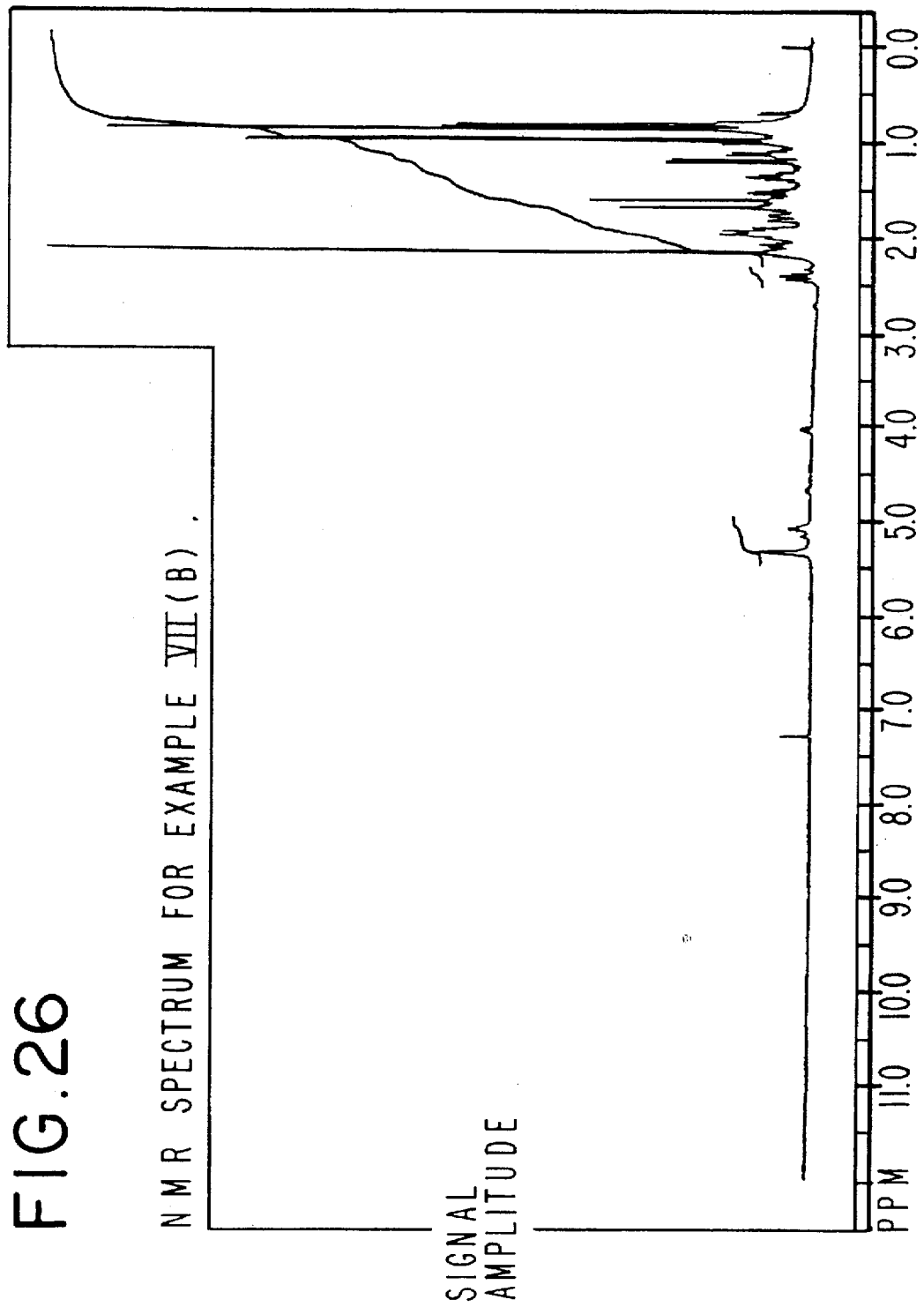

(conditions: CARBOWAX® 20M column programmed from 150°–220° C. at 8° C. per minute FIG. 26 is the NMR spectrum for the mixture of compounds having the structures:

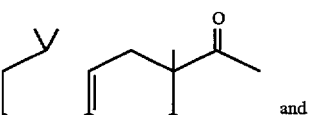

and

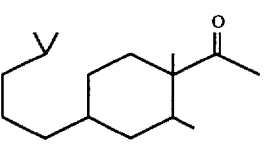

prepared according to Example VII(B)

Figure 27:
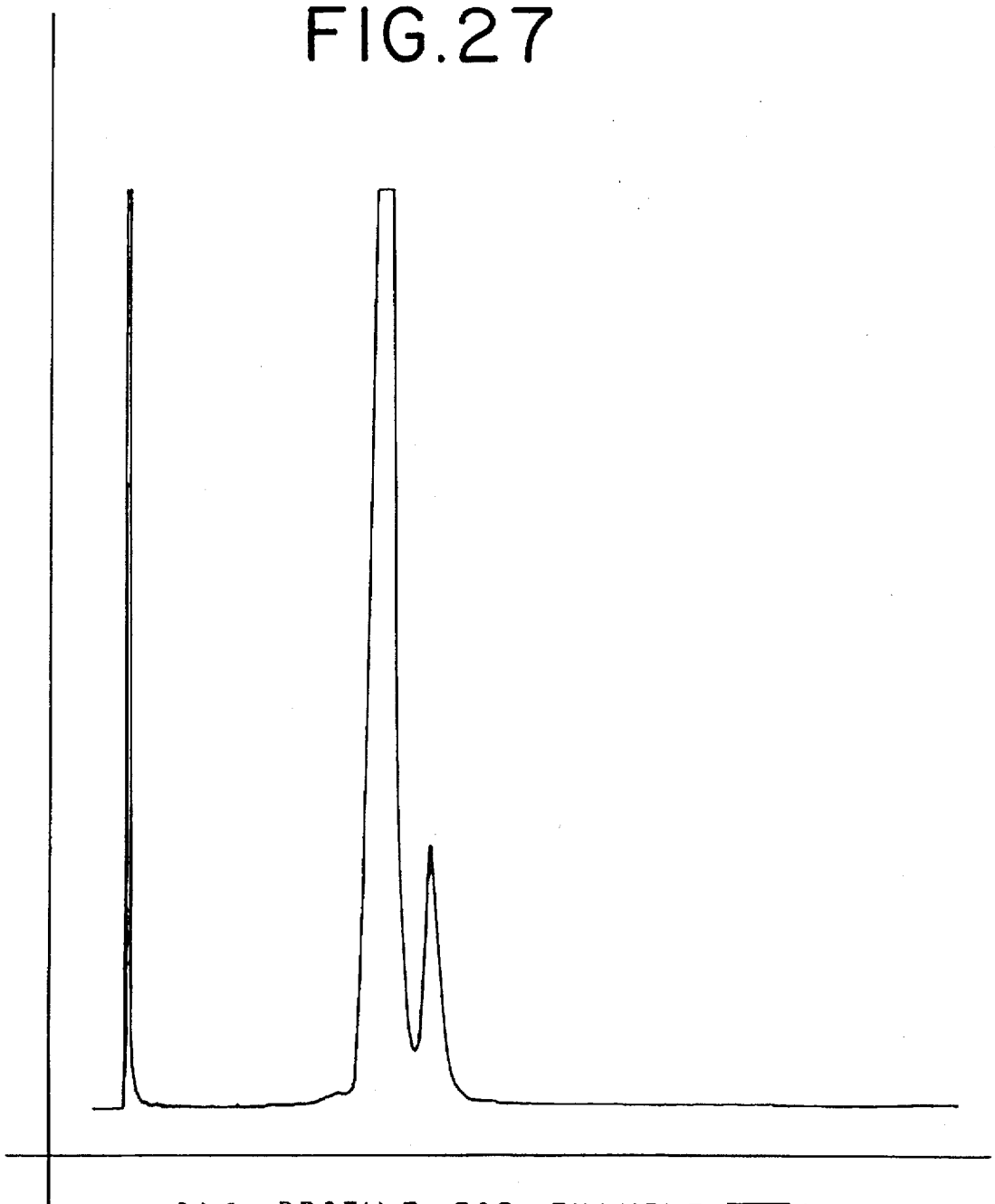

FIG. 27 is the GLC profile for the reaction product of Example VII(C) containing the compounds having the structures:

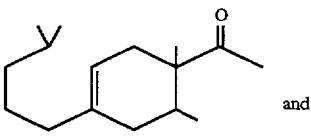

and

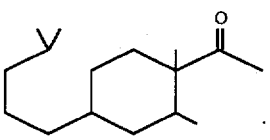

Figure 28:
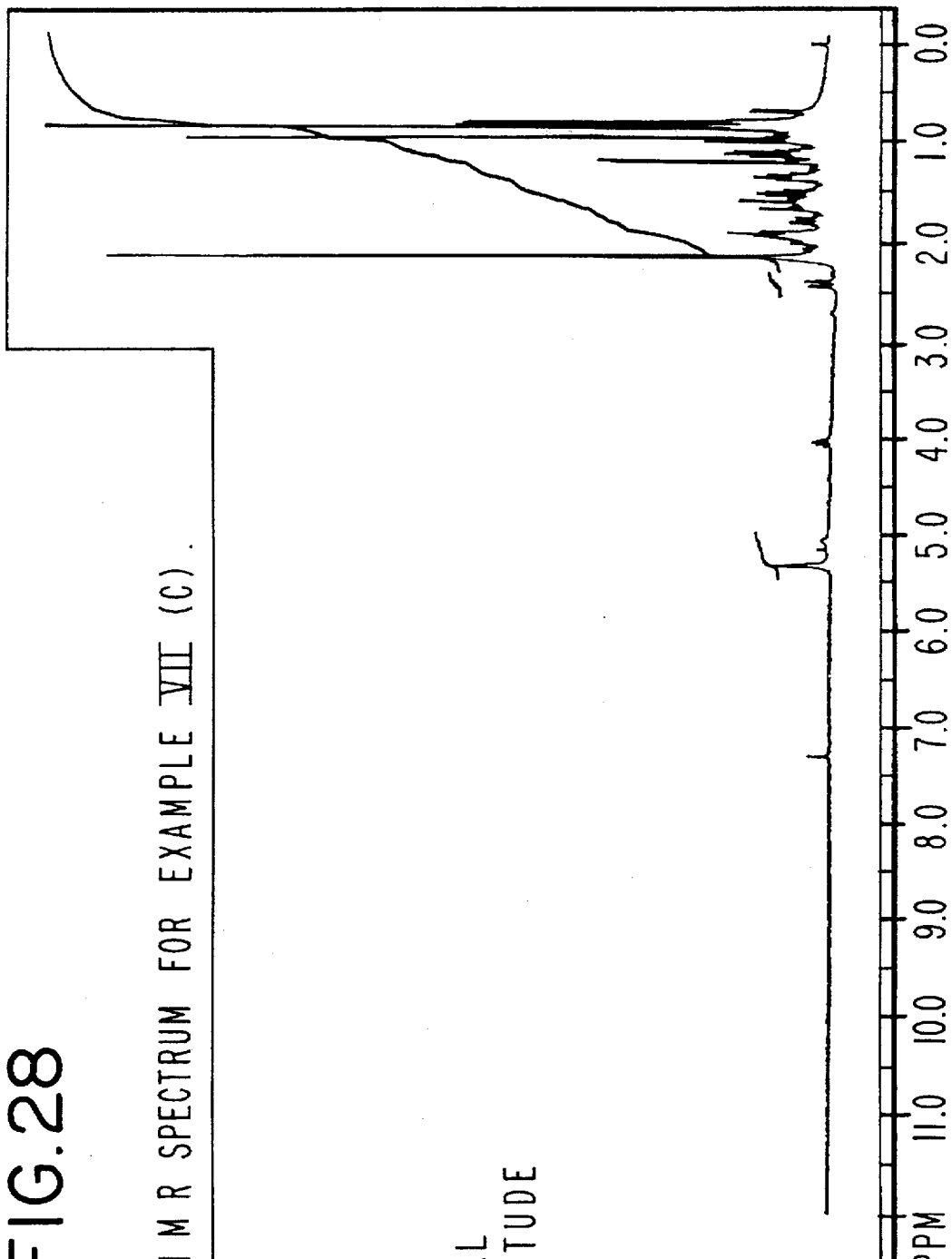

FIG. 28 is the NMR spectrum for the mixture of compounds having the structures:

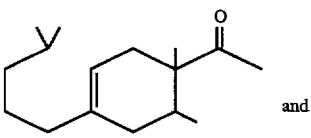

and

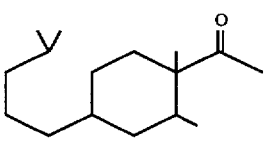

prepared according to Example VII(C).

Figure 29:
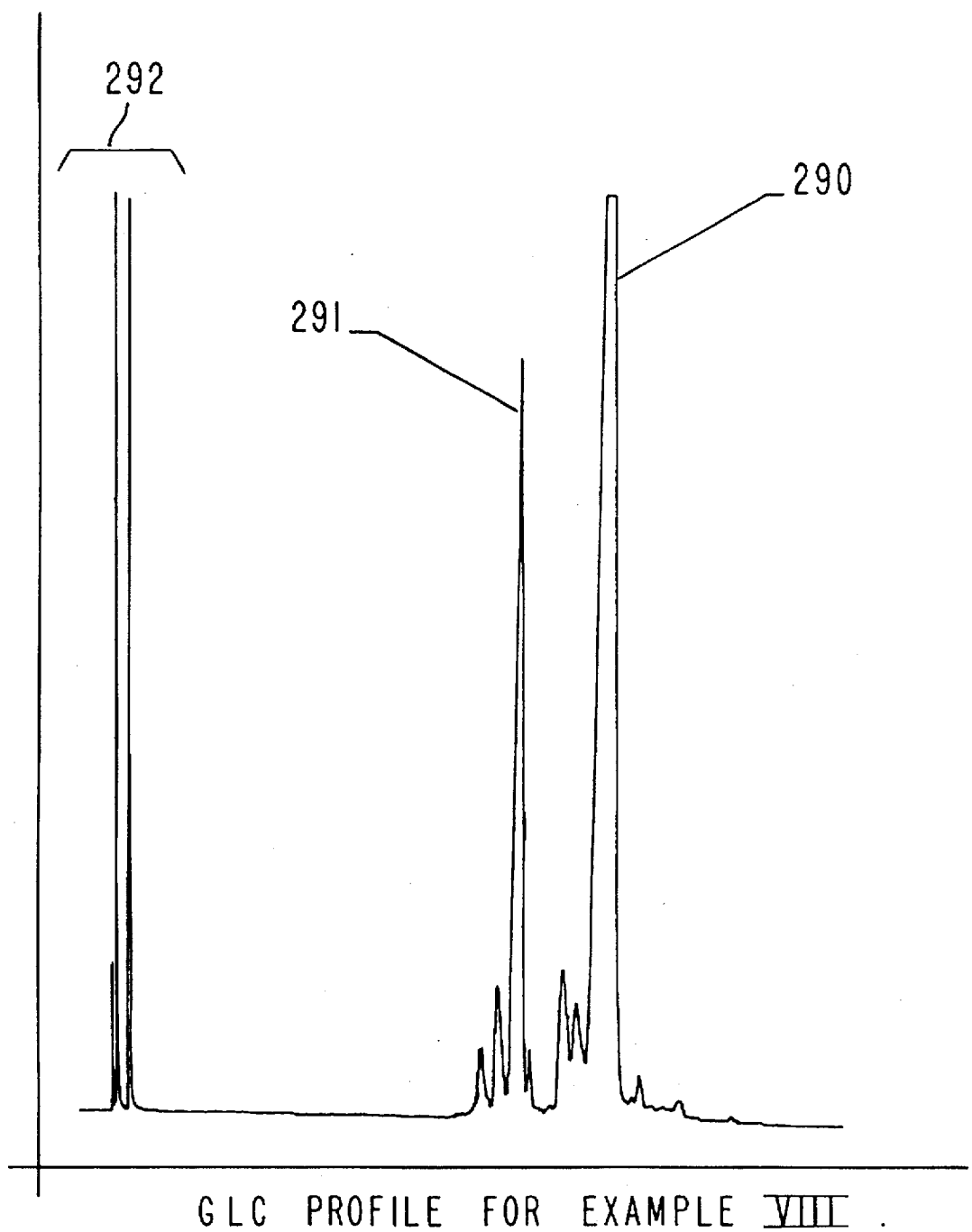

FIG. 29 is the GLC profile for the reaction product of Example VIII containing the compound having the structure:

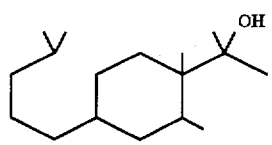

(conditions: SE-30 column programmed from 150°–220° C. at 8° C. per minute).

FIG. 30 is the NMR spectrum for the compound having the structure:

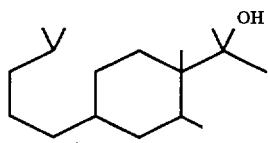

prepared according to Example VIII.

FIG. 30A is an enlargement of section "A" of the NMR spectrum of FIG. 30.

Figure 31:
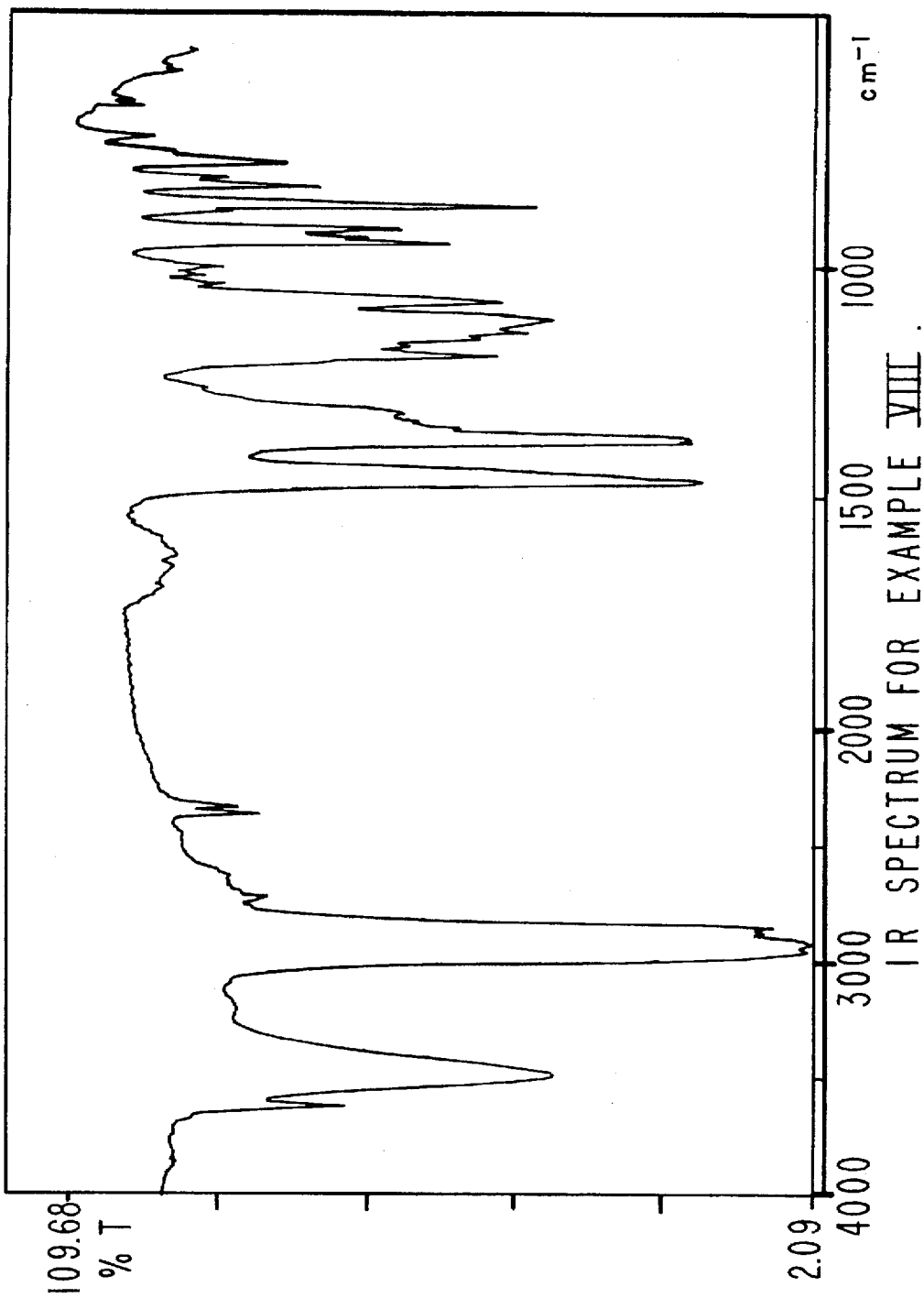

FIG. 31 is the infrared spectrum for the compound having the structure:

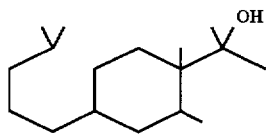

prepared according to Example VIII.

Figure 32:
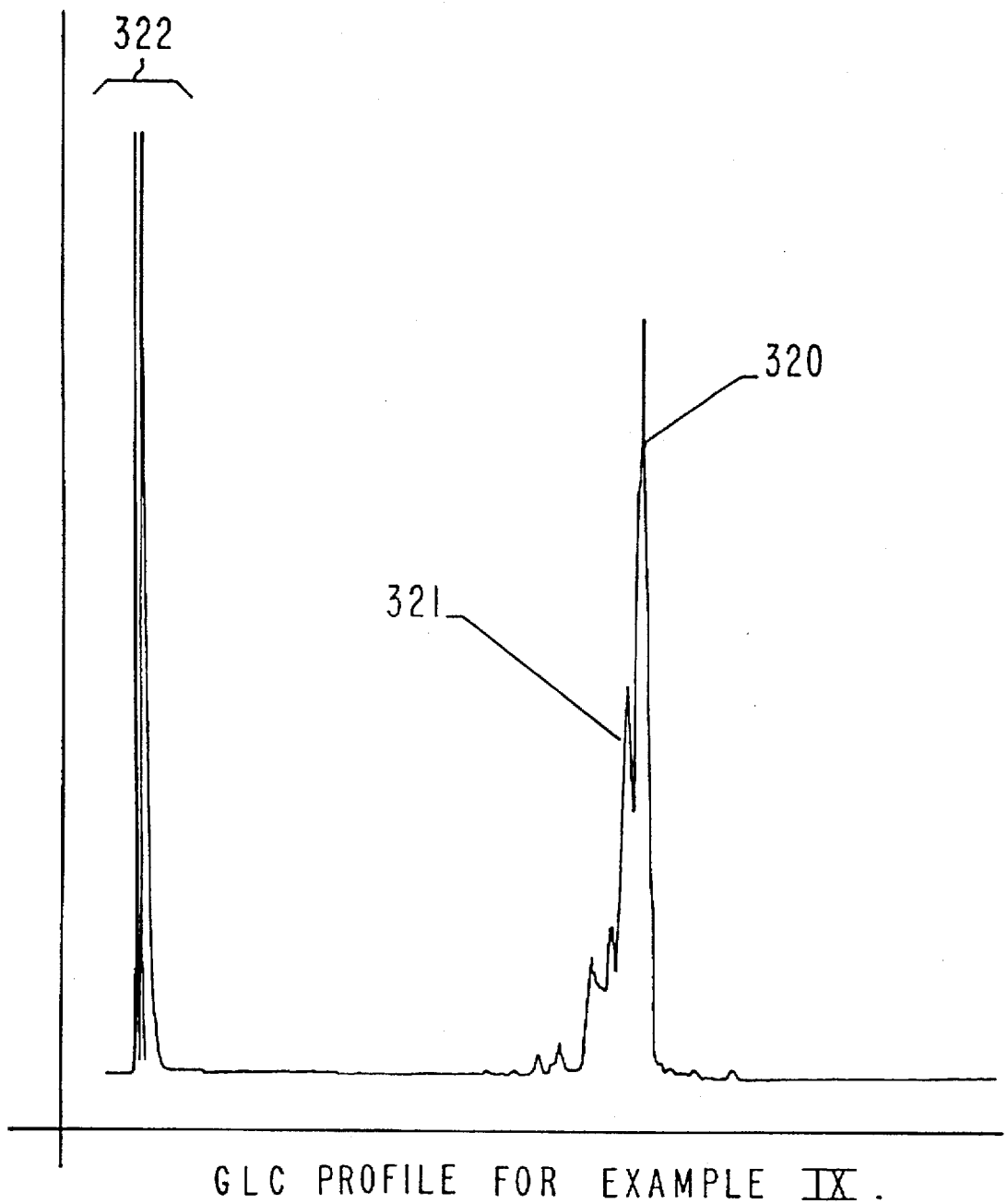

FIG. 32 is the GLC profile for the reaction product of Example IX containing the compound having the structure:

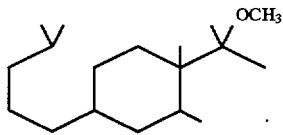

Figure 33:
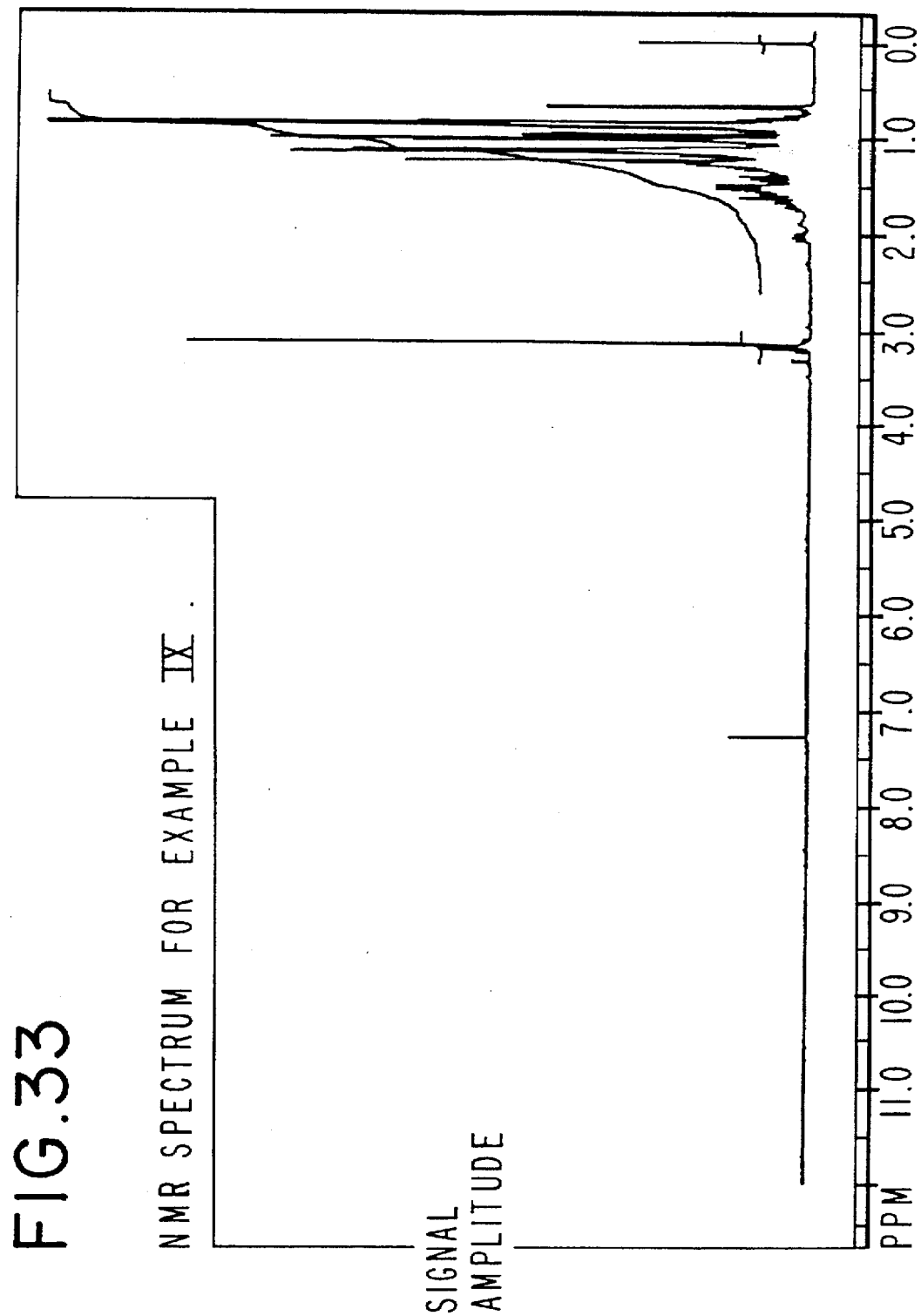

FIG. 33 is the NMR spectrum for the compound having the structure:

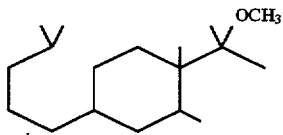

prepared according to Example IX.

Figure 34:
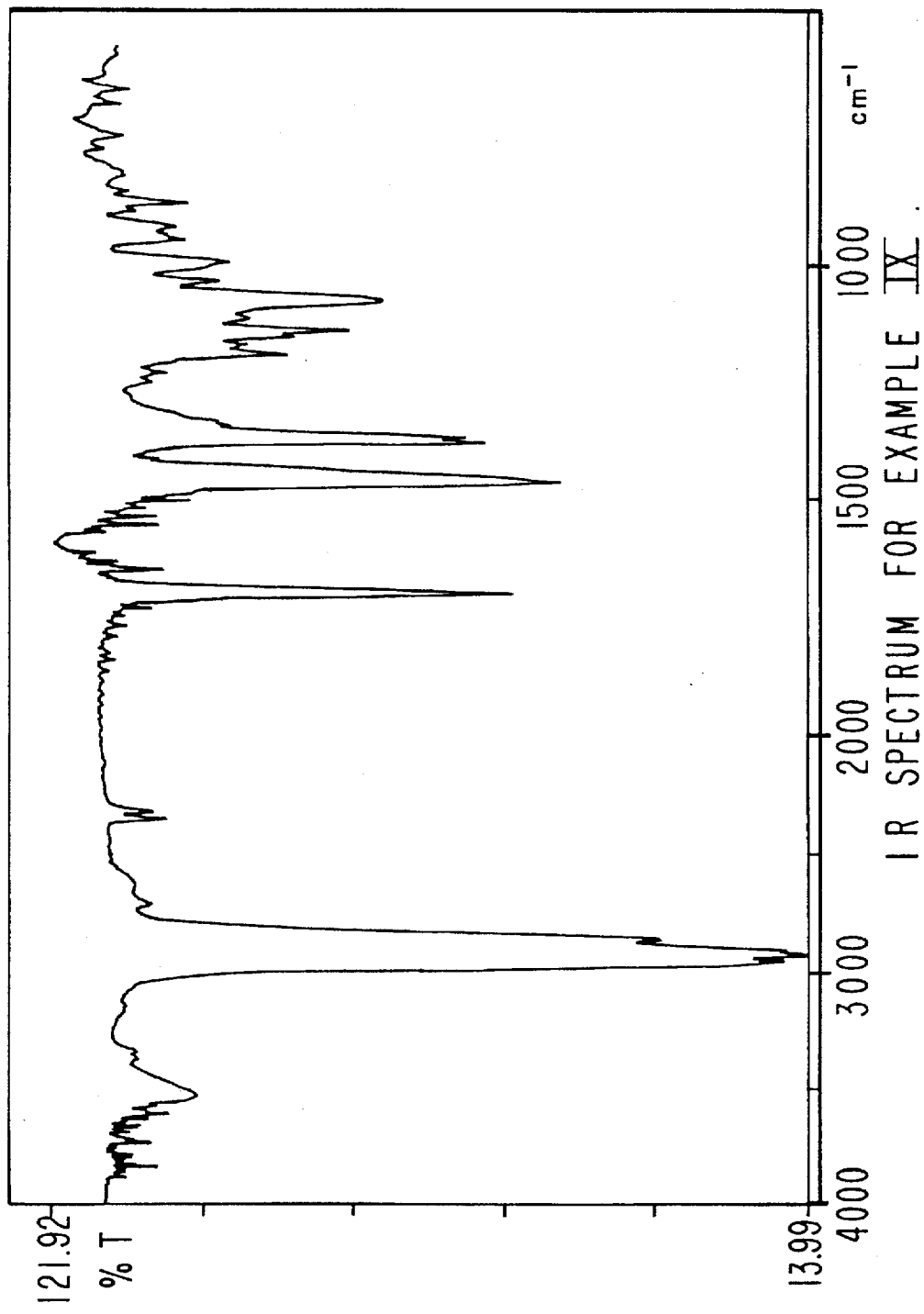

FIG. 34 is the infrared spectrum for the compound having the structure:

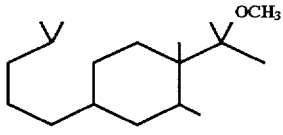

prepared according to Example IX.

Figure 35:
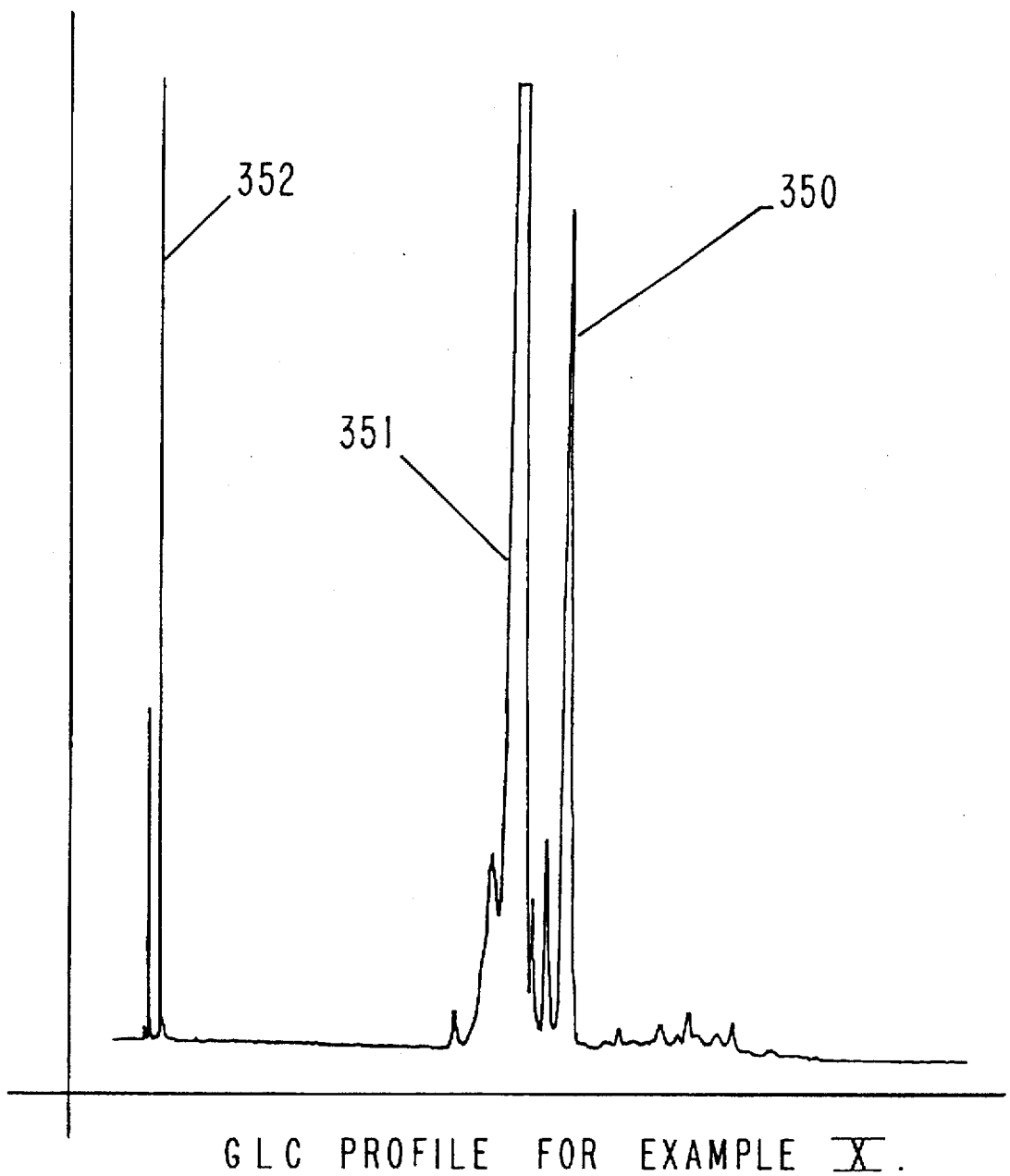

FIG. 35 is the GLC profile for the reaction product of Example X containing the compounds having the structures:

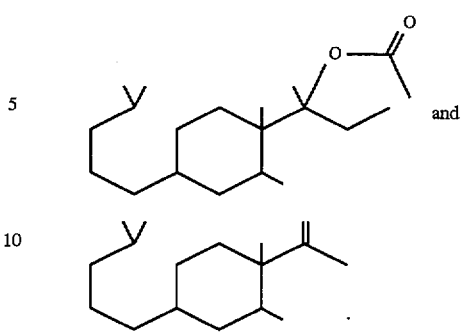

FIG. 36 is the NMR spectrum for the peak indicated by reference numeral "350" on the GLC profile of FIG. 35 for the compound having the structure:

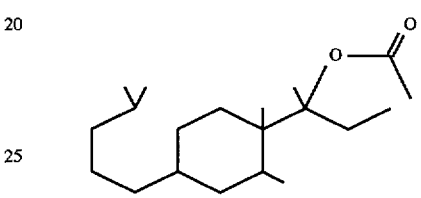

prepared according to Example X.

FIG. 37 is the infrared spectrum for the peak indicated by reference numeral "350" on the GLC profile of FIG. 35 for the compound having the structure:

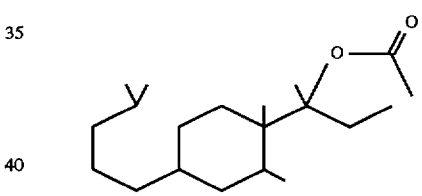

prepared according to Example X.

FIG. 38 is the NMR spectrum for the peak indicated by reference numeral "351" on the GLC profile of FIG. 35 for the compound having the structure:

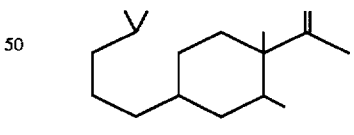

prepared according to Example X.

FIG. 39 is the infrared spectrum for the peak indicated by reference numeral "351" on the GLC profile of FIG. 35 for the compound having the structure:

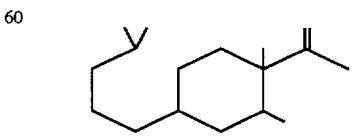

prepared according to Example X.

DETAILED DESCRIPTION OF THE DRAWINGS

Referring to FIG. 1A, the peak indicated by reference numeral 10 is the peak for the compound having the structure:

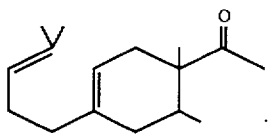

Referring to FIG. 1B, the peak indicated by reference numeral 11 is the peak for the compound having the structure:

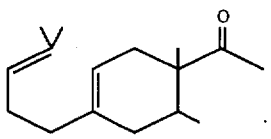

Referring to FIG. 4, the peak indicated by reference numeral 42 is the peak for the reaction product having the structure:

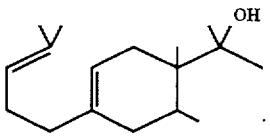

The peak indicated by reference numeral 41 is the peak for the starting material having the structure:

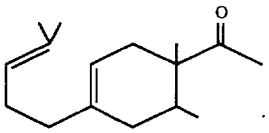

The peak indicated by reference numeral 43 is the peak for the reaction solvent, diethyl ether.

Referring to FIG. 7, the peak indicated by reference numeral 72 is the peak for the reaction product having the structure:

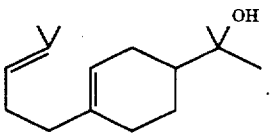

The peak indicated by reference numeral 71 is the peak for the starting material having the structure:

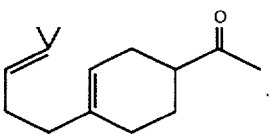

The peaks indicated by reference numeral 73 are for the reaction solvent, diethyl ether.

Referring to FIG. 13, the peak indicated by reference numeral 130 is the peak for the reaction product having the structure:

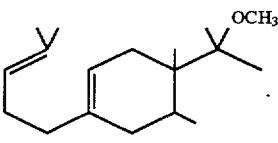

The peak indicated by reference numeral 131 is the peak for the reaction solvent, tetrahydrofuran.

Referring to FIG. 16, the peak indicated by reference numeral 160 is the peak for the reaction product of Example V having the structure:

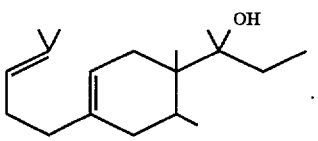

The peak indicated by reference numeral 161 is for the starting material having the structure:

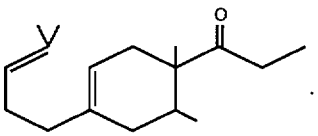

The peaks indicated by reference numeral 162 are for the reaction solvent, diethyl ether.

Referring to FIG. 19, the peak indicated by reference numeral 191 is the peak for the compound having the structure:

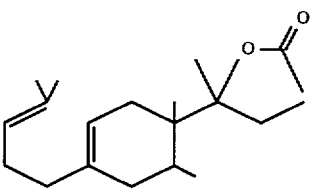

prepared according to Example VI. The peak indicated by reference numeral 190 is the peak for the compound having the structure:

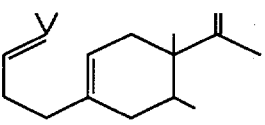

The peak indicated by reference numeral 192 is the peak for reaction for the reaction solvent and starting material, acetic anhydride.

Referring to FIG. 22, the peak indicated by reference numeral 220 is the peak for the reaction product of Example VII(A), the compound having the structure:

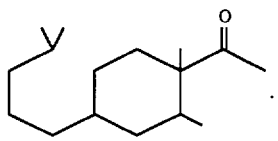

Referring to FIG. 29, the peak indicated by reference numeral 290 is the peak for the reaction product of Example VIII, the compound having the structure:

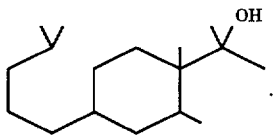

The peak indicated by reference numeral 291 is the peak for the starting material having the structure:

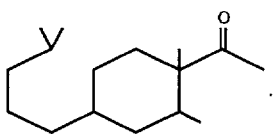

The peaks indicated by reference numeral 292 are for the reaction solvent, diethyl ether.

Referring to FIG. 32, the peak indicated by reference numeral 320 is the peak for the reaction product having the structure:

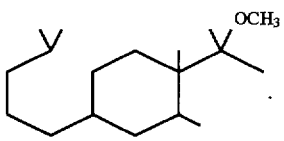

The peak indicated by reference numeral 321 is the peak for the starting material having the structure:

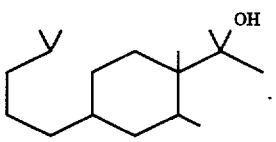

The peaks indicated by reference numeral 322 are for the reaction solvent, tetrahydrofuran.

Referring to FIG. 35, the peak indicated by reference numeral 350 is the peak for the reaction product of Example X, the compound having the structure:

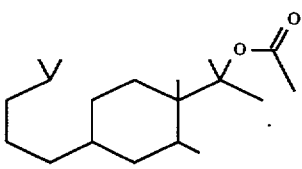

The peak indicated by reference numeral 351 is the peak for the second reaction product of Example X, the compound having the structure:

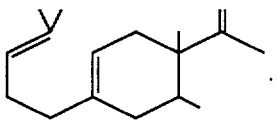

The peak indicated by reference numeral 352 is the peak for the reaction solvent and starting material, acetic anhydride.

THE INVENTION

It has now been discovered that novel solid and liquid perfume compositions, colognes and perfumed articles having intense, substantive and long lasting patchouli, ambery, earthy, woody, peach, mimosa, camphoraceous, mahogany, piney, animalic and musky aromas with patchouli, camphoraceous, earthy, musty, woody, green and fruity topnotes may be provided by use of the 1(4'-methylpentyl)-4-substituted ethylcyclohexane derivatives of our invention defined according to the structure:

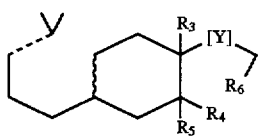

wherein $R_3$, $R_4$, $R_5$ and $R_6$ represent the same or different hydrogen or methyl; wherein the dashed line line represents a carbon carbon single bond or a carbon carbon double bond; wherein the wavy line represents a carbon carbon single bond or a carbon carbon double bond; with the proviso that when the wavy line is a carbon carbon single bond then the dashed line is a carbon carbon single bond; wherein Y is a moiety selected from the group consisting of:

(i) the moiety having the structure:

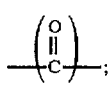

(ii) the moiety having the structure:

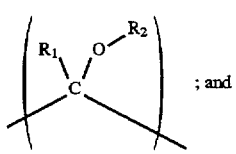

; and (iii) the moiety having the structure:

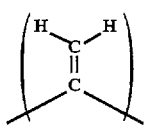

wherein $R_2$ represents hydrogen, $C_1$–$C_4$ lower alkyl or $C_1$–$C_2$ acyl; and wherein $R_1$ represents $C_1$–$C_4$ lower alkyl with the additional proviso that when Y is the moiety:

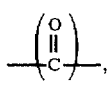

then the dashed line is a carbon carbon single bond.

The 1(4'-methylpentyl)-4-substituted ethylcyclohexane derivatives of our invention may be produced by first carrying out the well known Diels-Alder reaction:

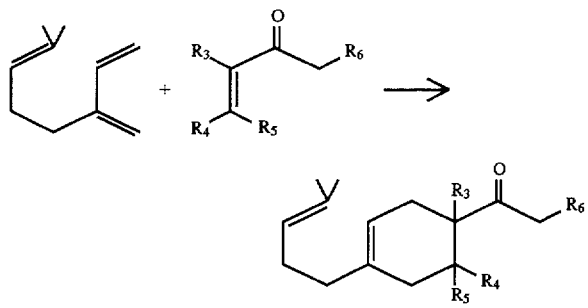

described and exemplified in U.S. Pat. No. 3,911,018 issued on Oct. 7, 1975, the specification for which is incorporated by reference herein That reaction is also described in U.S. Pat. No. 2,933,506 issued in April of 1960, the specification for which is incorporated by reference herein. In the foregoing reaction, $R_3$, $R_4$, $R_5$ and $R_6$ each represent the same or different methyl or hydrogen.

The resulting product having the structure:

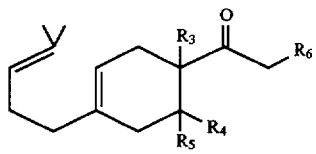

may then be reacted with an organometallic compound such as methyl lithium, methyl magnesium chloride or methyl magnesium bromide according to the generic reaction:

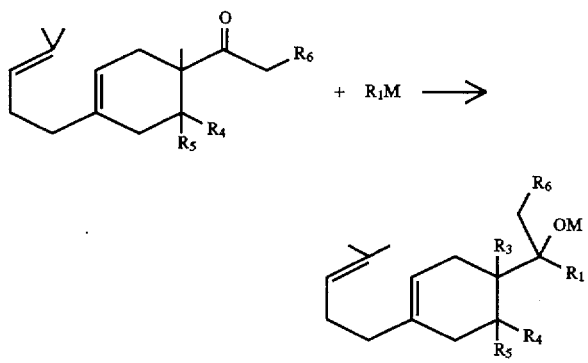

which is exemplified by the reactions:

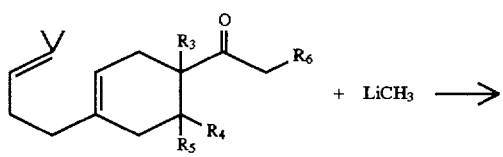

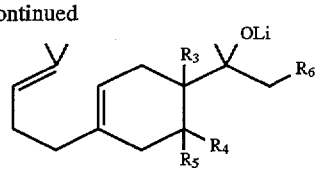

(using methyl lithium) or:

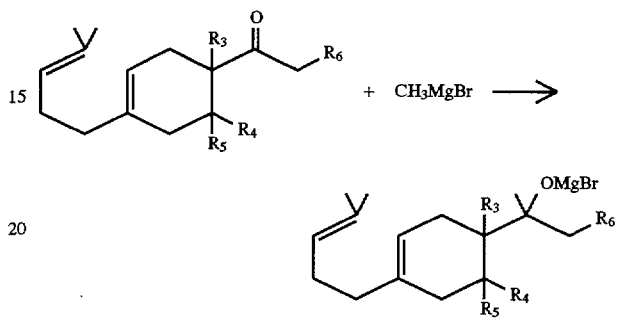

(using methyl magnesium bromide) or:

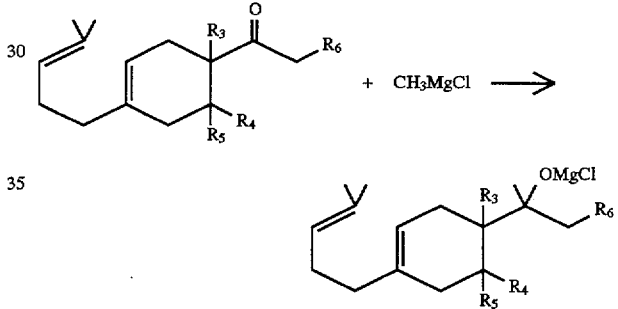

(using methyl magnesium chloride). In the foregoing reaction:

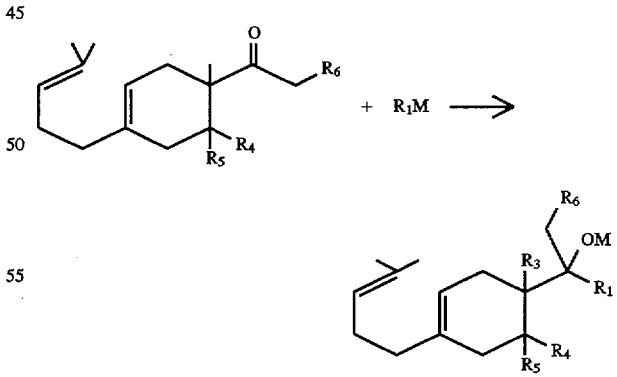

M, accordingly, represents lithium or magnesium halide such as magnesium bromide or magnesium chloride and $R_1$ represents methyl or ethyl.

The resulting organometallic compound having the structure:

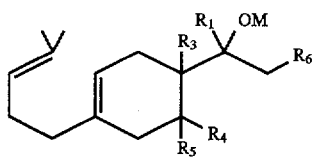

may then be hydrolyzed in acetic media using, for example, aqueous hydrochloric acid or aqueous ammonium chloride according to the reaction:

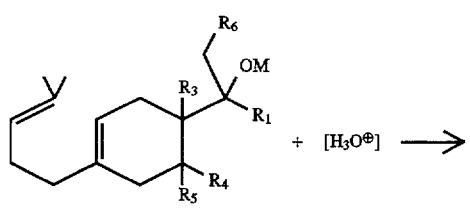

exemplified by the reaction:

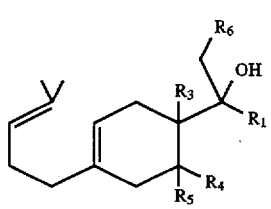

The resulting product defined according to the structure:

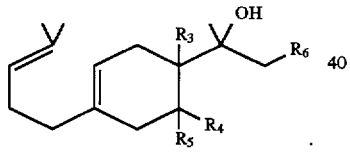

can be used "as is" for its perfumery properties or may be further reacted as set forth, infra.

Alternatively, the compound having the structure:

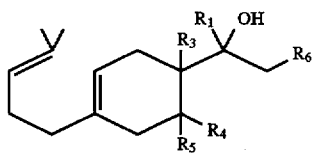

may be hydrogenated using hydrogen and a catalyst such as palladium or palladium on carbon or palladium on calcium carbonate according to the reaction:

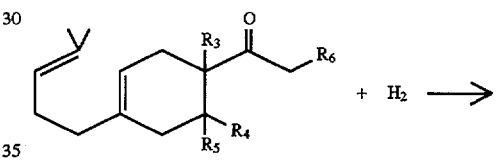

wherein the dashed line represents a carbon carbon single bond or a carbon carbon double bond and the wavy line represents a carbon carbon single bond or a carbon carbon double bond with the proviso that when the wavy line is a carbon carbon single bond then the dashed line is a carbon carbon single bond. The hydrogenation reaction can be carried out to the extent wherein both carbon carbon double bonds are hydrogenated thusly:

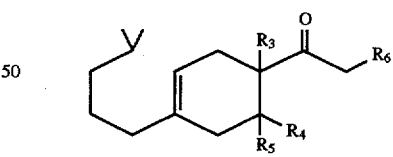

or can be carried out where a portion of the product contains carbon-carbon unsaturation per the structure:

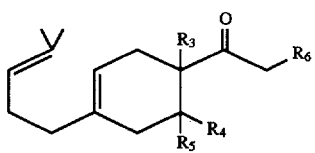

according to the reaction:

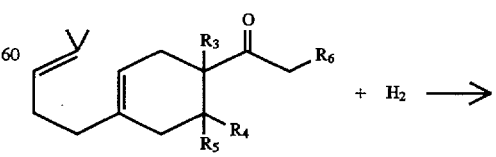

-continued

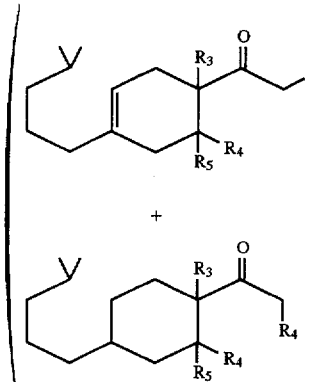

as exemplified in Example VII(B) and VII(C), infra.

The reaction products having the structures:

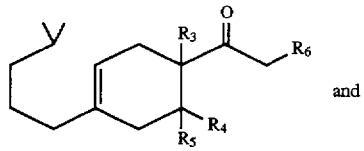

and

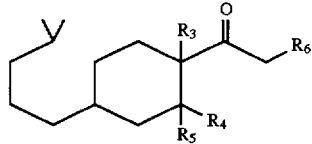

are both novel compounds.

The resulting products:

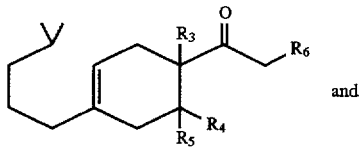

and

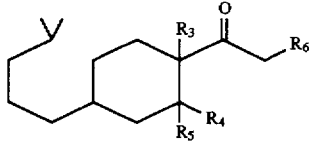

may then be reacted with methyl lithium or a methyl magnesium halide such as methyl magnesium bromide or methyl magnesium chloride according to the reactions:

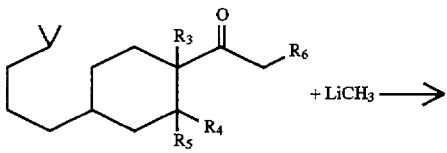

-continued

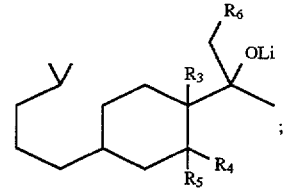

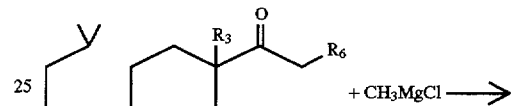

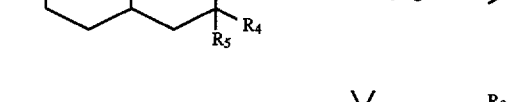

;and

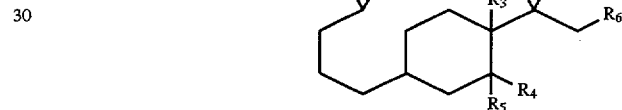

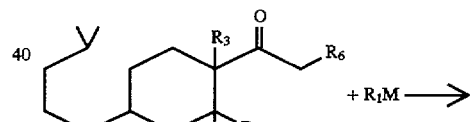

or according to the generic reaction:

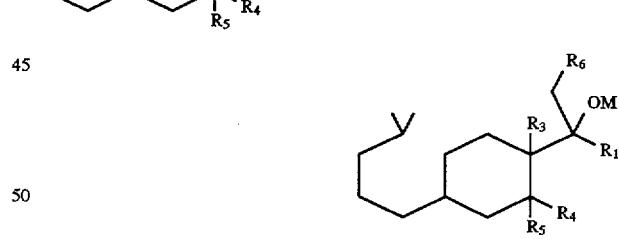

wherein M represents Li, MgBr or MgCl and $R_1$ represents $C_1$–$C_4$ lower alkyl.

In the alternative, the reaction also carried out is as follows:

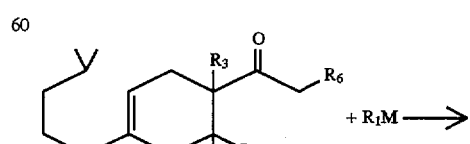

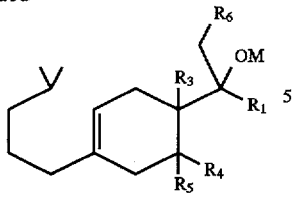

when the precursor is only partially hydrogenated.

The resulting organometallic compounds may then be hydrolyzed in the presence of an acid hydrolysis reagent such as hydrochloric acid or ammonium chloride according to the reaction:

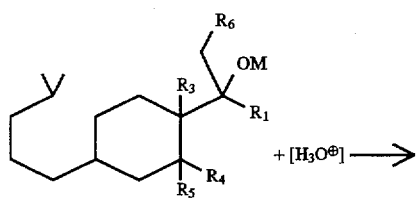

or the reaction:

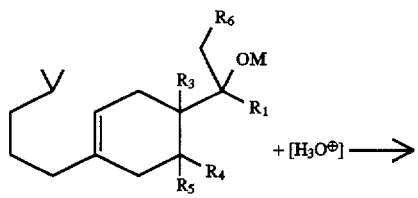

The resulting products having the structures:

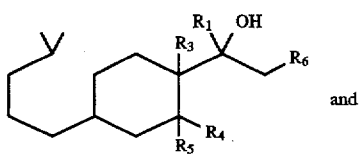

and

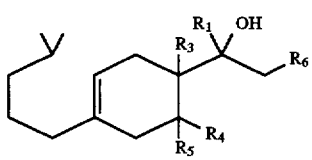

shown generically as the structure:

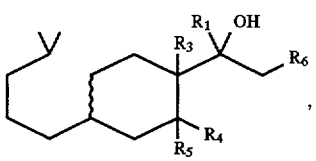

may then be used "as is" for their perfumery properties or they may be further reacted, for example, forming an alkyl ether, a methylene derivative (in the case where $R_6$ is hydrogen) or an ester such as a formate or acetate.

In forming the ether, the compounds defined according to the generic structure:

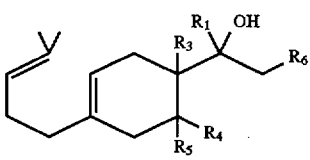

for example, the compound having the structure:

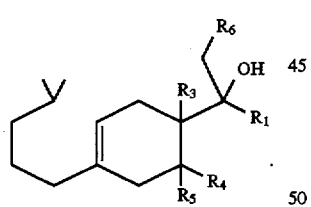

may be reacted with an alkali metal hydride such as sodium hydride or potassium hydride having the formula:

M'H wherein M' is sodium or potassium according to the reaction:

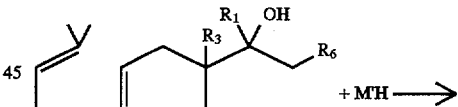

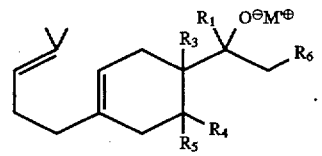

The resulting organometallic compound is then reacted with either an acyl halide, an acyl anhydride or an alkyl halide according to the reaction:

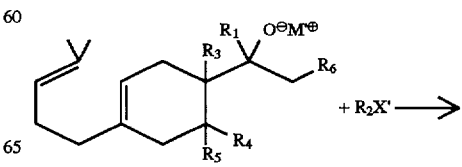
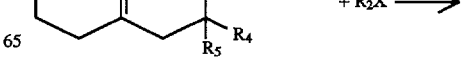

-continued

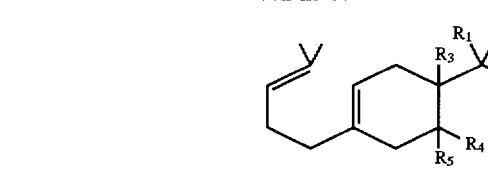

or

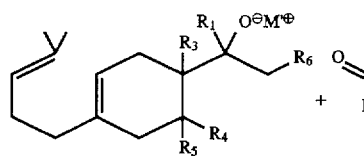

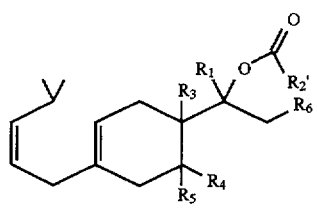

wherein R₂' is hydrogen or methyl or according to the reaction:

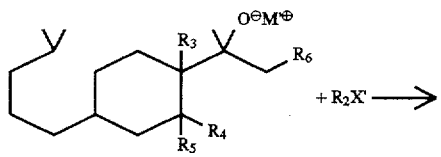

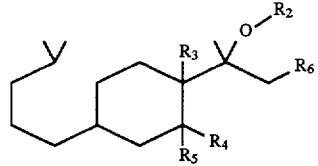

wherein X' represents chloro, bromo or iodo and R₂ represents $C_1$–$C_2$ acyl or $C_1$–$C_4$ alkyl. Thus the compound:

R₂X' can be an acyl halide or an alkyl halide. Examples of acyl halides are acetyl chloride. Examples of alkyl halides are methyl iodide or methyl chloride. More specifically, reactions, to wit:

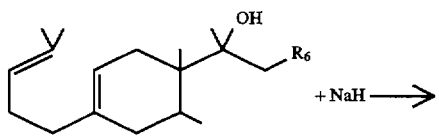

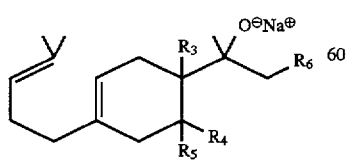

and

-continued

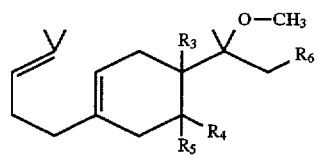

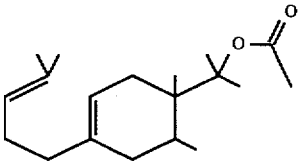

can take place; or in the case of acetic anhydride, the reaction can proceed directly from the tertiary alcohol thusly:

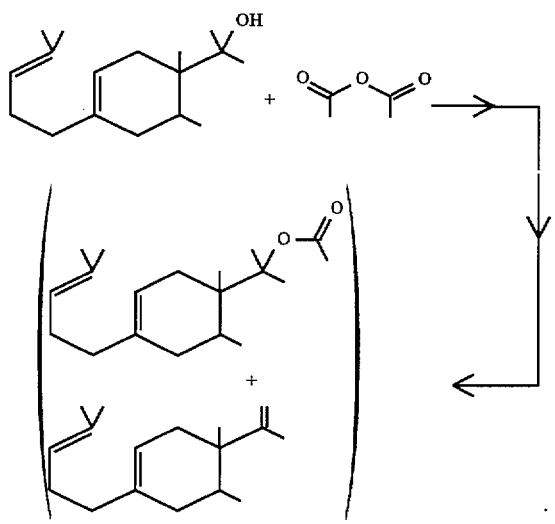

However, in the case of using acetic anhydride, the majority of the reaction product, rather than being the ester having the structure:

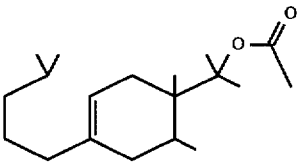

or the structure:

or the structure:

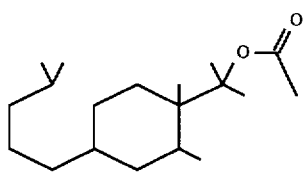

includes in major proportion compounds having the structures:

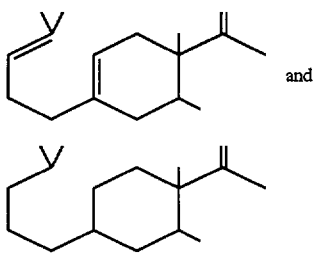

as well as the compound having the structure:

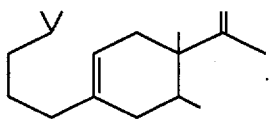

In carrying out the Grignard reactions:

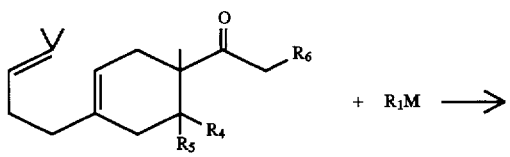

and

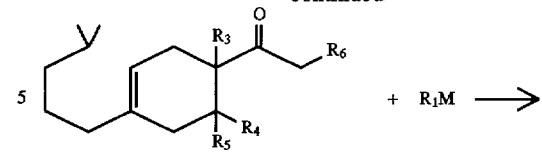

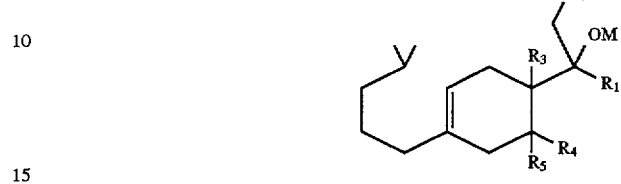

the Grignard reagent, methyl lithium or methyl magnesium chloride or methyl magnesium bromide or ethyl magnesium chloride or ethyl magnesium bromide, is formed in solution usually in a solution of diethyl ether or tetrahydrofuran. While maintaining the reaction temperature at from −5° C. up to +5° C., the precursor ketone having the structure:

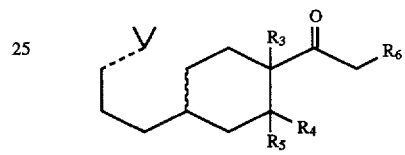

is slowly added to the reaction mass thereby forming the organometallic compound defined according to the structure:

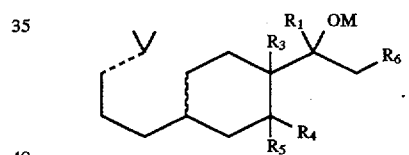

The resulting organometallic compound having the structure:

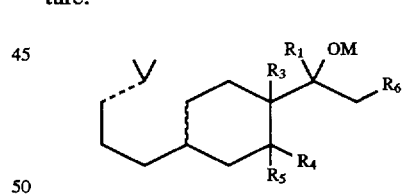

is then hydrolyzed in aqueous acidic media, for example, 10% acetic acid or 5% hydrochloric acid or 10% ammonium chloride in water, at room temperature thereby forming the tertiary alcohol defined according to the structure:

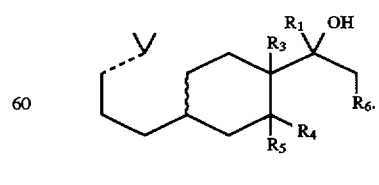

The resulting product is then fractionally distilled and used "as is" or further reacted.

In carrying out the hydrogenation (a reduction) reaction, that is the reaction, to wit:

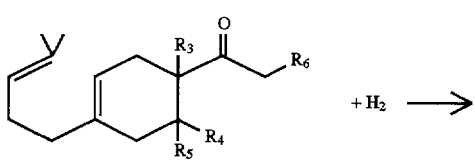

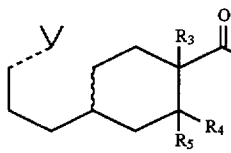

or the reaction:

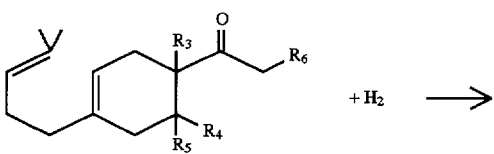

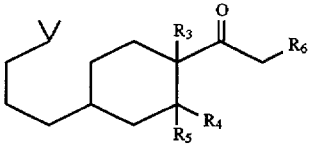

or the reaction:

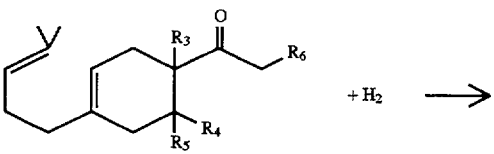

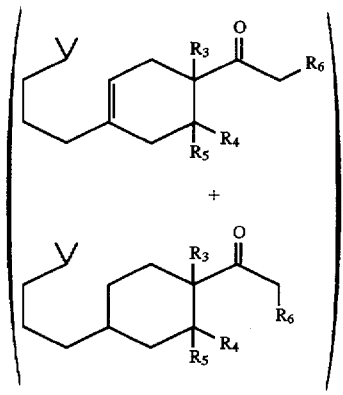

to form the compounds having the structure:

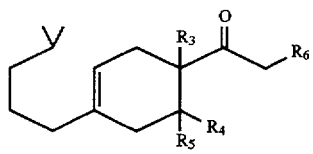

and

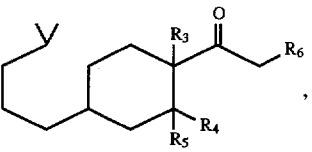

The reaction is carried out under high pressure. When desired to form the product having the structure:

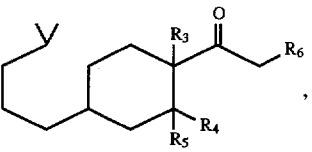

the reaction is carried out at 400–500 psig at a temperature of 75°–110° C. using a palladium on carbon catalyst with the percentage of palladium on carbon being between 1 and 2%. When it is desired to form a high proportion (e.g., 40–60%) of the compound having the structure:

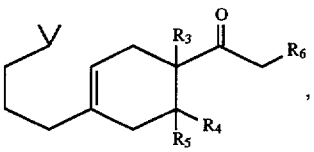

then lower hydrogen pressures, e.g., 350 psig are used, using a lower temperature, e.g., 35°–45° C.; and using the same catalyst, palladium on carbon or palladium on calcium carbonate. In all cases, the reaction time is between about 3 hours and about 10 hours.

In carrying out the etherification reaction, one of the compounds defined according to the structure or a mixture of compounds defined according to the structure:

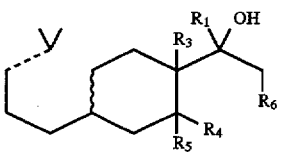

is first reacted with an alkali metal hydride defined according to the structure:

M'H according to the reaction:

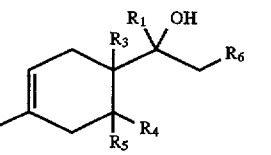

or

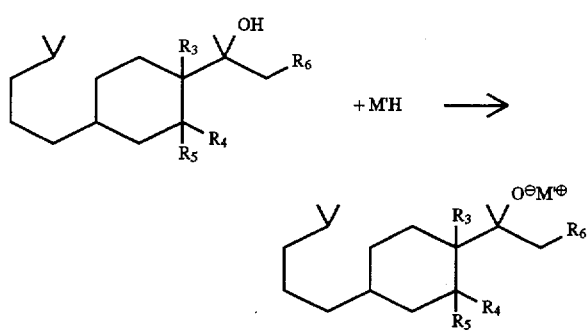

or the reaction:

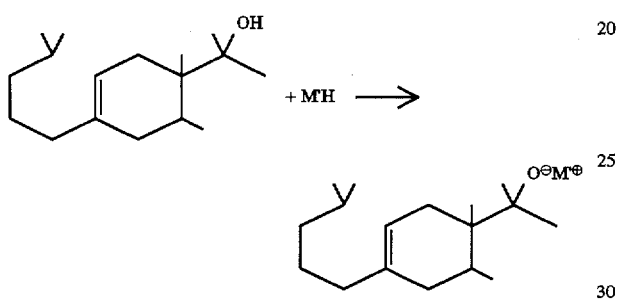

(for example). Initially, the alkali metal hydride, e.g., sodium hydride, is admixed with a suitable solvent, for example, tetrahydrofuran with the weight ratio of alkali metal hydride:solvent being from about 5% up to about 15%, preferably 10%. At reflux conditions, e.g., from about 65° up to about 80° C. at between 1 and 1.5 atmospheres pressure, the alcohol having the structure:

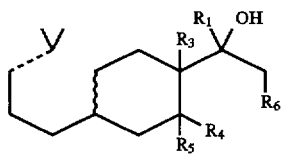

is added to the alkali metal hydride solution over a period of about 2–4 hours, thereby forming the organometallic salt defined according to the structure:

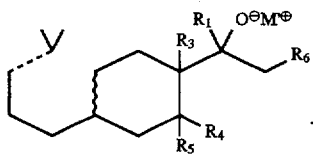

The compound defined according to the structure:

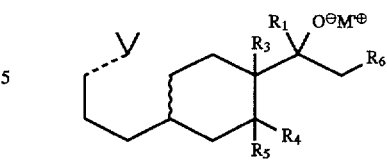

is then reacted with an alkyl halide such as methyl iodide defined according to the formula:

$R_2X'$ at a temperature of between about 20° up to about 40° C. in the tetrahydrofuran solution.

At the end of the reaction, the reaction mass is "worked up" by means of quenching with water. The resulting product is fractionally distilled in order to yield the substantially pure ether product defined according to the structure:

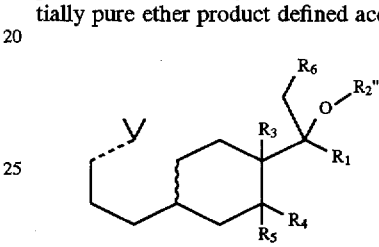

wherein $R_2''$ represents $C_1$–$C_4$ lower alkyl.

In carrying out the esterification reaction (which forms a small amount of ester and a large amount of methylene-substituted compound defined according to the structure:

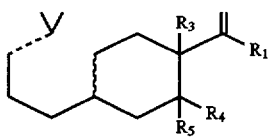

with the ester defined according to the structure:

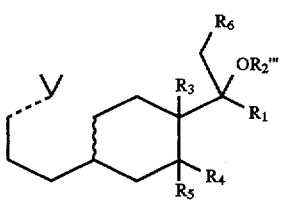

wherein $R_2'''$ represents $C_1$–$C_2$ acyl), the reaction is carried out with preferably a 50% excess amount of acylating agent, e.g., acetic anhydride or acetyl chloride or formic acid, in the presence of a catalyst such as methanesulfonic acid. When using the methanesulfonic acid catalyst or paratoluenesulfonic acid or paraxylenesulfonic acid, the reaction is carried out for a period of time of between about 2 up to about 4 hours at a temperature of between about 0° C. up to about 10° C. Thus, for example, the reaction that is carried out is as follows:

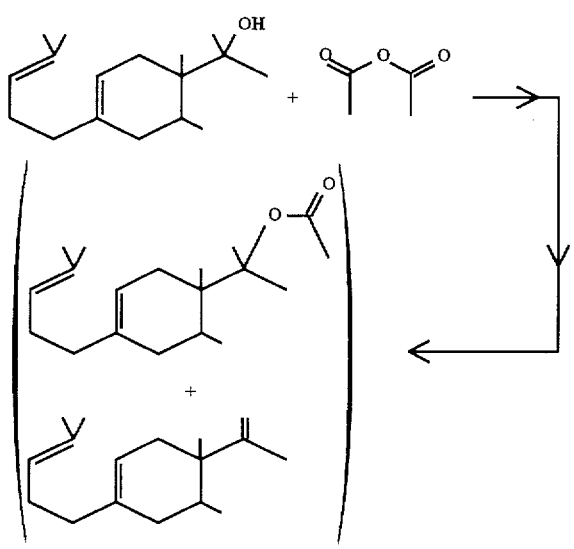

with a large proportion of the compound having the structure:

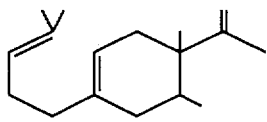

being prepared. The resulting product is then "worked up" as by quenching using water and aqueous sodium bicarbonate followed by drying of the resulting product and fractional distillation to yield the resulting mixture of compounds containing a major proportion of compounds defined according to the structure:

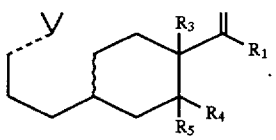

The following Table I sets forth the structure of compounds produced according to our invention and their perfumery properties:

TABLE I

| Structure of 1(4'-methylpentyl)-4-substituted ethylcyclohexane derivative | Perfumery Properties |
|---|---|
| The compound having the structure: 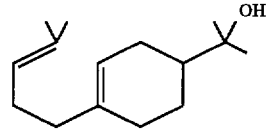 prepared according to Example I, bulked distillation fractions 22–27. | A patchouli, ambery, earthy, woody, peach, mimosa and camphoraceous aroma with patchouli, camphoraceous, earthy, musty and woody topnotes. |

TABLE I-continued

| Structure of 1(4'-methylpentyl)-4-substituted ethylcyclohexane derivative | Perfumery Properties |
|---|---|
| The compound having the structure: 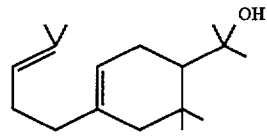 prepared according to Example II, bulked distillation fractions 5–9. | A patchouli aroma. |
| The compound having the structure: 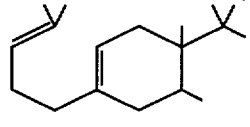 prepared according to Example III, bulked distillation fractions 7 and 8. | A woody and mahogany aroma. |
| The compound having the structure: 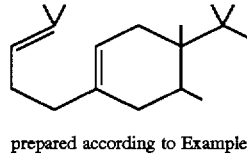 prepared according to Example IV, bulked distillation fractions 8–11. | A woody and patchouli aroma with green topnotes. |
| The compound having the structure: 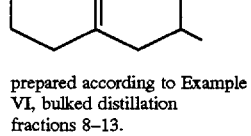 prepared according to Example V, bulked distillation fractions 8–12. | A camphoraceous and piney aroma. |
| The compound having the structure: 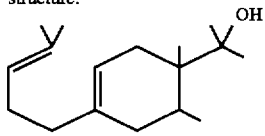 prepared according to Example VI, bulked distillation fractions 8–13. | A woody aroma. |
| The compound having the structure: 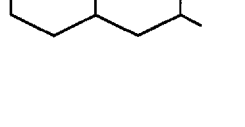 | A woody, patchouli, animalic and musky aroma. |

TABLE I-continued

| Structure of 1(4'-methylpentyl)-4-substituted ethylcyclohexane derivative | Perfumery Properties |
| --- | --- |
| prepared according to Example VIII, bulked distillation fractions 13–24. The compound having the structure:<br>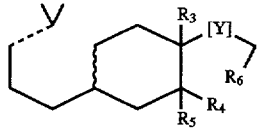 | A patchouli, ambery and woody aroma with fruity topnotes. |
| prepared according to Example IX, bulked distillation fractions 9–17. | |

The 1(4'-methylpentyl)-4-substituted ethylcyclohexane derivatives of our invention defined according to the structure:

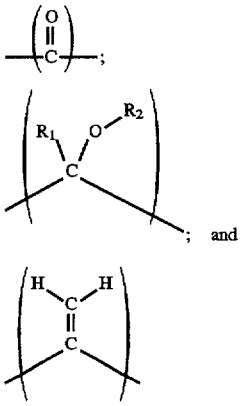

wherein $R_3$, $R_4$, $R_5$ and $R_6$ each represents hydrogen or methyl; wherein the dashed line represents a carbon carbon single bond or a carbon carbon double bond; wherein the wavy line represents a carbon carbon single bond or a carbon carbon double bond; with the proviso that when the wavy line is a carbon carbon single bond then the dashed line is a carbon carbon single bond; wherein Y is a moiety selected from the group consisting of:

(i)
$$\left(\begin{array}{c} O \\ \| \\ -C- \end{array}\right);$$

(ii)
$$\left(\begin{array}{c} R_1 \diagdown \diagup O \diagdown R_2 \\ C \\ \diagup \quad \diagdown \end{array}\right); \text{ and}$$

(iii)
$$\left(\begin{array}{c} H \diagdown \diagup H \\ C \\ \| \\ C \\ \diagup \quad \diagdown \end{array}\right)$$

wherein $R_2$ is hydrogen, $C_1$–$C_4$ lower alkyl or $C_1$–$C_2$ acyl; and wherein $R_1$ represents $C_1$–$C_4$ lower alkyl with the additional proviso that when Y is the moiety:

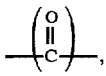

then the dashed line is a carbon carbon single bond, are capable of augmenting, enhancing or imparting intense, substantive and long lasting patchouli, ambery, earthy, woody, peach, mimosa, camphoraceous, mahogany, piney, animalic and musky aromas with patchouli, camphoraceous, earthy, musty, woody, green and fruity topnotes; and at the same time are non-discoloring in perfume compositions.

The 1(4'-methylpentyl)-4-substituted ethylcyclohexane derivatives of our invention and one or more auxiliary perfume ingredients including, for example, alcohols (other than the 1(4'-methylpentyl)-4-substituted ethylcyclohexane derivatives of our invention), ketones, nitriles, esters (other than the 1(4'-methylpentyl)-4-substituted ethylcyclohexane derivatives of our invention), cyclic esters (lactones), ethers (other than the 1(4'-methylpentyl)-4-substituted ethylcyclohexane derivatives of our invention), thioethers, thiols, carboxylic acids, hydrocarbons, natural essential oils and synthetic essential oils may be admixed so that the combined odors of the individual components produce a pleasant and desired fragrance, particularly and preferably in the natural citrusy or musky area. Such perfume compositions usually contain (a) the main note or the "bouquet" or the foundation stone of the composition; (b) modifiers which round off and accompany the main notes; (c) fixatives which include odorous substances which lend a particular note to the perfume throughtout all stages of evaporation and substances which retard evaporation; and (d) topnotes which are usually low-boiling, fresh-smelling materials.

In perfume compositions, it is the individual components which contribute to their particular olfactory characteristics; however, the overall sensory effect of the perfume composition will be at least the sum total of the effect of each of the ingredients. Thus, the 1(4'-methylpentyl)-4-substituted ethylcyclohexane derivatives of our invention can be used to alter, modify, impart or enhance the aroma characteristics of or to a perfume composition, for example, by utilizing or moderating the olfactory reactions contributed by another ingredient in the composition.

The amount of one or more of the 1(4'-methylpentyl)-4-substituted ethylcyclohexane derivatives of our invention which will be effective in perfume compositions as well as in perfumed articles and colognes depends on many factors including the other ingredients, their amounts and the effects which are desired. It has been has found that perfume compositions containing as little as 0.01% of at least one of the 1(4'-methylpentyl)-4-substituted ethylcyclohexane derivatives of our invention or even less (e.g., 0.005%) can be used to impart a very natural, long lasting and substantive intense patchouli, ambery, earthy, woody, peach, mimosa, camphoraceous, mahogany, piney, animalic and musky aroma with patchouli, camphoraceous, earthy, musty, woody, green and fruity topnotes to soaps, cosmetics and other products. The amount employed can range up to 70% of the fragrance components and will depend on considerations of cost, nature of the end product, the effect desired on the finished product and the particular fragrance sought.

At least one of the 1(4'-methylpentyl)-4-substituted ethylcyclohexane derivatives of our invention are useful (taken alone or taken together with other ingredients in perfume compositions) as (an) olfactory component(s) in detergents and soaps, space odorants and deodorants, perfumes, colognes, toilet waters, bath preparations such as lacquers, brilliantines, pomades and shampoos; cosmetic preparations such as creams, deodorants, hand lotions and sun screens; powders such as talcs, dusting powders, face powders and perfumed article compositions of matter such as perfumed polypropylene, perfumed polyethylene and perfumed polyurethanes, particularly long lasting or partially short lasting mixtures of, for example, encapsulated perfumes suspended in free perfume compositions and the like.

When used as an olfactory component, as little as 0.1% of at least one of the 1(4'-methylpentyl)-4-substituted ethylcyclohexane derivatives of our invention will suffice to impart an intense, long lasting and substantive non-discoloring patchouli, ambery, earthy, woody, peach, mimosa, camphoraceous, mahogany, piney, animalic and musky aroma with patchouli, camphoraceous, earthy, musty, woody, green and fruity topnotes. Generally no more than 3% of at least one of the 1(4'-methylpentyl)-4-substituted ethylcyclohexane derivatives of our invention based on the ultimate end product is required in the perfume composition.

In addition, the perfume composition or fragrance composition of our invention can contain a vehicle or carrier for at least one of the 1(4'-methylpentyl)-4-substituted ethylcyclohexane derivatives of our invention. The vehicle can be a liquid such as a non-toxic alcohol (e.g., ethyl alcohol), a non-toxic glycol (e.g., propylene glycol or 1,2-butylene glycol or sorbitol) or the like. The carrier can be an absorbent solid such as a gum (e.g., gum arabic, xanthan gum, guar gum or the like) or components for encapsulating the material (such as gelatin or ethyl cellulose as by coacervation).

When used as a component of a perfumed article such as a perfumed plastic or solid or liquid anionic, cationic, nonionic or zwitterionic detergent or a drier-added fabric softener article or fabric softener composition or a shampoo or a soap, the range of at least one of the 1(4'-methylpentyl)-4-substituted ethylcyclohexane derivatives of our invention usable varies from 0.005% up to about 5% by weight of the perfumed article. The lower range of this range, e.g., 0.005% up to 0.1% of at least one of the 1(4'-methylpentyl)-4-substituted ethylcyclohexane derivatives of our invention, is most prefered when using it in a drier-added fabric softener article or fabric softener composition in view of the need for a "non-perfumy" but pleasant head space aroma above the batch of clothes dried using the drier-added fabric softener article or fabric softener composition in a standard automatically operated tumble drier.

It will thus be apparent that at least one of the 1(4'-methylpentyl)-4-substituted ethylcyclohexane derivatives of our invention can be utilized to augment, alter, modify or enhance sensory properties, particularly organoleptic properties of a wide variety of consumable materials.

The representation of the 1(4'-methylpentyl)-4-substituted ethylcyclohexane derivatives of our invention defined according to the structure:

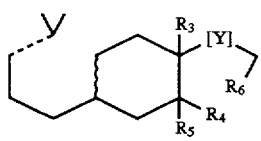

are intended to include herein the each of the various stereoisomers thereof including, but not limited to the stereoisomers depicted as follows:

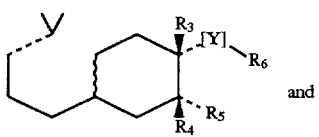

and

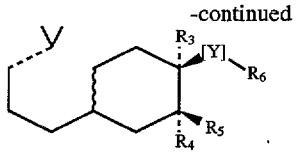

The following examples are illustrative and the invention is to be considered to be restricted thereto only as indicated in the appended claims. Example A sets forth a process for producing precursor ketones of our invention. Examples I-X set forth processes for preparing the 1(4'-methylpentyl)-4-substituted ethylcyclohexane derivatives of our invention. Examples XI, et seq., set forth organoleptic utilities of the 1(4'-methylpentyl)-4-substituted ethylcyclohexane derivatives of our invention.

All parts and percentages given herein are by weight unless otherwise specified.

EXAMPLE A

Reaction:

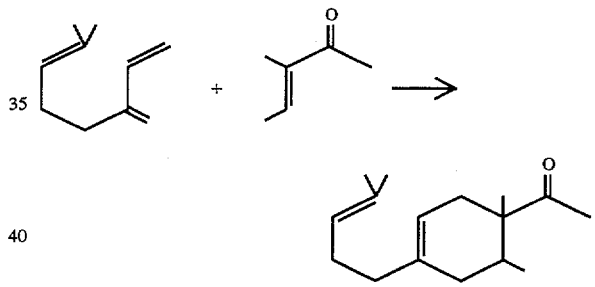

3-Methyl-3-pentenone (2,060 grams, 95%) is added in 15 minutes to a suspension of aluminum chloride (90 grams) in toluene (2 kilograms). The initial exotherm dies out after approximately 5% of the 3-methyl-3-pentenone is added. The mass is warmed to 35° C., and myrcene (3,530 grams, 77%) is added over a period of 2 hours with external cooling as needed to maintain the reaction mixture at 35°–40° C. The mixture is stirred at 35°–40° C. for 2 hours, 27 grams aluminum chloride is added, and the mass is stirred for an additional 9 hours at 35°–40° C.

After standing overnight at room temperature, the mixture is washed at 40° C. with 10% sodium chloride solution and 15% sodium sulfate solution. The washed organic solution is mixed with 100 grams triethanolamine, 100 grams PRIMOL® (U.S.P. white mineral oil available from Exxon Incorporated of Linden, N.J.) and 5 grams IONOL® (Registered Trademark of the Shell Chemical Company; butylated hydroxy toluene) and is distilled rapidly at 2.35 mm/Hg using a short column to give 3,999 grams of product, boiling point 146°–150° C. at 2–3.5 mm/Hg.

EXAMPLE I

PREPARATION OF α,α,1,6-TETRAMETHYL-4-(4-METHYL-3-PENTENYL)-3-CYCLOHEXENE-1-METHANOL

Reactions:

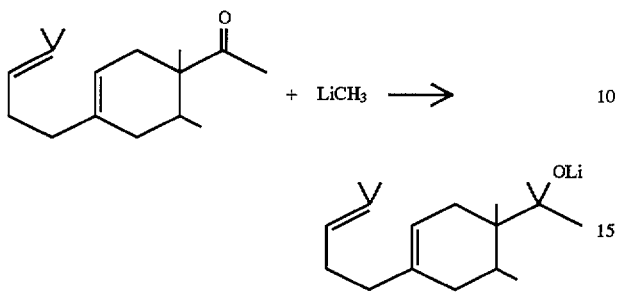

and

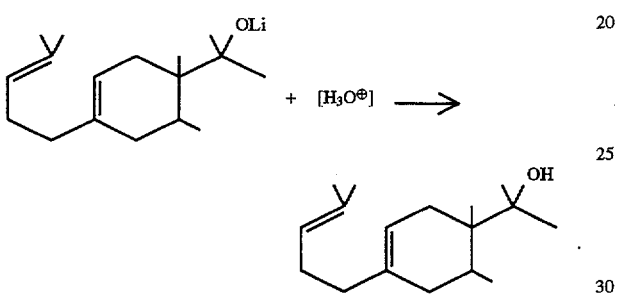

Into a 5 liter reaction vessel equipped with stirrer, thermometer, cooling coil, heating mantle and addition funnel is placed 1,600 ml of a 1.4 molar solution of methyl lithium in diethyl ether. The methyl lithium solution is cooled to 0° C.

Over a period of 2 hours, 374 grams (1.6 moles) of the compound having the structure:

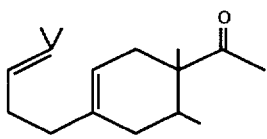

is added to the methyl lithium solution, with stirring while maintaining the reaction temperature at 0° C. The compound having the structure:

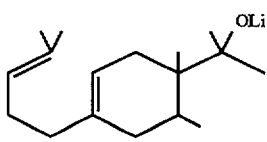

is thus formed.

The resulting mixture is then quenched with a 10% aqueous solution of acetic acid (equal volume).

The resulting mixture is transferred to a separatory funnel and the organic phase is separated from the aqueous phase. The organic phase is then washed with three volumes of saturated aqueous sodium bicarbonate followed by 1 liter of water. The resulting product is then filtered through anhydrous magnesium sulfate in order to dry it. The resulting product (860 grams) is then distilled in a "rushover column" yielding the following fractions:

| Fraction Number | Vapor Temperature (°C.) | Liquid Temperature (°C.) | Vacuum mm/Hg. Pressure |
|---|---|---|---|
| 1 | 37/49 | 61/110 | 80/5.0 |
| 2 | 117 | 150 | 1.13 |
| 3 | 151 | 165 | 1.48 |
| 4 | 90 | 195 | 2.43 |

Fractions 2 and 3 are bulked and redistilled yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 98/125 | 156/158 | 1.51/1.46 | 9:1 |
| 2 | 112 | 158 | 1.52 | 9:1 |
| 3 | 119 | 157 | 1.49 | 9:1 |
| 4 | 127 | 158 | 1.95 | 9:1 |
| 5 | 125 | 158 | 1.72 | 9;1 |
| 6 | 112 | 158 | 2.16 | 9:1 |
| 7 | 139 | 158 | 2.13 | 9:1 |
| 8 | 131 | 158 | 2.02 | 9:1 |
| 9 | 125 | 158 | 1.42 | 9:1 |
| 10 | 129 | 159 | 1.55 | 9:1 |
| 11 | 139 | 159 | 2.29 | 9:1 |
| 12 | 130 | 158 | 1.47 | 9:1 |
| 13 | 131 | 158 | 1.48 | 9:1 |
| 14 | 133 | 158 | 1.56 | 9:1 |
| 15 | 137 | 158 | 1.25 | 9:1 |
| 16 | 137 | 158 | 1.73 | 9:1 |
| 17 | 137 | 163 | 2.34 | 9:1 |
| 18 | 137 | 165 | 2.05 | 9:1 |
| 19 | 156 | 168 | 6.10 | 9:1 |
| 20 | 154 | 167 | 2.10 | 9:1 |
| 21 | 136 | 165 | 1.50 | 9:1 |
| 22 | 132 | 165 | 1.40 | 9:1 |
| 23 | 128 | 165 | 1.46 | 9:1 |
| 24 | 129 | 166 | 1.45 | 9:1 |
| 25 | 129 | 166 | 1.43 | 9:1 |
| 26 | 145 | 166 | 2.30 | 9:1 |
| 27 | 139 | 166 | 1.91 | 9:1 |
| 28 | 141 | 166 | 2.09 | 9:1 |
| 29 | 130 | 162 | 1.44 | 9:1 |
| 30 | 131 | 165 | 1.41 | 9:1 |
| 31 | 132 | 164 | 1.43 | 9:1 |
| 32 | 132 | 164 | 1.42 | 9:1 |
| 33 | 141 | 168 | 1.50 | 9:1 |
| 34 | 134 | 166 | 1.52 | 9:1 |
| 35 | 139 | 168 | 1.81 | 7:3 |
| 36 | 142 | 168 | 2.03 | 7:3 |
| 37 | 142 | 168 | 1.95 | 7:3 |
| 38 | 156 | 169 | 2.25 | 7:3 |
| 39 | 148 | 169 | 2.82 | 7:3 |
| 40 | 112 | 170 | 3.14 | 7:3 |
| 41 | 154 | 169 | 1.52 | 7:3 |
| 42 | 142 | 164 | 2.11 | 7:3 |
| 43 | 140 | 185 | 1.80 | 7:3 |
| 44 | 123 | 200 | 1.95 | 7:3 |

Distillation Fractions 22–27 are bulked for use for their organoleptic properties. Fractions 22–38 are bulked for use in subsequent reactions, e.g., Example IV, infra, and Example VI, infra.

EXAMPLE II

PREPARATION OF α,α-DIMETHYL-4-(4-METHYL-3-PENTENYL)-3-CYCLOHEXENE-1-METHANOL

Reactions:

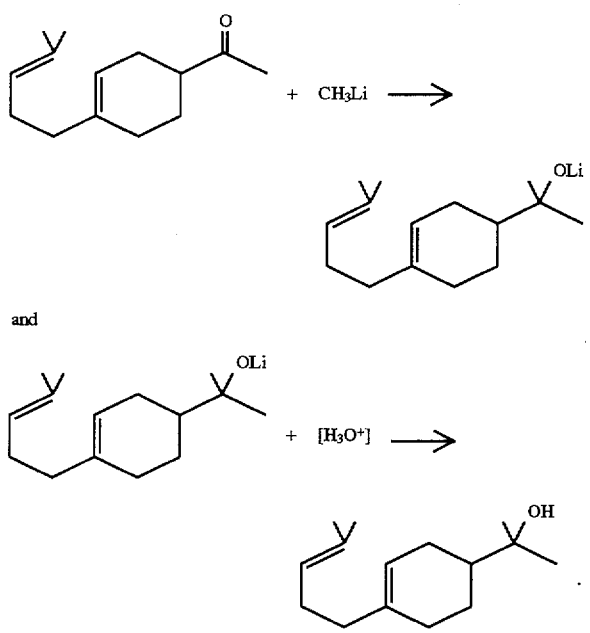

and

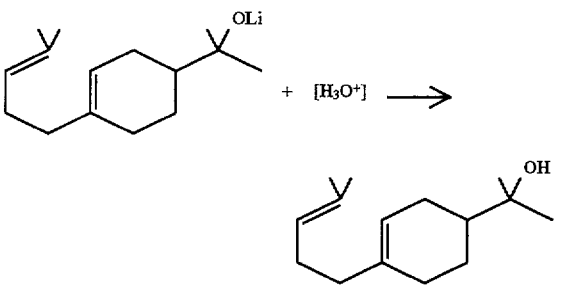

Into a 5 liter reaction vessel equipped with stirrer, thermometer, reflux condenser, cooling coil, heating mantles and addition funnel is placed 1,600 ml of a solution of 1.4 molar methyl lithium in diethyl ether (2.24 moles). The methyl lithium solution is cooled to 0° C. and over a period of 2 hours, 330 grams (1.6 moles) of the compound having the structure:

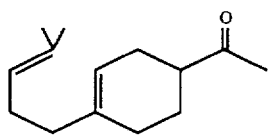

is added to the reaction mass with stirring while maintaining the reaction temperature at 0° C. The product thus formed has the structure:

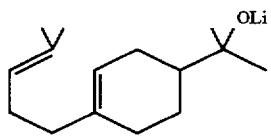

One liter of 10% aqueous acetic acid is then admixed with the resulting reaction product and the temperature of the reaction mass is allowed to warm up to room temperature, 25° C.

The reaction mass is then transferred to a 5 liter separatory funnel and the organic phase is separated from the aqueous phase.

The organic phase is then washed with three 1 liter portions of saturated aqueous sodium bicarbonate solution followed by one 1 liter portion of water. The resulting product is then filtered through anhydrous sodium sulfate yielding 1,364 grams of crude product.

This material is then fractionally distilled on a "rushover" column yielding the following fractions:

| Fraction Number | Vapor Temperature (°C.) | Liquid Temperature (°C.) | Vacuum mm/Hg. Pressure |
|---|---|---|---|
| 1 | 32/65 | 81/150 | 26.2/165 |
| 2 | 113 | 161 | 6.90 |
| 3 | 143 | 170 | 4.55 |
| 4 | 123 | 229 | 3.14 |

Fractions 2 and 3 are bulked and redistilled yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 77/114 | 133/138 | 1.35/1.45 | 9:1 |
| 2 | 112 | 139 | 1.34 | 9:1 |
| 3 | 119 | 141 | 1.29 | 9:1 |
| 4 | 119 | 140 | 1.26 | 9:1 |
| 5 | 124 | 143 | 1.26 | 9:1 |
| 6 | 125 | 145 | 1.13 | 9:1 |
| 7 | 126 | 145 | 1.16 | 9:1 |
| 8 | 129 | 146 | 1.52 | 9:1 |
| 9 | 122 | 144 | 1.12 | 9:1 |
| 10 | 121 | 161 | 1.14 | 9:1 |
| 11 | 92 | 201 | 1.13 | 9:1 |

Distillation fractions 5–9 are bulked for use in perfume compositions.

EXAMPLE III

PREPARATION OF α,α,6,6-TETRAMETHYL-4-(4-METHYL-3-PENTENYL)-3-CYCLOHEXENE-1-METHANOL

Reactions:

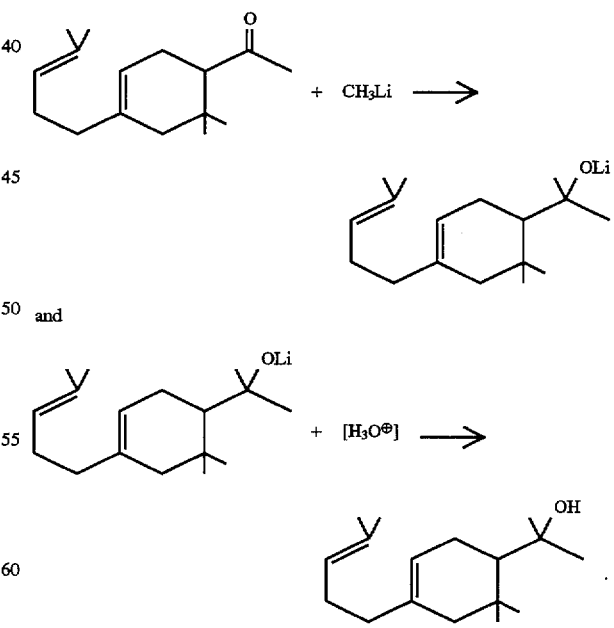

Into a 5 liter reaction vessel equipped with stirrer, thermometer, reflux condenser, cooling coil, heating mantle and addition funnel is placed 1,600 ml of a 1.4 molar solution of methyl lithium in diethyl ether (2.24 moles). The methyl lithium solution is cooled to 0° C. and over a period of 2 hours, 371 grams (1.6 moles) of the compound having the structure:

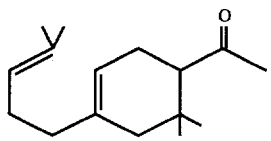

is added to the reaction mass, while maintaining the reaction mass at a temperature of 0° C.

The resulting product has the structure:

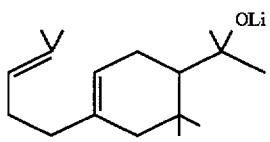

The resulting product is then quenched with 1 liter of 10% aqueous acetic acid. The temperature of the reaction mass is permitted to rise to room temperature (26° C.). The resulting product is transferred to a separatory funnel and the organic phase is separated from the aqueous phase. The organic phase is washed with three 1 liter volumes of saturated sodium bicarbonate. The resulting product is then filtered through anhydrous sodium sulfate and distilled on a "rushover" column yielding the following fractions:

| Fraction Number | Vapor Temperature (°C.) | Liquid Temperature (°C.) | Vacuum mm/Hg. Pressure |
|---|---|---|---|
| 1 | 29/58 | 43/180 | 12/70 |
| 2 | 130 | 165 | 6.90 |
| 3 | 165 | 210 | 4.30 |

Fraction 2 is redistilled yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 39/88 | 155/163 | 3.2/26.4 | 9:1 |
| 2 | 115 | 158 | 3.32 | 9:1 |
| 3 | 124 | 112 | 2.45 | 9:1 |
| 4 | 134 | 161 | 2.80 | 9:1 |
| 5 | 133 | 156 | 2.34 | 9:1 |
| 6 | 156 | 164 | 2.18 | 9:1 |
| 7 | 139 | 173 | 1.99 | 9:1 |
| 8 | 156 | 192 | 2.55 | 9:1 |
| 9 | 153 | 205 | 2.65 | 1:9 |

Distillation fractions 7 and 8 are bulked for their organoleptic uses.

EXAMPLE IV

PREPARATION OF THE METHYL ETHER OF α,α,1,2-TETRAMETHYL-4-(4-METHYL-3-PENTENYL)-3-CYCLOHEXENE-1-METHANOL

Reactions:

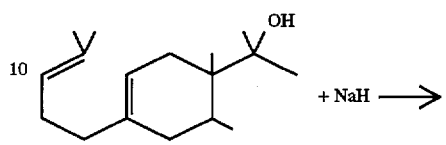

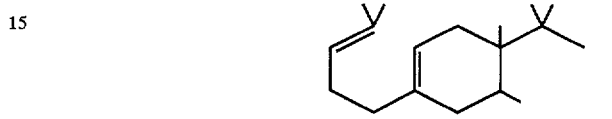

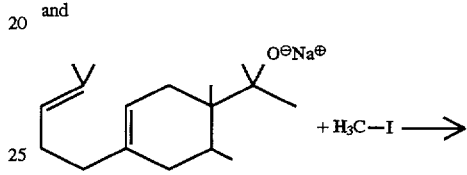

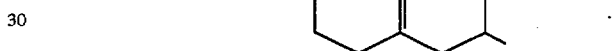

Into a 5 liter reaction vessel equipped with stirrer, thermometer, reflux condenser, heating mantle and addition funnel is placed 62.4 grams of sodium hydride and 631 grams of tetrahydrofuran. The resulting sodium hydride solution is heated to reflux (64°–65° C.).

While refluxing the sodium hydride/tetrahydrofuran solution over a period of 3 hours, 500 grams (2 moles) of the compound having the structure:

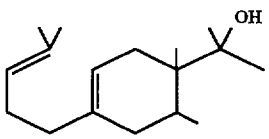

is added to the reaction mass. At the end of the 3 hour period, the compound present has the structure:

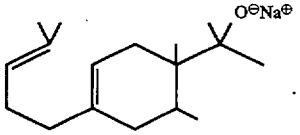

Over a period of 2 hours, 341 grams (2.4 moles) of methyl iodide is added to the reaction mass with stirring while maintaining the reaction mass at a temperature of 69° C. At the end of the 2 hour period, the reaction mass is cooled to room temperature and washed with three 1 liter volumes of water. The resulting product is then filtered through anhydrous sodium sulfate.

The resulting product is then distilled on a "rushover" column to yield the following fractions:

| Fraction Number | Vapor Temperature (°C.) | Liquid Temperature (°C.) | Vacuum mm/Hg. Pressure |
|---|---|---|---|
| 1 | 87 | 146 | 1.54 |
| 2 | 127 | 149 | 1.55 |
| 3 | 131 | 152 | 1.50 |
| 4 | 135 | 207 | 1.39 |

Fractions 2 and 3 are bulked and redistilled yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 49/130 | 148/158 | 0.966/1.09 | 9:1 |
| 2 | 128 | 156 | 0.936 | 9:1 |
| 3 | 134 | 157 | 1.13 | 9:1 |
| 4 | 131 | 152 | 1.09 | 9:1 |
| 5 | 133 | 157 | 1.03 | 9:1 |
| 6 | 128 | 157 | 0.528 | 4:1 |
| 7 | 125 | 159 | 0.954 | 4:1 |
| 8 | 128 | 159 | 1.01 | 4:1 |
| 9 | 134 | 159 | 0.948 | 4:1 |
| 10 | 130 | 161 | 0.936 | 4:1 |
| 11 | 131 | 164 | 0.960 | 4:1 |
| 12 | 135 | 176 | 0.890 | 3:2 |
| 13 | 135 | 193 | 0.890 | 1:9 |
| 14 | 137 | 200 | 0.995 | 1:9 |

Distillation fractions 8–11 consisting of the compound having the structure:

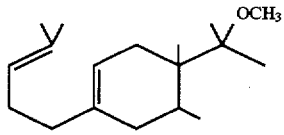

as confirmed by NMR, IR and mass spectral analyses are bulked for perfumery uses.

EXAMPLE V

PREPARATION OF α-ETHYL-α,1,6-TRIMETHYL-4-(4-METHYL-3-PENTENYL)-3-CYCLOHEXENE-1-METHANOL

Reactions:

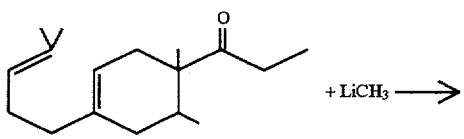

and

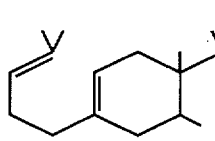

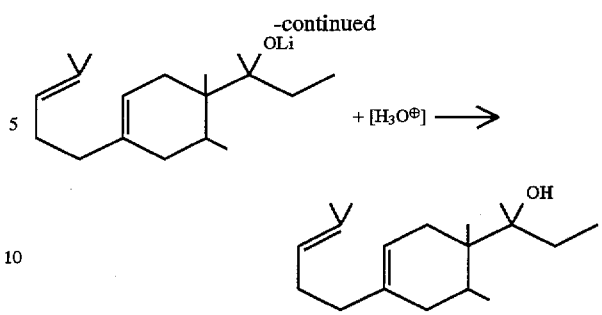

Into a 5 liter reaction vessel equipped with stirrer, thermometer, reflux condenser, heating mantle and addition funnel is placed a solution of 1,600 ml of methyl lithium (1.4 molar) in diethyl ether (2.24 moles). The methyl lithium solution is cooled to 0° C. Over a period of 2 hours, 400 grams (1.6 moles) of the compound having the structure:

is added to the reaction mass, while maintaining the reaction mass with stirring at a temperature of 0° C. The reaction mass is then stirred for an additional 2 hours at 0° C.

The reaction mass is then quenched with 1 liter of 10% aqueous acetic acid. The reaction mass is then transferred to a 5 liter separatory funnel and the aqueous phase is separated from the organic phase. The organic phase is washed with three 1 liter portions of saturated aqueous sodium bicarbonate solution followed by one 1 liter portion of water. The resulting product is then filtered through anhydrous sodium sulfate yielding 1,061 grams of crude product. The resulting product is then distilled on a "rushover" column yielding the following fractions:

| Fraction Number | Vapor Temperature (°C.) | Liquid Temperature (°C.) | Vacuum mm/Hg. Pressure |
|---|---|---|---|
| 1 | 46 | 80/135 | 1.5/9.23 |
| 2 | 90 | 184 | 5.44 |
| 3 | 166 | 152 | 3.72 |
| 4 | 174 | 215 | 2.15 |

Fractions 2 and 3 are bulked and redistilled on a fractionation column yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 64/157 | 169/174 | 1.22/1.47 | 9:1 |
| 2 | 147 | 177 | 1.42 | 9:1 |
| 3 | 143 | 173 | 1.27 | 9:1 |
| 4 | 139 | 172 | 1.09 | 9:1 |
| 5 | 139 | 173 | 1.03 | 9:1 |
| 6 | 155 | 175 | 1.81 | 9:1 |
| 7 | 148 | 174 | 1.27 | 9:1 |
| 8 | 140 | 174 | 1.02 | 9:1 |
| 9 | 150 | 175 | 1.44 | 9:1 |
| 10 | 146 | 175 | 1.25 | 9:1 |
| 11 | 153 | 179 | 1.76 | 9:1 |

-continued

| Fraction Number | Vapor Temperature (°C.) | Liquid Temperature (°C.) | Vacuum mm/Hg. Pressure | Reflux Ratio |
| --- | --- | --- | --- | --- |
| 12 | 154 | 179 | 1.89 | 9:1 |
| 13 | 154 | 202 | 2.02 | 9:1 |

Distillation fractions 8–12 are bulked. Distillation fractions 8–12 consist of the compound having the structure:

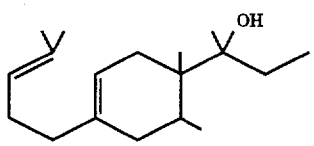

as confirmed by NMR, IR and mass spectral analyses.

EXAMPLE VI

PREPARATION OF MIXTURE OF α,α,1,6-TETRAMETHYL-4-(4-METHYL-3-PENTENYL)-3-CYCLOHEXENE-1-METHANOL ACETIC ACID ESTER AND α,α,1,6-TETRAMETHYL-1-(2-PROPENYL)-4-(4-METHYL-3-PENTENYL)-3-CYCLOHEXENE

Reaction:

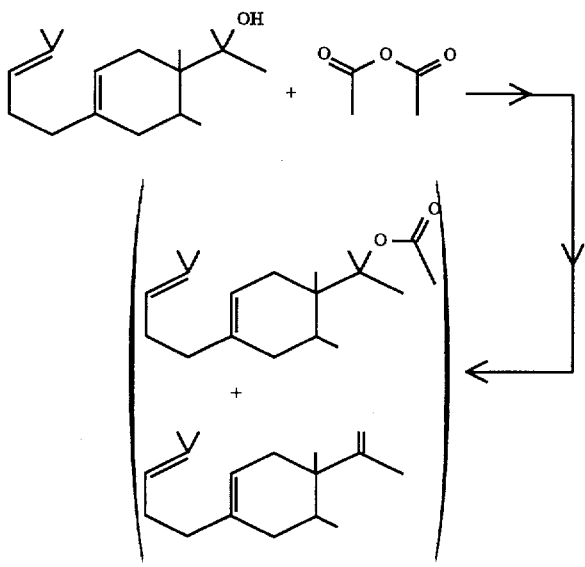

Into a 3 liter reaction vessel equipped with stirrer, thermometer, addition funnel and cooling coils are placed 161 grams (1.58 moles) of acetic anhydride and 2.92 grams of methanesulfonic acid. With stirring, the resulting mixture is cooled to –6° C. While maintaining the reaction mass at –6° C. over a period of 2 hours, 292 grams of the compound having the structure:

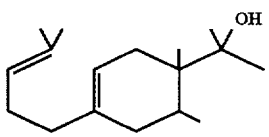

prepared according to Example I is added to the reaction mass with stirring. At the end of the 2 hour period, the reaction mass is permitted to warm up to 2° C. and maintained at 2° C. for a period of 4 hours.

The reaction mass is then quenched with 1 liter of water and added to a separatory funnel. The organic phase is separated from the aqueous phase and the organic phase is washed with two 1 liter volumes of 10% aqueous sodium bicarbonate followed by two 1 liter volumes of saturated aqueous sodium bicarbonate.

The resulting product is then filtered through anhydrous sodium sulfate yielding 240 grams of product. The resulting product is distilled on a "rushover" column yielding the following fractions:

| Fraction Number | Vapor Temperature (°C.) | Liquid Temperature (°C.) | Vacuum mm/Hg. Pressure |
| --- | --- | --- | --- |
| 1 | 32/35 | 52/161 | 1.93/76 |
| 2 | 42/45 | 62/153 | 2.35/25 |
| 3 | 126 | 181 | 0.880 |
| 4 | 130 | 145 | 2.05 |
| 5 | 143 | 200 | 1.75 |

Fractions 3 and 4 are bulked and redistilled on a fractionation column yielding the following fractions:

| Fraction Number | Vapor Temperature (°C.) | Liquid Temperature (°C.) | Vacuum mm/Hg. Pressure | Reflux Ratio |
| --- | --- | --- | --- | --- |
| 1 | 92/103 | 131/132 | 0.795/1.06 | 9:1 |
| 2 | 106 | 139 | 0.990 | 9:1 |
| 3 | 104 | 138 | 0.978 | 9:1 |
| 4 | 107 | 134 | 1.02 | 9:1 |
| 5 | 106 | 133 | 0.900 | 9:1 |
| 6 | 105 | 133 | 0.900 | 9:1 |
| 7 | 107 | 134 | 0.890 | 9:1 |
| 8 | 97 | 134 | 1.01 | 9:1 |
| 9 | 98 | 134 | 1.01 | 9:1 |
| 10 | 92 | 136 | 0.895 | 9:1 |
| 11 | 93 | 134 | 0.885 | 9:1 |
| 12 | 96 | 133 | 0.960 | 9:1 |
| 13 | 99 | 146 | 0.954 | 9:1 |
| 14 | 104 | 151 | 1.09 | 9:1 |
| 15 | 115 | 178 | 1.09 | 9:1 |

Distillation fractions 8–13 are bulked and contain 95 mole percent of the compound having the structure:

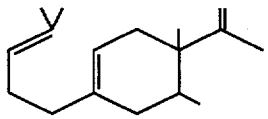

and 5 mole percent of the compound having the structure:

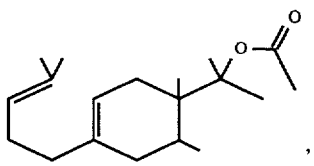

as confirmed by NMR, IR and mass spectral analyses. Bulked distillation fractions 8–13 are used for their organoleptic properties.

EXAMPLE VII

PREPARATION OF α,α,1,6-TETRAMETHYL-4-(4-METHYL-3-PENTENYL)-CYCLOHEXANE-1-METHANOL

EXAMPLE VII(A)

Reaction:

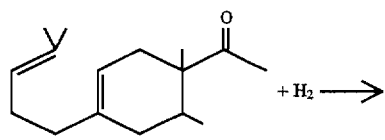

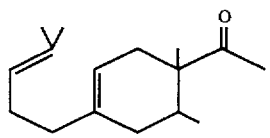

Into a 2 liter autoclave equipped with hydrogen feedline is placed 1,281 grams (5.47 moles) of the compound having the structure:

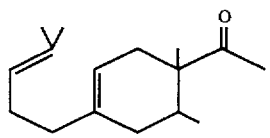

and 7 grams of a 1.5% palladium on carbon catalyst. The autoclave is sealed and heated to a temperature in the range of 75°–110° C. and pressurized with hydrogen to a pressure of 400 psig. The hydrogen pressure is maintained at 400 psig for a period of 4 hours and the temperature is maintained at 79°–110° C. for the 4 hour period.

At the end of the 4 hour period, the autoclave is cooled and opened and the contents are filtered.

The resulting product is fractionally distilled yielding the following fractions:

| Fraction Number | Vapor Temperature (°C.) | Liquid Temperature (°C.) | Vacuum mm/Hg. Pressure |
|---|---|---|---|
| 1 | 51/31 | 71/84 | 140/6.2 |
| 2 | 123 | 151 | 1.56 |
| 3 | 121 | 151.9 | 1.39 |
| 4 | 129 | 152 | 1.99 |
| 5 | 114 | 152 | 0.655 |
| 6 | 110 | 153 | 0.570 |
| 7 | 140 | 198 | 0.520 |

Fractions 2–6 are bulked for subsequent use in Example VIII, infra. The resulting product has the structure:

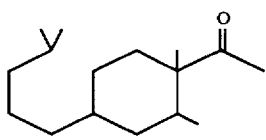

as confirmed by NMR, IR and mass spectral analyses.

EXAMPLE VII(B)

Reactions:

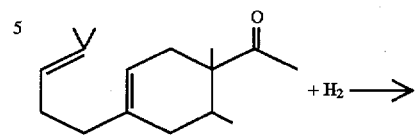

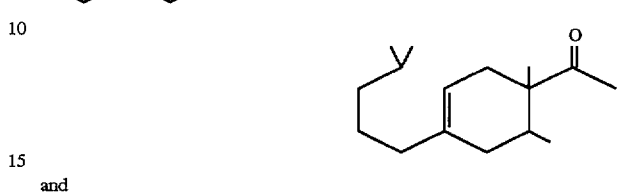

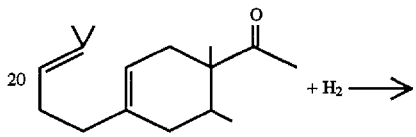

and

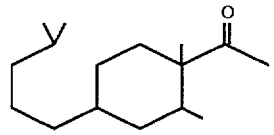

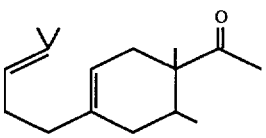

Into a 2 liter autoclave equipped with hydrogen feedline are placed 1,107 grams of the compound having the structure:

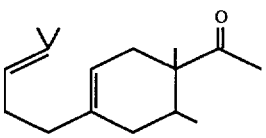

and 6 grams of a 1.5% palladium on carbon catalyst. The autoclave is sealed and the temperature is raised to 39°–43° C. and pressurized with hydrogen at 350 psig. The autoclave is maintained at a temperature of 39°–43° C. for a period of 6 hours and at a pressure of 350 psig. At the end of the 6 hour period, the autoclave is cooled and opened and the contents are filtered. The contents are fractionally distilled and the resulting product contains the following materials:

(i) 27% by weight of the compound having the structure:

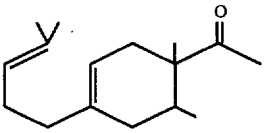

(ii) 37% by weight of the compound having the structure:

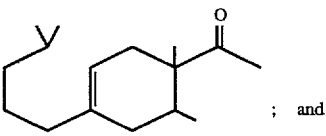

(iii) 29% by weight of the compound having the structure:

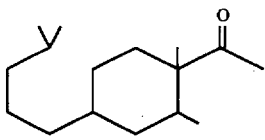

EXAMPLE VII(C)

Reactions:

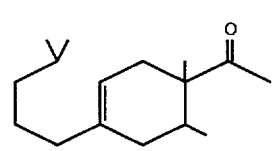 +H₂ ⟶

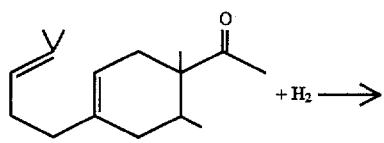

and

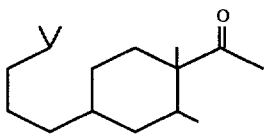 +H₂ ⟶

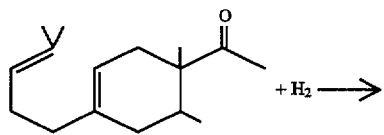

Into a 2 liter autoclave equipped with hydrogen feedline are placed the following materials:

(i) 1,074 grams of the compound having the structure:

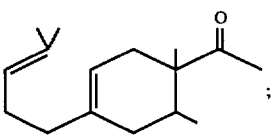 ; and (ii) 5 grams of a 1.5% palladium on carbon catalyst.

The autoclave is sealed and the contents are heated to a temperature of 32° C. and pressurized with hydrogen at a pressure of 350 psig. The autoclave is maintained at 32° C. and 350 psig for a period of 3 hours.

At the end of the 3 hour period, the autoclave is cooled and opened and the contents are filtered. The resulting product contains the following materials:

(i) 14% by weight of the compound having the structure:

(ii) 45% by weight of the compound having the structure:

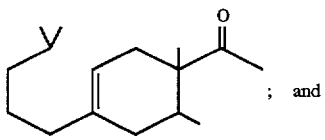 ; and (iii) 30% by weight of the compound having the structure:

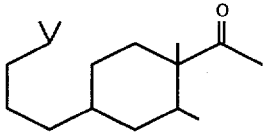

EXAMPLE VIII

PREPARATION OF α,α,1,6-TETRAMETHYL-4-(4-METHYLPENTYL)-CYCLOHEXANE-1-METHANOL

Reactions:

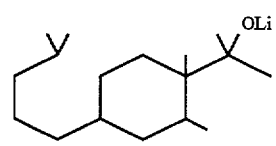 + LiCH₃ ⟶

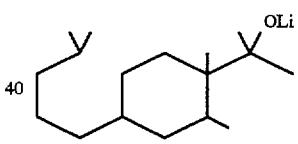

and

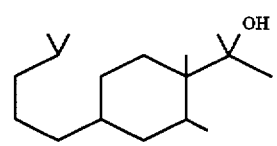 + [H₃O⊕] ⟶

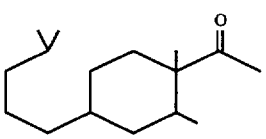

Into a 5 liter reaction vessel equipped with stirrer, thermometer, addition funnel, heating mantle and cooling coils is placed 1,600 ml of a solution of methyl lithium in diethyl ether (1.4 molar; 2.24 moles). The methyl lithium solution is cooled to 0° C. With stirring over a period of 2 hours, 381 grams (1.6 moles) of the compound having the structure:

prepared according to Example VII(A) is added to the reaction mass.

At the end of the 2 hour period, the reaction mass is stirred for 1.5 hours at 0° C.

The reaction mass is then quenched with 1 liter of 10% aqueous acetic acid. The reaction mass is transferred to a 5 liter separatory funnel and the organic phase is separated from the aqueous phase. The organic phase is washed with three 1 liter volumes of saturated sodium bicarbonate followed by one 1 liter volume of water. The resulting product is then filtered through anhydrous sodium sulfate yielding 367 grams of product. The resulting product is then fractionally distilled on a "rushover column" yielding the following fractions:

| Fraction Number | Vapor Temperature (°C.) | Liquid Temperature (°C.) | Vacuum mm/Hg. Pressure |
|---|---|---|---|
| 1 | 118 | 151 | 0.725 |
| 2 | 130 | 154 | 0.725 |
| 3 | 142 | 160 | 2.56 |
| 4 | 26 | 300 | 1.13 |

Fractions 2 and 3 are bulked and redistilled yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 155 | 171 | 0.795 | 9:1 |
| 2 | 153 | 169 | 0.577 | 9:1 |
| 3 | 153 | 169 | 0.785 | 9:1 |
| 4 | 119 | 167 | 0.700 | 9:1 |
| 5 | 143 | 163 | 0.730 | 9:1 |
| 6 | 131 | 165 | 2.34 | 9:1 |
| 7 | 139 | 164 | 2.50 | 9:1 |
| 8 | 144 | 165.6 | 2.61 | 9:1 |
| 9 | 139 | 163.3 | 2.49 | 9:1 |
| 10 | 143 | 164.1 | 2.30 | 9:1 |
| 11 | 140 | 166.3 | 1.83 | 9:1 |
| 12 | 141 | 163.1 | 1.87 | 9:1 |
| 13 | 129 | 157 | 1.72 | 9:1 |
| 14 | 127 | 154 | 1.55 | 9:1 |
| 15 | 128 | 154 | 1.55 | 9:1 |
| 16 | 128 | 157 | 1.54 | 9:1 |
| 17 | 102 | 160 | 0.520 | 9:1 |
| 18 | 110 | 155 | 0.495 | 4:1 |
| 19 | 108 | 157 | 0.495 | 4:1 |
| 20 | 109 | 160 | 0.488 | 4:1 |
| 21 | 110 | 160 | 0.480 | 4:1 |
| 22 | 109 | 160 | 0.489 | 4:1 |
| 23 | 107 | 160 | 0.480 | 4:1 |
| 24 | 118 | 176 | 0.480 | 1:9 |
| 25 | 124 | 182 | 0.800 | 1:9 |
| 26 | 125 | 189 | D.700 | 1:9 |
| 27 | 108 | 200 | 0.570 | 1:9 |

Fractions 13–25 are bulked for use in Example IX and for use for their organoleptic properties.

Bulked distillation fractions 13–25 consist of the compound having the structure:

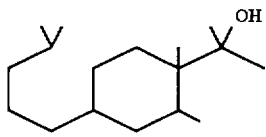

as confirmed by NMR, IR and mass spectral analyses.

EXAMPLE IX

PREPARATION OF 1-(1-METHOXY-1-METHYL ETHYL)-1,2 -DIMETHYL-4-(4-METHYLPENTYL)-CYCLOHEXANE

Reactions:

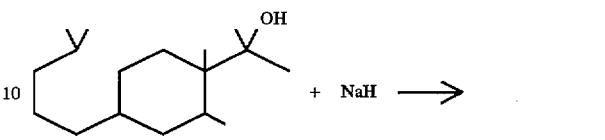

and

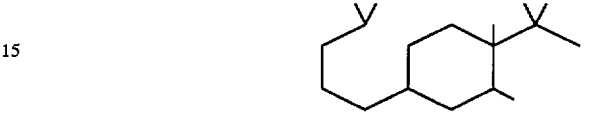

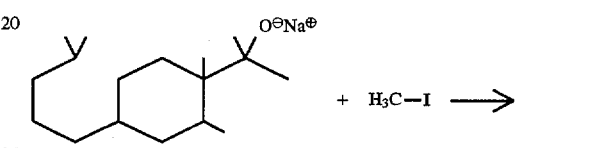

Into a 5 liter reaction vessel equipped with stirrer, thermometer, reflux condenser and heating mantle are placed 62.4 grams of sodium hydride and 624 ml tetrahydrofuran. The resulting sodium hydride solution is heated to reflux at 65° C.

Over a period of 2 hours, 508 grams (2 moles) of the compound having the structure:

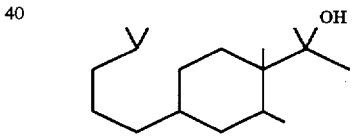

prepared according to Example VIII is added to the reaction mass. The reaction mass is then maintained at 82° C. for a period of 2 hours. The product in the reaction mass at this point in time has the structure:

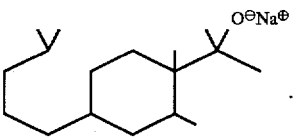

The reaction mass is then cooled to room temperature and over a period of 1.5 hours, 341 grams (2.4 moles) of methyl iodide is added to the reaction mass while maintaining the temperature of the reaction mass at 22°–30° C.

The reaction mass is then maintained with stirring at 24°–30° C. for a period of 7 hours.

At the end of the 7 hour period, the reaction mass is quenched with three 1 liter volumes of water. The reaction mass is then filtered through anhydrous sodium sulfate yielding 1,194 grams of product.

The reaction mass is then distilled on a "rushover column" yielding the following fractions:

| Fraction Number | Vapor Temperature (°C.) | Liquid Temperature (°C.) | Vacuum mm/Hg. pressure |
|---|---|---|---|
| 1 | 33/57 | 50/113 | 87/143 |
| 2 | 124 | 156 | 0.924 |
| 3 | 137 | 200 | 0.890 |

Fractions 2 and 3 are bulked and redistilled on a fractionation column yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 112/140 | 154/158 | 1.36/13 | 9:1 |
| 2 | 139 | 156 | 1.34 | 9:1 |
| 3 | 139 | 156 | 1.32 | 9:1 |
| 4 | 141 | 156 | 1.32 | 9:1 |
| 5 | 142 | 157 | 1.56 | 9:1 |
| 6 | 143 | 157 | 1.57 | 9:1 |
| 7 | 143 | 157 | 1.32 | 9:1 |
| 8 | 144 | 158 | 1.27 | 9:1 |
| 9 | 143 | 158 | 1.27 | 9:1 |
| 10 | 144 | 157 | 1.28 | 9:1 |
| 11 | 147 | 160 | 1.28 | 9:1 |
| 12 | 130 | 158 | 1.28 | 9:1 |
| 13 | 130 | 160 | 1.27 | 9:1 |
| 14 | 130 | 157.2 | 1.26 | 9:1 |
| 15 | 131 | 158 | 1.29 | 9:1 |
| 16 | 130 | 160.1 | 1.26 | 9:1 |
| 17 | 132 | 157.3 | 1.30 | 9:1 |
| 18 | 132 | 162.2 | 1.30 | 9:1 |
| 19 | 133 | 157.7 | 1.33 | 9:1 |
| 20 | 133 | 163 | 1.34 | 9:1 |

Distillation fractions 9–17 are bulked and consist of the compound having the structure:

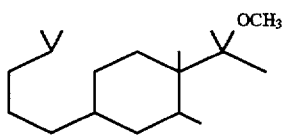

as confirmed by NMR, IR and mass spectral analyses. Bulked distillation fractions 9–17 are used subsequently for their organoleptic properties.

EXAMPLE X

PREPARATION OF MIXTURE OF α,α,1,2-TETRAMETHYL-4-(4-METHYLPENTYL) CYCLOHEXANE METHANOL ACETATE AND α,α,1,2-TETRAMETHYL-1-(2-PROPENYL)-4-(4-METHYL)-CYCLOHEXANE

Reaction:

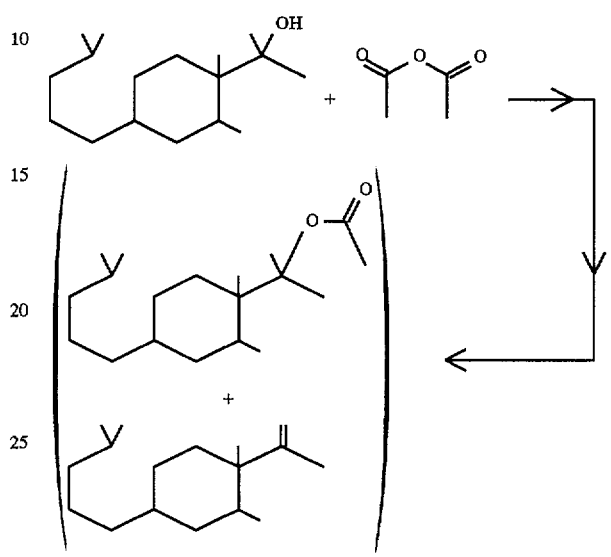

Into a 2 liter reaction vessel equipped with stirrer, thermometer, reflux condenser and cooling coils are placed 306 grams (3 moles) of acetic anhydride and 5.08 grams of methanesulfonic acid. The resulting mixture is cooled to 0° C. with stirring.

With stirring over a period of 2 hours, 508 grams (2 moles) of the compound having the structure:

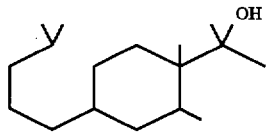

is added to the reaction mass. The Compound having the structure:
is prepared according to Example VIII, bulked distillation fractions 13–24. The reaction mass is stirred at 0° C. for a period of 2.5 hours.

At the end of the 2.5 hour period, the reaction mass is quenched with one 1 liter portion of water followed by two 1 liter portions of 10% aqueous sodium bicarbonate followed by two 1 liter portions of aqueous saturated sodium bicarbonate.

The resulting product is then filtered through anhydrous sodium sulfate and distilled on a "rushover" column yielding the following fractions:

| Fraction Number | Vapor Temperature (°C.) | Liquid Temperature (°C.) | Vacuum mm/Hg. Pressure |
|---|---|---|---|
| 1 | 98/113 | 131/120 | 0.37/0.4 |
| 2 | 99 | 200 | 0.557 |

Bulked distillation fractions 1 and 2 contain 82 mole percent of the compound having the structure:

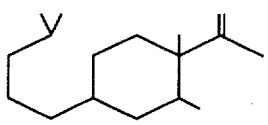

and 18 mole percent of the compound having the structure:

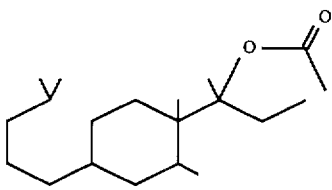

as confirmed by NMR, IR and mass spectral analyses taken together with GLC analysis. The resulting mixture is used subsequently for its organoleptic properties.

EXAMPLE XI

FRAGRANCE FORMULATIONS

To demonstrate the use of the 1(4'-methylpentyl)-4-substituted ethylcyclohexane derivatives of our invention prepared according to Examples I, II and III in magnolia, musk and citrusy formulations, the following formulae are prepared:

| Ingredients | Parts by Weight | | |
|---|---|---|---|
| | XI (A) | XI (B) | XI (C) |
| Phenylethyl alcohol | 200 | 25 | 25 |
| Geraniol | 400 | 25 | 25 |
| Trichloromethylphenyl carbinyl acetate | 20 | 5 | 5 |
| Phenylethyl acetate | 60 | 5 | 5 |
| Undecylenic aldehyde (10% in diethyl phthalate) | 5 | 0 | 0 |
| n-Nonyl aldehyde (10% in diethyl phthalate) | 2 | 0 | 0 |
| Musk ketone | 10 | 150 | 20 |
| Musk ambrette | 10 | 150 | 20 |
| Eugenyl phenyl acetate | 20 | 5 | 5 |
| Citronellol | 100 | 100 | 400 |
| Vanillin (10% in diethyl phthalate) | 6 | 6 | 6 |
| Eugenol | 30 | 5 | 5 |
| Citronellyl formate | 30 | 5 | 5 |
| Geranyl acetate | 10 | 5 | 5 |
| Linalool | 40 | 20 | 20 |
| Geranyl phenyl acetate | 50 | 20 | 20 |
| Cis-beta, Gamma-hexenyl acetate | 2 | 0 | 0 |
| 1-(2,5,5-Trimethyl-1,3-cyclohexadien-1-yl)-1,3-butanedione | 5 | 5 | 5 |
| Farnesene isomer mixture produced according to Example I of U.S. Pat. No. 4,394,444 (the specification for which is incorporated by reference herein). | 60 | 60 | 40 |
| The compound having the structure: 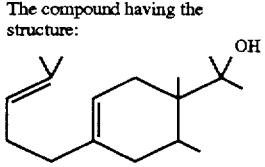 prepared according to Example I, bulked distillation fractions 22-27. | 120 | 0 | 0 |
| The compound having the structure: 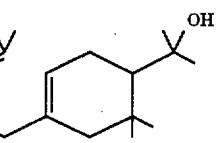 prepared according to Example II, bulked distillation fractions 5-9 | 0 | 120 | 0 |
| The compound having the structure: 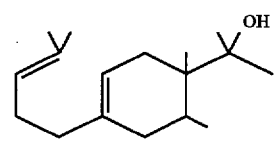 produced according to Example III, bulked distillation fractions 7 and 8. | 0 | 0 | 120 |

The addition of the compound having the structure:

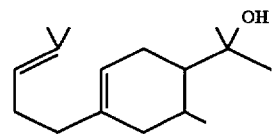

prepared according to Example I, bulked distillation fractions 22-27 adds to the fragrance of Example XI(A) patchouli, ambery, earthy, woody, peach, mimosa and camphoraceous undertones with patchouli, camphoraceous, earthy, musty and woody topnotes. Accordingly, the perfume composition of Example XI(A) can be described as "a magnolia aroma with intense patchouli, ambery, earthy, woody, peach, mimosa and camphoraceous undertones with patchouli, camphoraceous, earthy, musty and woody topnotes".

The addition of the compound having the structure:

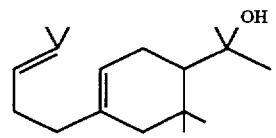

prepared according to Example II, bulked distillation fractions 5-9 adds a patchouli undertone to this musk formulation. Accordingly, the perfume composition of Example XI(B) can be described as "a musk aroma with patchouli undertones".

The addition of the compound having the structure:

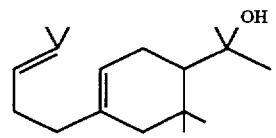

prepared according to Example III, bulked distillation fractions 7 and 8, adds a woody and mahogany undertone to this citrus formulation. Accordingly, the perfume composition of Example XI(C) can be described as "a citrus aroma with woody and mahogany undertones".

EXAMPLE XII

FRAGRANCE FORMULATIONS

To demonstrate the use of the 1(4'-methylpentyl)-4-substituted ethylcyclohexane derivatives of our invention prepared according to Examples IV, V and VI in magnolia, musk and citrusy formulations, the following formulae are prepared:

| Ingredients | Parts by Weight | | |
|---|---|---|---|
| | XII (A) | XII (B) | XII (C) |
| Phenylethyl alcohol | 200 | 25 | 25 |
| Geraniol | 400 | 25 | 25 |
| Trichloromethylphenyl carbinyl acetate | 20 | 5 | 5 |
| Phenylethyl acetate | 60 | 5 | 5 |
| Undecylenic aldehyde (10% in diethyl phthalate) | 5 | 0 | 0 |
| n-Nonyl aldehyde (10% in diethyl phthalate) | 2 | 0 | 0 |
| Musk ketone | 10 | 150 | 20 |
| Musk ambrette | 10 | 150 | 20 |
| Eugenyl phenyl acetate | 20 | 5 | 5 |
| Citronellol | 100 | 100 | 400 |
| Vanillin (10% in diethyl phthalate) | 6 | 6 | 6 |
| Eugenol | 30 | 5 | 5 |
| Citronellyl formate | 30 | 5 | 5 |
| Geranyl acetate | 10 | 5 | 5 |
| Linalool | 40 | 20 | 20 |
| Geranyl phenyl acetate | 50 | 20 | 20 |
| Cis-beta, Gamma-hexenyl acetate | 2 | 0 | 0 |
| 1-(2,5,5-Trimethyl-1,3-cyclohexadien-1-yl)-1,3-butanedione | 5 | 5 | 5 |
| Farnesene isomer mixture produced according to Example I of U.S. Pat. No. 4,394,444 (the specification for which is incorporated by reference herein). | 60 | 60 | 40 |
| The compound having the structure: | 120 | 0 | 0 |

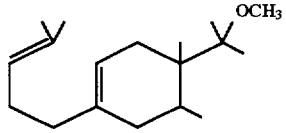

prepared according to Example IV, bulked distillation fractions 8-11.

| | | | |
|---|---|---|---|
| The compound having the structure: | 0 | 120 | 0 |

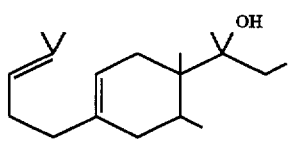

prepared according to Example V, bulked distillation fractions 8-12.

| | | | |
|---|---|---|---|
| The compound having the structure: | 0 | 0 | 120 |

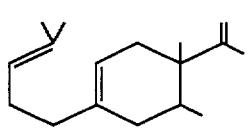

produced according to Example VI, bulked distillation fractions 8 and 13.

The addition of the compound having the structure:

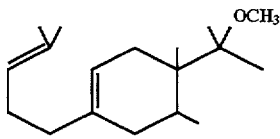

prepared according to Example IV, bulked distillation fractions 8-11 imparts to the magnolia formulation of Example XII(A) woody and patchouli undertones with green topnotes. Accordingly, the perfume composition of Example XII(A) can be described as "a magnolia aroma with intense woody and patchouli undertones and green topnotes".

The addition of the compound having the structure:

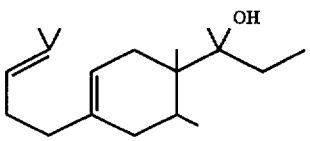

prepared according to Example V, bulked distillation fractions 8-12 adds to the musk formulation of Example XII(B) camphoraceous and piney undertones. Accordingly, the perfume composition of Example XII(B) can be described as "a musk aroma with camphoraceous and piney undertones".

The addition of the compound having the structure:

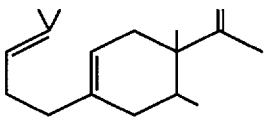

prepared according to Example VI, bulked distillation fractions 8-13, imparts to the citrus formulation of Example XII(C) woody undertones. Accordingly, the perfume composition of Example XII(C) can be described as "a citrus aroma with woody undertones".

EXAMPLE XIII

FRAGRANCE FORMULATIONS

To demonstrate the use of 1(4'-methylpentyl)-4-substituted ethylcyclohexane derivatives of our invention prepared according to Examples VIII and IX in magnolia and musk formulations, the following formulae are prepared:

| Ingredients | Parts by Weight | |
|---|---|---|
| | XIII (A) | XIII (B) |
| Phenylethyl alcohol | 200 | 25 |
| Geraniol | 400 | 25 |
| Trichloromethylphenyl carbinyl acetate | 20 | 5 |
| Phenylethyl acetate | 60 | 5 |
| Undecylenic aldehyde (10% in diethyl phthalate) | 5 | 0 |
| n-Nonyl aldehyde (10% in diethyl phthalate) | 2 | 0 |
| Musk ketone | 10 | 150 |
| Musk ambrette | 10 | 150 |
| Eugenyl phenyl acetate | 20 | 5 |
| Citronellol | 100 | 100 |
| Vanillin (10% in diethyl phthalate) | 6 | 6 |
| Eugenol | 30 | 5 |
| Citronellyl formate | 30 | 5 |

-continued

| Ingredients | Parts by Weight | |
|---|---|---|
| | XIII (A) | XIII (B) |
| Geranyl acetate | 10 | 5 |
| Linalool | 40 | 20 |
| Geranyl phenyl acetate | 50 | 20 |
| Cis-beta, Gamma-hexenyl acetate | 2 | 0 |
| 1-(2,5,5-Trimethyl-1,3-cyclohexadien-1-yl)-1,3-butanedione | 5 | 5 |
| Franesene isomer mixture produced according to Example I of U.S. Pat. No. 4,394,444 (the specification for which is incorporated by reference herein). | 60 | 60 |
| The compound having the structure: 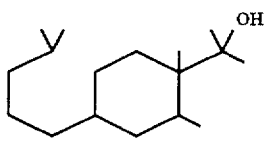 produced according to Example VIII, bulked distillation fractions 13–24. | 120 | 0 |
| The compound having the structure: 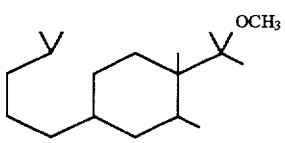 prepared according to Example IX, bulked distillation fractions 9–17. | 0 | 120 |

The addition of the compound having the structure:

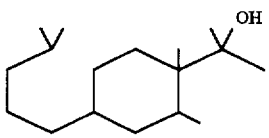

prepared according to Example VIII, bulked distillation fractions 13–24, imparts to the magnolia formulation of Example XIII(A) woody, patchouli, animalic and musk undertones. Accordingly, the perfume composition of Example XIII(A) can be described as "a magnolia aroma with intense woody, patchouli, animalic and musk undertones".

The addition of the compound having the structure:

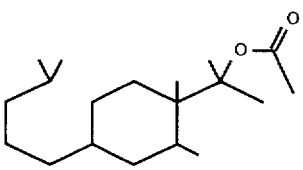

prepared according to Example IX, bulked distillation fractions 9–17 imparts to the musk formulation of Example XIII(B) a patchouli, ambery and woody undertone with fruity topnotes. Accordingly, the perfume composition of Example XIII(B) can be described as "a musk aroma having patchouli, ambery and woody undertones with fruity topnotes".

EXAMPLE XIV

PREPARATION OF SOAP COMPOSITION

100 Grams of soap chips are produced according to Example V of U.S. Pat. No. 4,058,487 issued on Nov. 15, 1977, the specification for which is incorporated by reference herein, as follows:

The sodium salt of an equal mixture of $C_{10}$–$C_{14}$ alkane sulfonates (95% active), 40 pounds, is dissolved in a mixture of 80 pounds of anhydrous isopropanol and 125 pounds of dionized water at 150° F. In this mixture is dissolved 10 pounds of partially hydrogenated coconut oil, fatty acids and 15 pounds of sodium mono-$C_{14}$-alkylmaleate. The pH of the solution is adjusted to 6.0 by the addition of a small amount of a 50% aqueous sodium hydroxide solution. The isopropanol is distilled off and the remaining aqueous solution is drum dried. The resulting solid actives are then blended in a mixture with 10 pounds of water, 0.2 pounds of titanium hydroxide and 0.75 pounds of one of the materials set forth below:

TABLE II

| Perfume Ingredient | Aroma Profile |
|---|---|
| The compound having the structure: 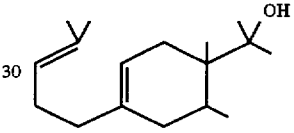 prepared according to Example I, bulked distillation fractions 22–27. | A patchouli, ambery, earthy, woody, peach, mimosa and camphoraceous aroma with patchouli, camphoraceous, earthy, musty and woody topnotes. |
| The compound having the structure: 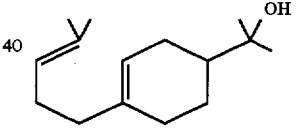 prepared according to Example II, bulked distillation fractions 5–9. | A patchouli aroma. |
| The compound having the structure: 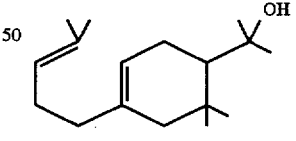 prepared according to Example III, bulked distillation fractions 7 and 8. | A woody and mahogany aroma. |
| The compound having the structure: 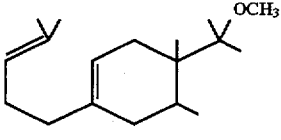 produced according to Example IV, bulked distillation | A woody, patchouli aroma with green topnotes. |

TABLE II-continued

| Perfume Ingredient | Aroma Profile |
|---|---|
| fractions 8–11. | |
| The compound having the structure: 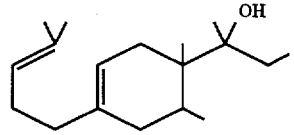  produced according to Example V, bulked distillation fractions 8–12. | A camphoraceous and piney aroma. |
| The compound having the structure: 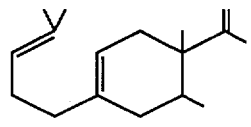  produced according to Example VI, bulked distillation fractions 8–13. | A woody aroma. |
| The compound having the structure: 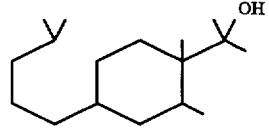  produced according to Example VIII, bulked distillation fractions 13–24. | A woody, patchouli, animalic and musky aroma. |
| The compound having the structure: 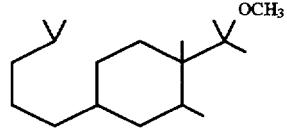  produced according to Example IX, bulked distillation fractions 9–17. | A patchouli, ambery and woody aroma with fruity topnotes. |
| Perfume composition of Example XI (A). | A magnolia aroma with intense patchouli, ambery, earthy, woody, peach, mimosa and camphoraceous undertones with patchouli, camphoraceous, earthy, musty and woody topnotes. |
| Perfume composition of Example XI (B) | A musk aroma with patchouli undertones. |
| Perfume composition of Example XI (C). | A citrus aroma with woody and mahogany undertones. |
| Perfume composition of Example XII (A). | A magnolia aroma with intense woody and patchouli undertones and green topnotes. |
| Perfume composition of Example XII (B). | A musk aroma with camphoraceous and piney undertones. |
| Perfume composition of Example XII (C). | A citrus aroma with woody undertones. |
| Perfume composition of Example XIII (A). | A magnolia aroma with intense woody, patchouli, animalic and musk undertones. |
| Perfume composition of Example XIII (B). | A musk aroma having patchouli, ambery and woody undertones with fruity topnotes. |

The chips are then plodded into logs, cut to size and finally stamped into bars, having a pH of approximately 6.9.

Each of the perfumed soaps of Table II above manifests an excellent characteristic aroma as indicated in Table II above. Furthermore, each of the perfumed soaps is non-discoloring.

EXAMPLE XV

PREPARATION OF A DETERGENT COMPOSITION

A total of 100 grams of a detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of one of the perfume ingredients of Table II of Example XIV, supra, until a substantially homogeneous composition is obtained. This composition has an excellent aroma as indicated according to Table II of Example XIV, supra.

EXAMPLE XVI

PREPARATION OF COSMETIC POWDER COMPOSITIONS

A cosmetic powder is prepared by mixing in a ball mill 100 grams of talcum powder with 0.25 grams of one of the perfume materials of Table II of Example XIV, supra. Each of the cosmetic powders has an excellent aroma as set forth in Table II of Example XIV, supra.

EXAMPLE XVII

PERFUMED LIQUID DETERGENTS

Concentrated liquid detergents having aromas as set forth in Table II of Example XIV, supra, are prepared by adding 0.10%, 0.15% and 0.20% of each of the perfume ingredients of Table II of Example XIV, supra. They are prepared by adding and homogeneously mixing the appropriate quantity of perfume material in the liquid detergent. The detergents all possess aromas as set forth in Table II of Example XIV, supra.

EXAMPLE XVIII

PREPARATION OF COLOGNE AND HANDKERCHIEF PERFUMES

Each of the compositions of Table II of Example XIV, supra, is incorporated into colognes at several concentrations, 2.0%, 2.5%, 3.0%, 3.5%, 4.0% and 5.0% in 70%, 75%, 80%, 85% and 90% aqueous ethanol; and into handkerchief perfumes at concentrations of 10%, 15%, 20% and 25% (in 80%, 85%, 90% and 95% aqueous ethanol). The use of each of the perfume ingredients as set forth in Table II of Example XIV, supra, affords distinctive aromas as set forth in Table II of Example XIV, supra.

EXAMPLE XIX

PREPARATION OF A DETERGENT COMPOSITION

A total of 100 grams of a detergent powder (a nonionic detergent powder containing a proteolytic enzyme prepared according to Example I of Canadian Patent No. 985,190 issued on Mar. 9, 1976) is mixed with 0.15 grams of a perfume material set forth in Table II of Example XIV, supra, until a substantially homogeneous composition is obtained in each case. Each of the compositions has an excellent aroma as set forth in Table II of Example XIV, supra.

EXAMPLE XX

Utilizing the procedure of Example I of column 15 of U.S. Pat. No. 3,632,396 (which is hereby incorporated by reference into the instant specification), a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS;
   22% isopropyl alcohol;
   20% antistatic agent; and
   2.5% of one of the perfume materials of Table II of Example XIV, supra.

A fabric-softening composition prepared as set forth above having an aroma characteristic as set forth in Table II of Example XIV, supra, consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of the substrate. The resulting aromas can be described as set forth in Table II of Example XIV, supra, and are imparted in pleasant manners to the head space in the dryer on operation thereof using said dryer-added fabric-softening nonwoven fabric.

EXAMPLE XXI

PERFUMED POLYETHYLENE

Scented polyethylene pellets having a pronounced aroma as set forth in Table II of Example XIV, supra, are prepared as follows (in accordance with Example III of U.S. Pat. No. 3,505,432 which is incorporated by reference herein):

75 Pounds of polyethylene having a melting point of about 220° F. are heated to about 230° F. in a container of the kind illustrated in FIGS. 1 and 2 of U.S. Pat. No. 3,505,432. 25 Pounds of one of the perfume materials of Table II of Example XIV, supra, are then quickly added to the liquified polyethylene, the lid is put in place and the agitating means are actuated. The temperature is maintained at about 225° F. and the mixing is continued for about 15 minutes. The valve is then opened to allow flow of the molten polyethylene enriched with the perfume containing material to exit through the orifices as indicated in FIGS. 1 and 2 of U.S. Pat. No. 3,505,432. The liquid falling through the orifices solidifies almost instantaneously upon impact with the moving cooled conveyor. Solid polyethylene beads or pellets having a pronounced aroma as set forth in Table II of Example XIV, supra, are thus formed. Analysis demonstrates that the pellets contain about 25% of the perfume substance of Table II of Example XIV, supra, so that almost no losses in the scenting substance occur. These pellets may be called master pellets. 50 Pounds of the perfume substance containing master pellets are then added to 1,000 pounds of unscented polyethylene powder and the mass is heated to the liquid state. The liquid is molded into thin sheets or films. The thin sheets or films have a pronounced aroma as set forth in Table II of Example XIV, supra.

EXAMPLE XXII

SCENTED POLYPROPYLENE

100 Pounds of polypropylene are heated to about 300° F. 30 Pounds of one of the aroma materials of Table II of Example XIV, supra, are added to the liquified polypropylene. The procedure is carried out in the apparatus of FIGS. 1 and 2 of U.S. Pat. No. 3,505,432. After mixing for about 8 minutes, the valve is opened to allow the exit of the polypropylene-scented material mixture whereby solid pellets having a pronounced aroma as set forth in Table II of Example XIV, supra, are formed on the conveyor. The pellets thus obtained are then admixed with about 20 times their weight of unscented polypropylene and the mixture is heated and molded into flat discs. The flat discs have a strong and pleasant aroma as set forth in Table II of Example XIV, supra.

EXAMPLE XXIII

A perfumed polymer is produced by admixing a microporous polymer produced according to one of Examples 194–236 of U.S. Pat. No. 4,247,498 (the disclosure of which is incorporated by reference herein), and applying a 0.5 mm/Hg. vacuum to the system. The resulting product is then compressed into pellets and molded into fragrance-emitting plastic objects, e.g., automobile dashboards.

What is claimed is:

1. At least one 1(4'-methylpentyl)-4-substituted ethylcyclohexane derivative defined according to the structure:

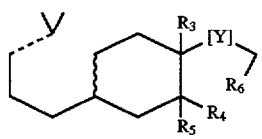

wherein $R_3$, $R_4$, $R_5$ and $R_6$ represent the same or different hydrogen or methyl; wherein the dashed line represents a carbon carbon single bond or a carbon carbon double bond; wherein the wavy line represents a carbon carbon single bond or a carbon carbon double bond; with the proviso that when the wavy line is a carbon carbon single bond then the dashed line is a carbon carbon single bond; wherein Y represents a moiety selected from the group consisting of:

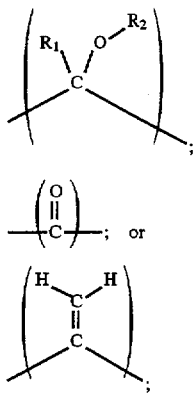

wherein $R_2$ is hydrogen, $C_1$–$C_4$ lower alkyl or $C_1$–$C_2$ acyl; and wherein $R_1$ is $C_1$–$C_4$ lower alkyl with the additional proviso that when Y is the moiety:

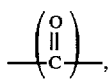

then the dashed line is a carbon carbon single bond.

2. The 1(4'-methylpentyl)-4-substituted ethylcyclohexane derivative of claim 1 having the structure:

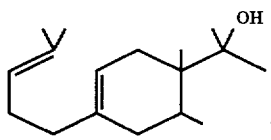

3. The 1(4'-methylpentyl)-4-substituted ethylcyclohexane derivative of claim 1 having the structure:

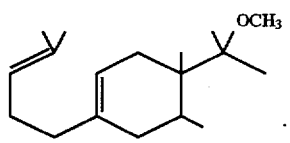

4. The 1(4'-methylpentyl)-4-substituted ethylcyclohexane derivative of claim 1 having the structure:

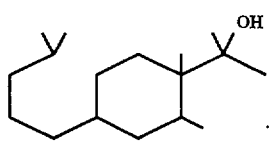

5. The 1(4'-methylpentyl)-4-substituted ethylcyclohexane derivative of claim 1 having the structure:

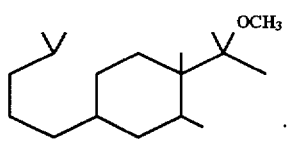

6. A process for augmenting, enhancing or imparting an aroma in or to a consumable material selected from the group consisting of perfume compositions, colognes and perfumed articles comprising the step of adding to said consumable material an aroma augmenting, imparting or enhancing quantity and concentration of at least one 1(4'-methylpentyl)-4-substituted ethylcyclohexane derivative defined according to claim 1.

7. A process for augmenting, enhancing or imparting an aroma in or to a consumable material selected from the group consisting of perfume compositions, colognes and perfumed articles comprising the step of adding to said consumable material an aroma augmenting, imparting or enhancing quantity and concentration of at least one 1(4'-methylpentyl)-4-substituted ethylcyclohexane derivative defined according to claim 2.

8. A process for augmenting, enhancing or imparting an aroma in or to a consumable material selected from the group consisting of perfume compositions, colognes and perfumed articles comprising the step of adding to said consumable material an aroma augmenting, imparting or enhancing quantity and concentration of at least one 1(4'-methylpentyl)-4-substituted ethylcyclohexane derivative defined according to claim 3.

9. A process for augmenting, enhancing or imparting an aroma in or to a consumable material selected from the group consisting of perfume compositions, colognes and perfumed articles comprising the step of adding to said consumable material an aroma augmenting, imparting or enhancing quantity and concentration of at least one 1(4'-methylpentyl)-4-substituted ethylcyclohexane derivative defined according to claim 4.

10. A process for augmenting, enhancing or imparting an aroma in or to a consumable material selected from the group consisting of perfume compositions, colognes and perfumed articles comprising the step of adding to said consumable material an aroma augmenting, imparting or enhancing quantity and concentration of at least one 1(4'-methylpentyl)-4-substituted ethylcyclohexane derivative defined according to claim 5.

11. A perfume composition consisting essentially of a perfume base and intimately admixed therewith in a perfume imparting, augmenting or enhancing quantity and concentration, at least one 1(4'-methylpentyl)-4-substituted ethylcyclohexane derivative defined according to claim 1.

12. A perfume composition consisting essentially of a perfume base and intimately admixed therewith in a perfume imparting, augmenting or enhancing quantity and concentration, at least one 1(4'-methylpentyl)-4-substituted ethylcyclohexane derivative defined according to claim 2.

13. A solid or liquid anionic, cationic, nonionic or zwitterionic detergent composition consisting essentially of a solid or liquid anionic, cationic, nonionic or zwitterionic detergent base and intimately admixed therewith an aroma augmenting, enhancing or imparting quantity or concentration of at least one 1(4'-methylpentyl)-4-substituted ethylcyclohexane derivatives defined according to claim 1.

14. A solid or liquid anionic, cationic, nonionic or zwitterionic detergent composition consisting essentially of a solid or liquid anionic, cationic, nonionic or zwitterionic detergent base and intimately admixed therewith an aroma augmenting, enhancing or imparting quantity or concentration of at least one 1(4'-methylpentyl)-4-substituted ethylcyclohexane derivatives defined according to claim 2.

15. A perfumed polymer consisting essentially of a microporous polymer and containing in the interstices thereof an aroma imparting, augmenting or enhancing quantity of at least one 1(4'-methylpentyl)-4-substituted ethylcyclohexane derivative defined according to claim 1.

16. A perfumed polymer consisting essentially of a microporous polymer and containing in the interstices thereof an aroma imparting, augmenting or enhancing quantity of at least one 1(4'-methylpentyl)-4-substituted ethylcyclohexane derivative defined according to claim 2.

17. The organometallic compound having the structure:

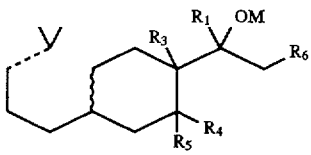

wherein $R_1$ is $C_1$–$C_4$ lower alkyl; $R_3$, $R_4$, $R_5$ and $R_6$ each represent the same or different hydrogen or methyl; the dashed line represents a carbon carbon single bond or a carbon carbon double bond; the wavy line represents a carbon carbon single bond or a carbon carbon double bond with the proviso that when the wavy line is a carbon carbon single bond, then the dashed line is a carbon carbon single bond; and wherein M represents Li or MgX and wherein X is chloro or bromo.

18. The organometallic compound having the structure:

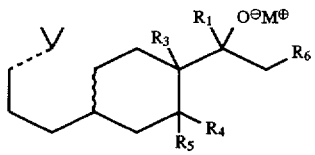

wherein $R_1$ represents $C_1$–$C_4$ lower alkyl; $R_3$, $R_4$, $R_5$ and $R_6$ each represent the same or different hydrogen or methyl; wherein the dashed line represents a carbon carbon single bond or a carbon carbon double bond; wherein the wavy line represents a carbon carbon single bond or a carbon carbon double bond; with the proviso that when the wavy line is a carbon carbon single bond, then the dashed line is a carbon carbon single bond; and wherein M' is alkali metal.

19. The ketone having the structure:

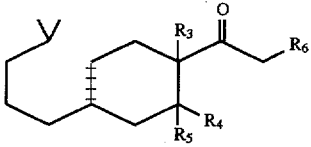

wherein the line: represents a carbon carbon single bond or a carbon carbon double bond and wherein $R_3$, $R_4$, $R_5$ and $R_6$ are the same or different and each represents hydrogen or methyl.

20. The ketone of claim 19 wherein the line: is a carbon carbon single bond.

21. The ketone of claim 19 wherein the line: is a carbon carbon double bond.

22. A mixture of ketones defined according to claim 19 having the structures

* * * * *